(12) United States Patent
Matula et al.

(10) Patent No.: US 8,264,683 B2
(45) Date of Patent: *Sep. 11, 2012

(54) DYNAMIC CHARACTERIZATION OF PARTICLES WITH FLOW CYTOMETRY

(75) Inventors: Thomas J. Matula, Kirkland, WA (US); Jarred Swalwell, Shoreline, WA (US)

(73) Assignee: University of Washington, Seattle, WA (US)

( * ) Notice: Subject to any disclaimer, the term of this patent is extended or adjusted under 35 U.S.C. 154(b) by 301 days.

This patent is subject to a terminal disclaimer.

(21) Appl. No.: 12/497,281

(22) Filed: Jul. 2, 2009

(65) Prior Publication Data

US 2009/0316151 A1 Dec. 24, 2009

Related U.S. Application Data

(63) Continuation-in-part of application No. 11/531,998, filed on Sep. 14, 2006, now Pat. No. 7,804,595.

(60) Provisional application No. 61/077,808, filed on Jul. 2, 2008, provisional application No. 60/716,861, filed on Sep. 14, 2005.

(51) Int. Cl.
*G01N 21/00* (2006.01)

(52) U.S. Cl. .......... 356/337; 424/9.52; 600/453; 702/19

(58) Field of Classification Search .................. 356/337, 356/338; 424/9.52; 600/453; 702/19
See application file for complete search history.

(56) References Cited

U.S. PATENT DOCUMENTS

| | | | | |
|---|---|---|---|---|
| 5,348,002 | A * | 9/1994 | Caro | 600/310 |
| 6,423,007 | B2 | 7/2002 | Lizzi et al. | 424/9.5 |
| 7,374,744 | B2 | 5/2008 | Schutt | 600/458 |
| 7,804,595 | B2 * | 9/2010 | Matula et al. | 356/338 |
| 2006/0290944 | A1 * | 12/2006 | Arnott et al. | 356/519 |
| 2007/0197886 | A1 * | 8/2007 | Naganuma et al. | 600/322 |

OTHER PUBLICATIONS

Allen et al., "Dynamics of therapeutic ultrasound contrast agents," *Ultrasound in Medicine and Biology* vol. 28, No. 6: 805-816, 2002.
Barber et al., "Light Scattering Measurements of the Repetitive Supersonic Implosion of a Sonoluminescing Bubble," *Physical Review Letters* vol. 69, No. 26:3839-3842, Dec. 28, 1992.
Church, C. C., "The effects of an elastic solid surface layer on the radial pulsations of gas bubbles." *Journal of the Acoustical Society of America* vol. 97, No. 3: 1510-1521, 1995.
Dayton et al., "Optical and acoustical observation of the effects of ultrasound on contrast agents," *IEEE Transactions on Ultrasonics, Ferroelectrics, and Freqency Control* vol. 46, No. 1: 220-232, 1999.

(Continued)

*Primary Examiner* — Tarifur Chowdhury
*Assistant Examiner* — Isiaka Akanbi
(74) *Attorney, Agent, or Firm* — Kilpatrick Townsend & Stockton LLP

(57) ABSTRACT

Flow cytometry concepts are modified to enable dynamic characterizations of particles to be obtained using optical scattering data. Particles in flow will be introduced into a sample volume. Light scattered by a particle in the sample volume is collected and analyzed. What differentiates the concepts disclosed herein from conventional flow cytometry is the use of an acoustic source that is disposed to direct acoustic energy into the sample volume. As the particle passes through the sample volume, it responds to the acoustic energy, causing changes in the light scattered by the particle. Those changes, which are not measured during conventional flow cytometry, can be analyzed to determine additional physical properties of the particle.

23 Claims, 28 Drawing Sheets

OTHER PUBLICATIONS de Jong et al, , "Higher harmonics of vibrating gas-filled microspheres, Part one: Simulation," *Ultrasonics* vol, 32, No. 6: 447-452, 1994.

de Jong et al., "Higher harmonies of vibrating gas-filled microspheres. Part two: Measurements." *Ultrasonics* vol, 32, No. 6: 455-458, 1994.

de Jong et al., "Ultrasound scattering properties of Albunex microspheres," *Ultrasonics* vol. 31, No. 3: 175-181 1993.

Forsberg et al., "Effect of filling gasses on the backscattering from contrast microbubbles: Theory and in vivo measurements," *Ultrasound in Medicine and Biology* vol. 25, No. 8:1203-1211, 1999.

Guan et al., "Using light-scattering to measure the response of individual ultrasound contrast microbubbles subjected to pulsed ultrasound in vitro," *Journal of the Acoustical Society of America* vol. 116, No. 5:2832-2842, 2004.

Hansen, Gary., "Mie scattering as a technique for the sizing of air bubbles," *Applied Optics* vol. 24, No. 19: 3214-3220, Oct. 1, 1985.

Hoff et al., "Oscillations of polymeric microbubbles: Effect of the encapsulating shell," *Journal of the Acoustical Society of America* vol. 107, No. 4: 2272-2280, Apr. 2000.

Holt et al., "Mie scattering used to determine spherical bubble oscillations" *Applied Optics* vol. 29, No. 28: 4182-4191, Oct. 1, 1990.

Khismatullin et al., "Radial oscillations of encapsulated microbubbles in viscoelastic liquids." *Physics of Fluids* vol. 14, No. 10: 3534-3557, Oct. 2002.

Langley et al., "Critical-angle scattering of laser light from bubbles in water: measurements, models, and application to sizing of bubbles." *Applied Optics* vol. 23, No. 7: 1044-1054, Apr. 1, 1984.

Marsh et al., "Broadband Measurement of the Scattering-to-Attenuation Ratio for Albunex at 37° C." *Ultrasound in Medicine and Biology* vol. 25, No. 8: 1321-1324, 1999.

Marston et al., "Scattering of light by a coated bubble in water near the critical and Brewster scattering angles." *Oceans Optics IX* Proc. vol. 925: 308-316, 1988.

Moran et al., "Quantification of Microbubble Destruction of Three Fluorocarbon-Filled Ultrasonic Contrast Agents." *Ultrasound in Medicine and Biology* vol. 26, No. 4: 629-639, 2000.

Morgan et al., "Experimental and Theoretical Evaluation of Microbubble Behavior: Effect of Transmitted Phase and Bubble Size," *IEEE Transactions on Ultrasonics, Ferroelectrics, and Frequency Control* vol. 47, No. 6: 1494-1509, Nov. 2000.

Postema et al., "Ultrasound-induced encapsulated microbubble phenomena." *Ultrasound in Medicine and Biology* vol. 30, No. 6: 827-840, 2004.

Sboros et al., "Understanding the limitations of ultrasonic backscattering measurements from microbubble populations." *Physics in Medicine and Biology* vol. 47: 4287-4299, 2002.

Shi et al., "Ultrasonic Characterization of the Nonlinear Properties of Contrast Microbubbles." *Ultrasound in Medicine and Biology* vol. 26, No. 1: 93-104, 2000.

Van der Meer et al., "Microbubble spectroscopy of ultrasound contrast agents," *Journal of the Acoustical Society of America* vol. 121, No. 1: 648-656, 2007.

Wolfrum et al., "Observations of pressure-wave-excited contrast agent bubbles in the vicinity of cells." *Applied Physics Letters* vol. 81, No. 26: 5060-5062, Dec. 23, 2002.

Zhang et al., "The Experimental Investigation of Ultrasonic Properties for a Sonicated Contrast Agent and its Application in Biomedicine." *Ultrasound in Medicine and Biology* vol. 26, No. 2: 347-351, 2000.

\* cited by examiner

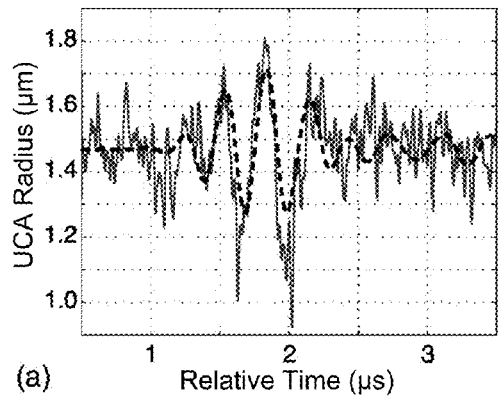
FIG. 5A
FIG. 5B
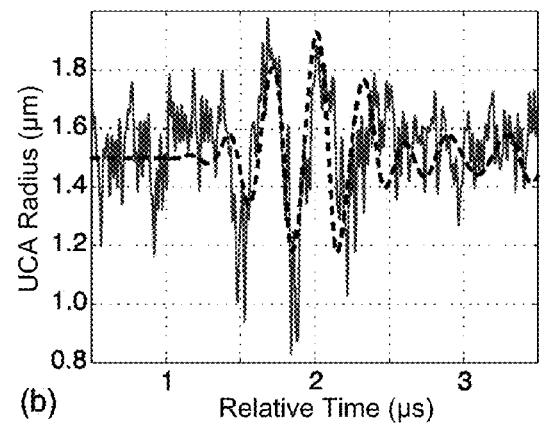
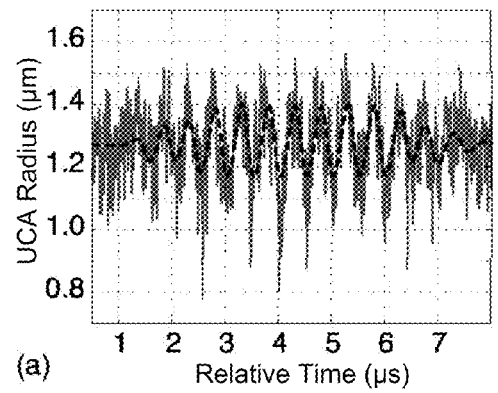
FIG. 6A
FIG. 6B
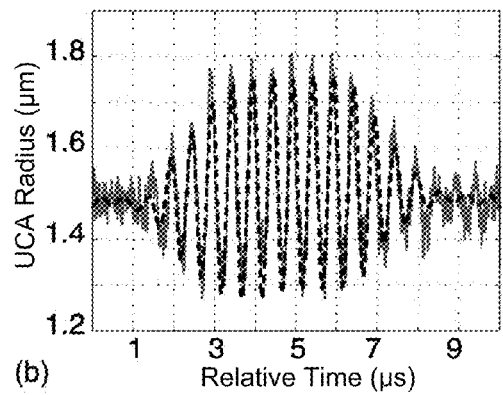

FIG. 8

TABLE I. Response curve parameters. $P^-_{peak}$ is the measured peak negative pressure, $\epsilon\mu_{sh}$ is the assumed shell parameter, $R_0$ is the fitted ambient radius, and $R_{max}$ is the resultant maximum radius.

| Figure | Agent | $\epsilon\mu_{sh}$ (nm Pa s) | Media | Source | $P^-_{peak}$ (kPa) | $R_0$ ($\mu$m) | $R_{max}$ ($\mu$m) | $R_{max}/R_0$ |
|---|---|---|---|---|---|---|---|---|
| Fig. 5(a) | Optison® | 6 | Water | UM4+[a] | 210 | 1.47 | 1.71 | 1.2 |
| Fig. 5(b) | Optison® | 6 | Gel | UM4+[a] | 340 | 1.50 | 1.93 | 1.3 |
| Fig. 6(a) | Optison® | 6 | Water | SET[b] | 70 | 1.27 | 1.4 | 1.1 |
| Fig. 6(b) | Optison® | 6 | Gel | SET[b] | 100 | 1.48 | 1.8 | 1.2 |
| Fig. 7(a) | Sonazoid® | 2 | Water | SET[b] | 130 | 1.4 | 2.1 | 1.5 |
| Fig. 7(b) | Sonazoid® | 2 | Gel | SET[b] | 190 | 1.1 | 2.0 | 1.8 |

[a]Ultramark 4Plus.
[b]Single element transducer.

FIG. 10

TABLE II. Response curve parameters for evolving Sonazoid® microbubble in water. $\epsilon\mu_{sh}$ is the assumed shell parameter, $P^-_{peak}$ is the measured peak negative pressure, $R_0$ is the fitted ambient radius, and $R_{max}$ is the resultant maximum radius.

| Figure | $\epsilon\mu_{sh}$ (nm Pa s) | $P^-_{peak}$ (kPa) | $R_0$ ($\mu$m) | $R_{max}$ ($\mu$m) | $R_{max}/R_0$ |
|---|---|---|---|---|---|
| Fig. 8(a) | 2 | 130 | 1.20 | 1.58 | 1.32 |
| Fig. 8(b) | 2 | 130 | 1.50 | 1.96 | 1.31 |
| Fig. 8(c) | 2 | 130 | 1.90 | 2.39 | 1.26 |

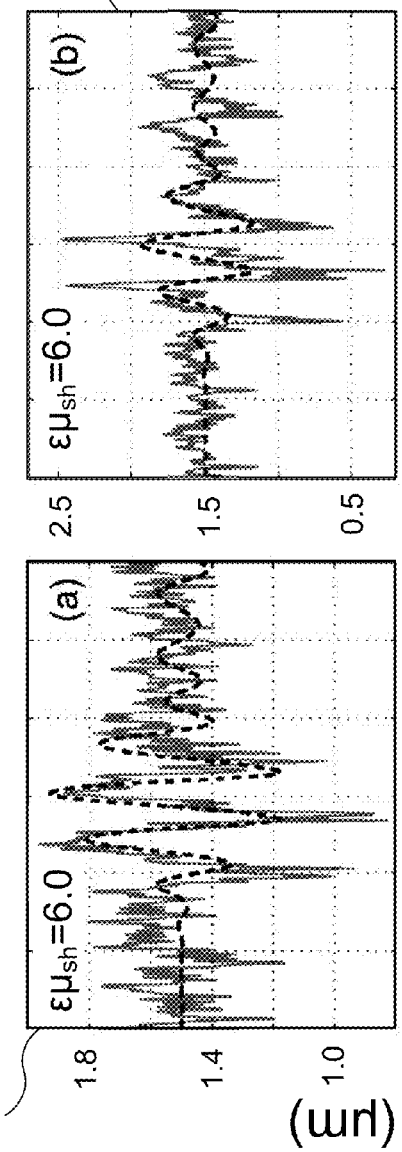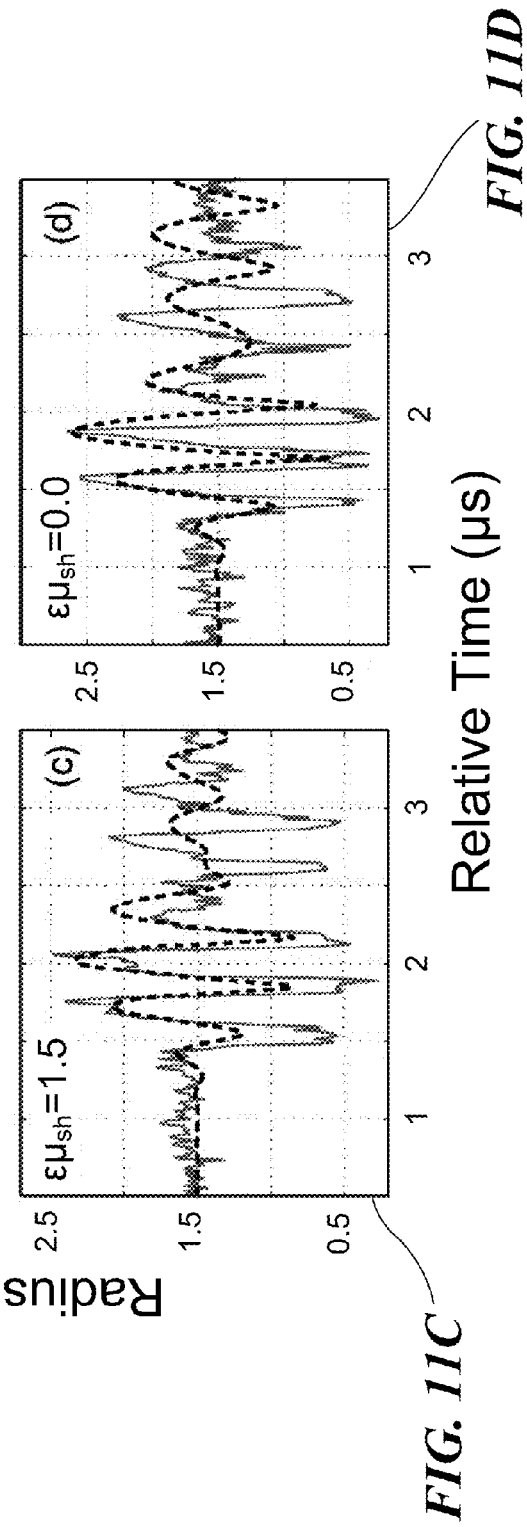
FIG. 11A  FIG. 11B  FIG. 11C  FIG. 11D

TABLE III. Response curve parameters for evolving Optison® microbubble in an aqueous xanthan gum mixture. $P^-_{peak}$ is the measured peak negative pressure, $\epsilon\mu_{sh}$ is the fitted shell parameter, $R_0$ is the fitted ambient radius, and $R_{max}$ is the resultant maximum radius.

| Figure | $P^-_{peak}$ (kPa) | $\epsilon\mu_{sh}$ (nm Pa s) | $R_0$ ($\mu$m) | $R_{max}$ ($\mu$m) | $R_{max}/R_0$ |
|---|---|---|---|---|---|
| Fig. 11A | 340 | 6 | 1.50 | 1.93 | 1.29 |
| Fig. 11B | 340 | 6 | 1.50 | 1.93 | 1.29 |
| Fig. 11C | 340 | 1.5 | 1.50 | 2.33 | 1.55 |
| Fig. 11D | 340 | 0 | 1.50 | 2.61 | 1.68 |

*FIG. 12*

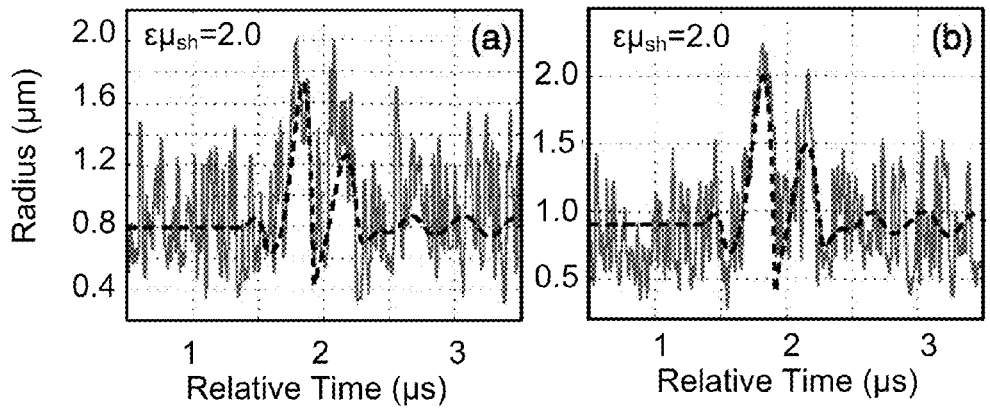

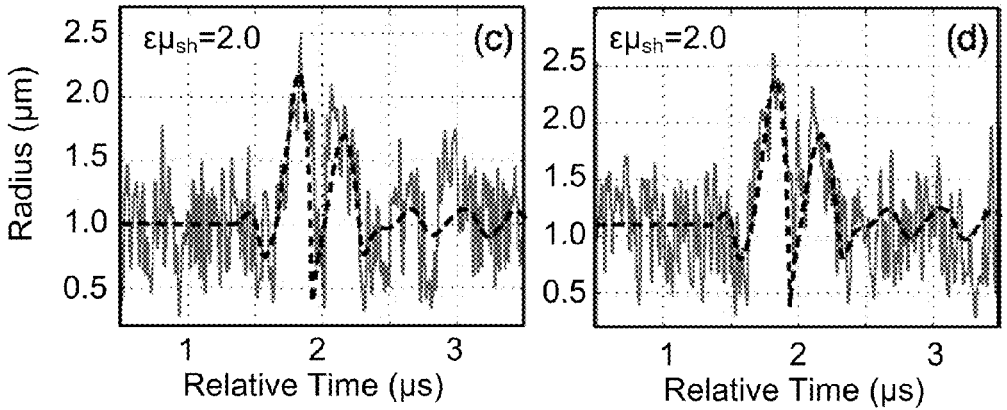

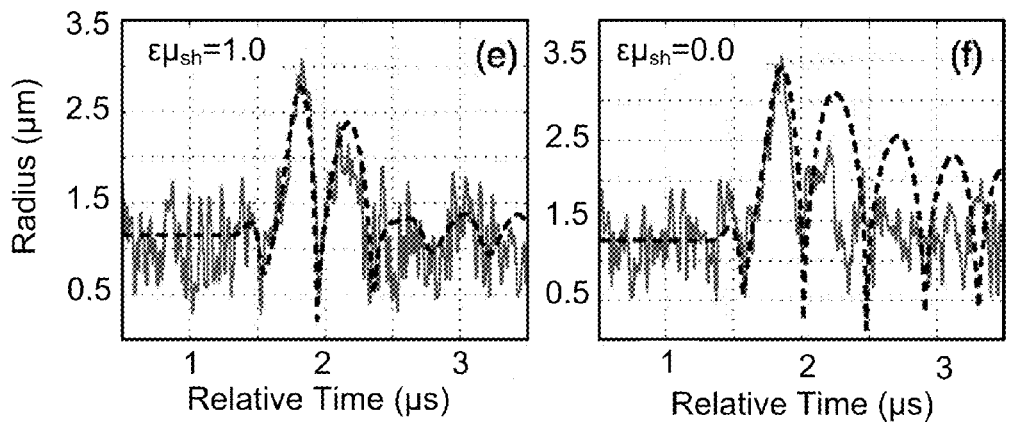

FIG. 13E  FIG. 13F

TABLE IV. Response curve parameters for evolving Sonazoid® microbubble in water. $P^{-}_{peak}$ is the measured peak negative pressure, $\epsilon\mu_{sh}$ is the fitted shell parameter, $R_0$ is the fitted ambient radius, and $R_{max}$ is the resultant maximum radius.

| Figure | $P^{-}_{peak}$ (kPa) | $\epsilon\mu_{sh}$ (nm Pa s) | $R_0$ ($\mu$m) | $R_{max}$ ($\mu$m) | $R_{max}/R_0$ |
|---|---|---|---|---|---|
| Fig. 13A | 390 | 2 | 0.80 | 1.74 | 2.18 |
| Fig. 13B | 390 | 2 | 0.90 | 1.99 | 2.21 |
| Fig. 13C | 390 | 2 | 1.00 | 2.19 | 2.19 |
| Fig. 13D | 390 | 2 | 1.10 | 2.38 | 2.16 |
| Fig. 13E | 390 | 1 | 1.15 | 2.77 | 2.41 |
| Fig. 13F | 390 | 0 | 1.25 | 3.42 | 2.74 |

FIG. 14

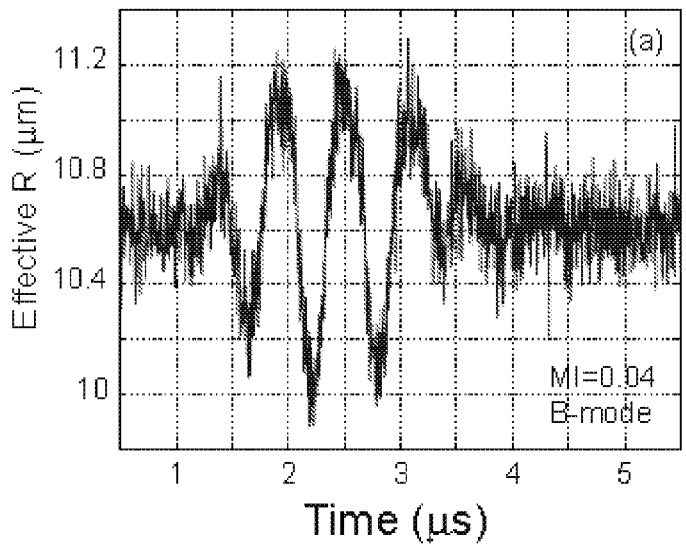
*FIG. 21A*
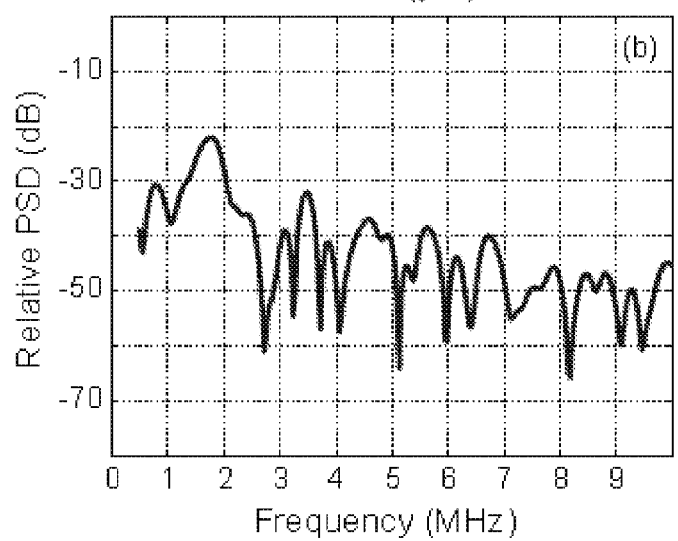
*FIG. 21B*
*FIG. 21C*
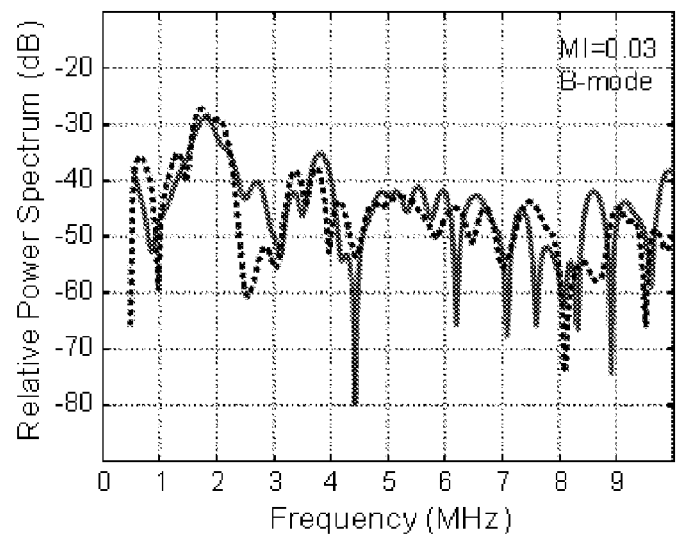

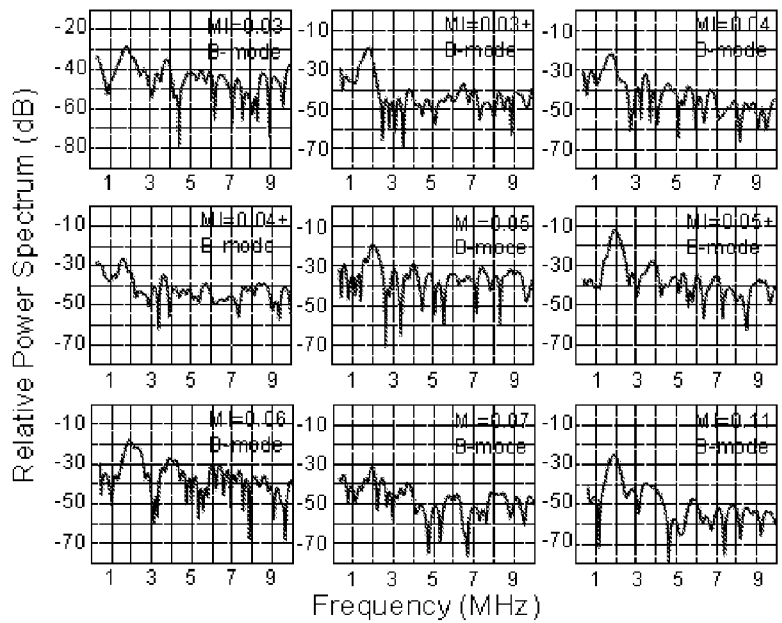
FIG. 22
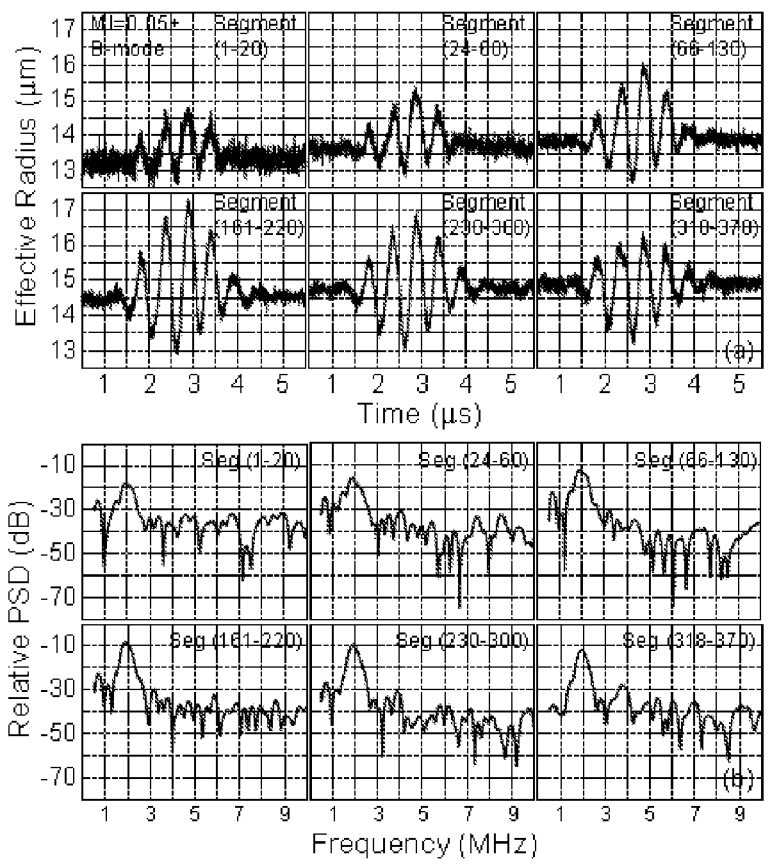
FIG. 23A
FIG. 23B

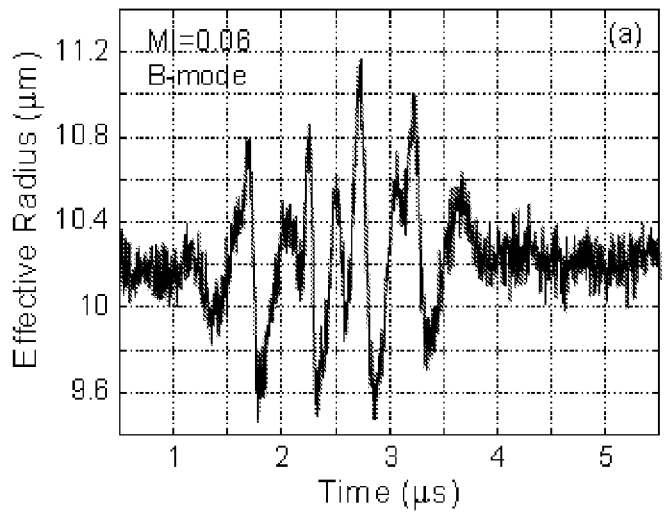
*FIG. 26A*
*FIG. 26B*
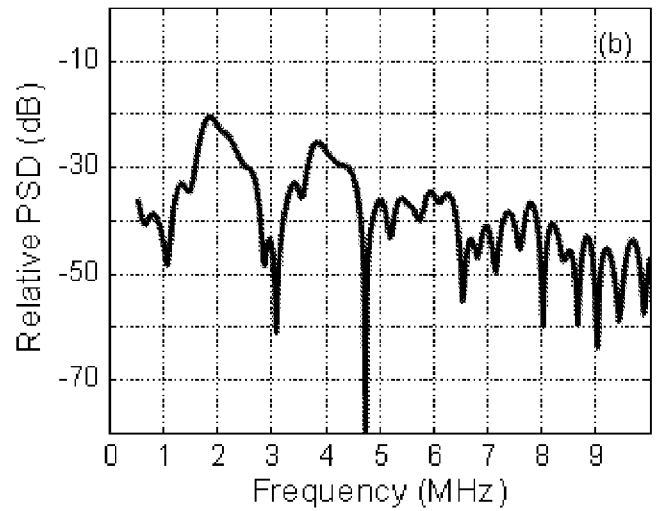
*FIG. 28*
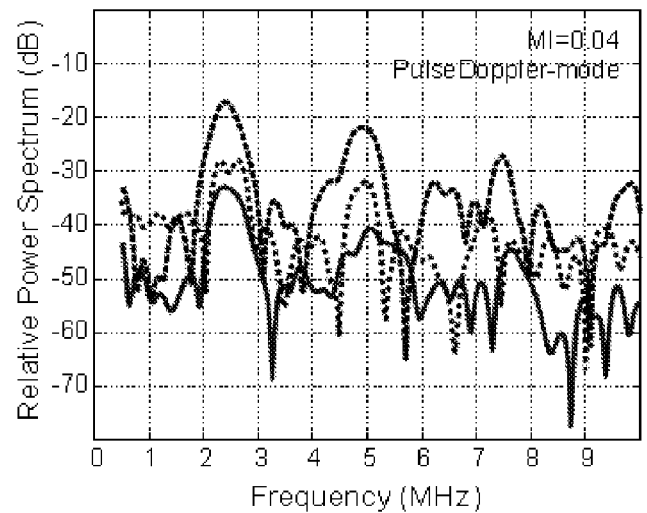

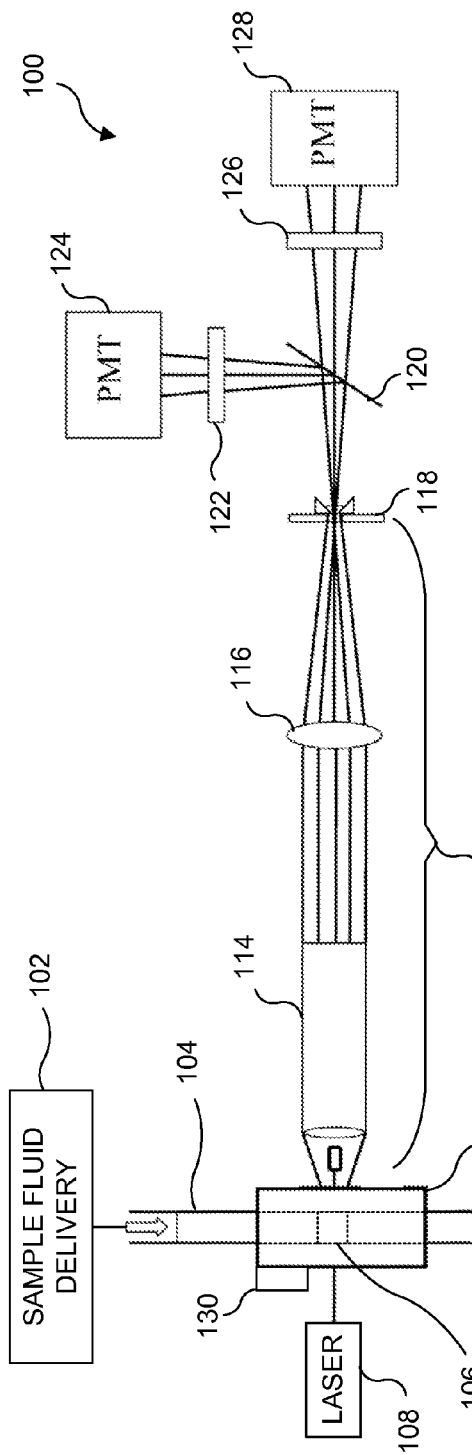
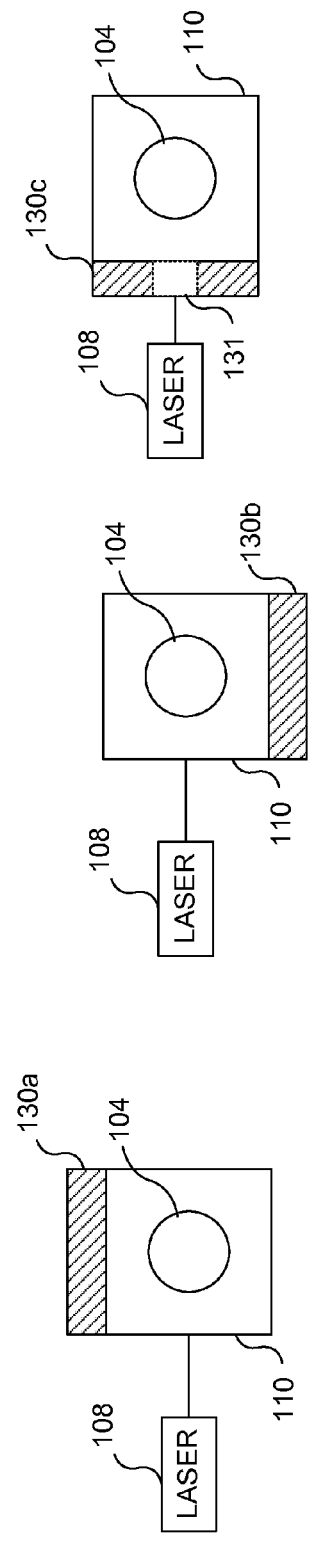
*FIG. 31*
*FIG. 32A*
*FIG. 32B*
*FIG. 32C*

DYNAMIC CHARACTERIZATION OF PARTICLES WITH FLOW CYTOMETRY

RELATED APPLICATIONS

This application is based on a prior provisional application, Ser. No. 61/077,808, filed on Jul. 2, 2008, the benefit of the filing date of which is hereby claimed under 35 U.S.C. §119 (e). This application is further a continuation-in-part of a patent application, Ser. No. 11/531,998, filed on Sep. 14, 2006, now U.S. Pat. No. 7,804,595 which itself is based on a prior provisional application, Ser. No. 60/716,861, filed on Sep. 14, 2005, the benefit of the filing dates of which are hereby claimed under 35 U.S.C. §120 and 35 U.S.C. §119(e), respectively.

GOVERNMENT RIGHTS

This invention was made with U.S. government support under 5R01EB000350 awarded by the National Institutes of Health (NIH). The U.S. government has certain rights in the invention.

BACKGROUND

Efficiently determining the size and physical characteristics of relatively small particles (such as cells or microbubbles) can be a challenging task. In particular, gas-filled microbubbles with an encapsulating shell, generally referred to as ultrasound contrast agents (UCAs), are used regularly in diagnostic ultrasound and are becoming important in therapeutic ultrasound applications. In general, UCAs are very small bubbles, on the order of a micron in diameter, stabilized against dissolution with a coating material (such as a lipid-based material, an albumin-based material, or a polymer-based material). Clearly, the physical properties of any material used for medical applications must be well understood. As such, it would be desirable to provide efficient techniques for investigating the physical properties of UCAs, to enable UCAs to be more effectively used in diagnostic and therapeutic medical applications.

Further, it would thus be desirable if such techniques could be used to efficiently study other types of similar sized particles.

SUMMARY

This application specifically incorporates by reference the disclosures and drawings of each patent application identified above as a related application.

Disclosed herein are techniques to perform the following functions: determining the size of particles (e.g., drops and bubbles); determining their thresholds for changes, such as destruction; and, obtaining information about their dynamic properties using a flow-based instrument that can rapidly analyze large populations of particles.

Particles in flow are introduced into a sample volume. Light scattered by a particle in the sample volume is collected and analyzed, as is also done in conventional flow cytometry. However, the technique disclosed herein is distinguished from conventional flow cytometry by the use of an acoustic source or pressure source that is disposed to direct acoustic energy (or a pressure pulse) into the sample volume. As the particle passes through the sample volume, it responds to the acoustic energy (or pressure pulse), causing changes in the light scattered by the particle. Those changes, which are not measured by conventional flow cytometry, can be analyzed to determine additional physical properties of the particle.

In one exemplary embodiment, the acoustic energy is directed at the particle at a constant rate. In another exemplary embodiment, the acoustic energy is directed at the particle at a variable rate. In still another exemplary embodiment, the acoustic energy is directed at the particle initially and then terminated, so that the scattered light provides information about a decay rate of particle vibrations induced by the acoustic energy (or pressure pulse).

Thus, the concepts disclosed herein employ scattered light to measure the pulsations of an UCA or other particle as it is exposed to acoustic energy or a pressure pulse. In one exemplary embodiment, the particle is introduced into a fluid, and the fluid is directed through a sample volume. The particle is exposed to acoustic energy, while the optical scattering data are processed. The scattering intensity is related to the radius of the particle. Thus, changes in the radius due to vibrations induced in the particle by the acoustic energy results in variations in the scattering intensity. The collected data are processed to provide a radius versus time (RT) relationship. The RT relationship is fit to one or more conventional dynamic models using known techniques (such as linear squares). Depending on the model employed, the fitted empirical data can be used to determine one or more UCA parameters, such as shear modulus, and shell viscosity.

More broadly stated, the scattering intensity (or amplitude) is related to the properties of the particle. Thus, changes in the properties of the particle due to vibrations induced in the particle by the acoustic energy results in variations in the scattering intensity (or amplitude). The collected data are processed to provide an amplitude versus time (AT) relationship. The AT relationship is fit to one or more dynamic models using known techniques. The RT relationship noted above is one type of AT relationship. As noted above, the use of a particle model enables fitted empirical data to be used to determine one or more particle parameters. In an exemplary embodiment, one property being analyzed is the radius of the particle, but it should be recognized that the amplitude changes can be analyzed to determine other particle properties as well. Exemplary properties include, but are not limited to a radius of the particle, a shell viscosity of the particle, and a shear modulus of the particle. The specific parameters that can be determined are a function of the specific particle model being employed. Several specific particle models are discussed herein, but it should be recognized that the empirical AT curve that can be collected by the techniques disclosed herein can be used with many different particle models, and not only those particle models specifically discussed herein.

A system for implementing the light scattering technique includes a sample volume into which the fluid containing the particle can be introduced, a light source for illuminating the particle, a light sensitive detector for collecting light scattered by the particle, an acoustic transducer for directing acoustic energy at the particle, and a processor for manipulating the collected data. Preferably, the light source is a laser, the light sensitive detector is a photomultiplier tube (PMT), and the processor is a computing device (although other types of logical processing devices, such as an applications specific integrated circuit, can also be employed). In an exemplary embodiment, the processor is configured to generate an RT curve (or AT curve) based on the collected data, to fit the curve to one or more pre-defined models, and to calculate one or more parameters based on the fitted RT curve. It should also be recognized that the processor can manipulate the data to determine other parameters.

In general, a conventional flow cytometer can be modified to achieve such a system, by adding the acoustic transducer, and modifying the processor.

The data collected by such a modified flow cytometer can be considered to include dynamic scattering intensity spectrums (or dynamic scattering intensity curves). In yet another embodiment, such dynamic scattering intensity spectrums can be determined for specific particles, and then used to separate those particles from a larger population of particles. In other words, the dynamic scattering intensity spectrums can be used to sort particles based on their spectrums (different particles exhibiting different spectrums).

An exemplary method includes the steps of collecting scattering data using a system generally consistent with the system described above, while a particle is exposed to acoustic energy.

This Summary has been provided to introduce a few concepts in a simplified form that are further described in detail below in the Description. However, this Summary is not intended to identify key or essential features of the claimed subject matter, nor is it intended to be used as an aid in determining the scope of the claimed subject matter.

DRAWINGS

Various aspects and attendant advantages of one or more exemplary embodiments and modifications thereto will become more readily appreciated as the same becomes better understood by reference to the following detailed description, when taken in conjunction with the accompanying drawings, wherein:

FIG. 1 schematically illustrates exemplary method steps for using scattered light to calculate one or more UCA parameters;

FIG. 2 schematically illustrates an exemplary system for implementing the method steps of FIG. 1;

FIG. 3A graphically illustrates the relationship between scattering intensity and scattering angle;

FIG. 3B graphically illustrates the relationship between bubble radius and scattered light intensity;

FIG. 4A is a simulation graphically illustrating the dependence of shell parameters on microbubble size at a particular pressure and frequency;

FIG. 4B graphically illustrates a waterfall plot of the simulated response curve R(t) for various initial bubble sizes and a fixed shell parameter using the same drive amplitude and frequency;

FIG. 4C graphically illustrates an exemplary simulation contour map of $(R_{max}-R_0)$ vs. $R_0$ and $\epsilon\mu_{sh}$ showing the dependence of shell parameters and bubble sizes on the bubble's response to an incident sound pulse;

FIG. 4D graphically illustrates the peak in the power spectral density (the main frequency component) of the simulation shown in FIG. 4A;

FIGS. 5A-5B, 6A-6B, and 7A-7B graphically illustrate empirical data and model fits for two different types of UCAs, in both water and a more viscous liquid (xanthan gum gel);

FIG. 8 (Table I) summarizes parameters for the data set corresponding to FIGS. 5A-5B, 6A-6B, and 7A-7B;

FIGS. 9A-9C graphically illustrate how a Sonazoid™ microbubble in water dynamically evolves over consecutive acoustic pulses, collected using three successive groups of ten pulses;

FIG. 10 (Table II) summarizes parameters for the data set corresponding to FIGS. 9A-9C;

FIGS. 11A-11D graphically illustrate the dynamical evolution of an Optison™ bubble to individual (i.e., non-averaged) pressure pulses from diagnostic ultrasound in an aqueous/xanthan gum solution;

FIG. 12 (Table III) summarizes response curve parameters for the data set corresponding to FIGS. 11A-11D;

FIGS. 13A-13F graphically illustrate the dynamical evolution of a Sonazoid™ bubble in water, showing individual responses (i.e., non-averaged responses) due to consecutive ultrasound pulses;

FIG. 14 (Table IV) summarizes response curve parameters for the data set corresponding to FIGS. 13A-13F;

FIG. 15 graphically illustrates normalized PSDs from FIGS. 9A-9C;

FIG. 16 schematically illustrates yet another exemplary system to collect light scattered by microbubbles during changing pressure conditions;

Figure 18A:
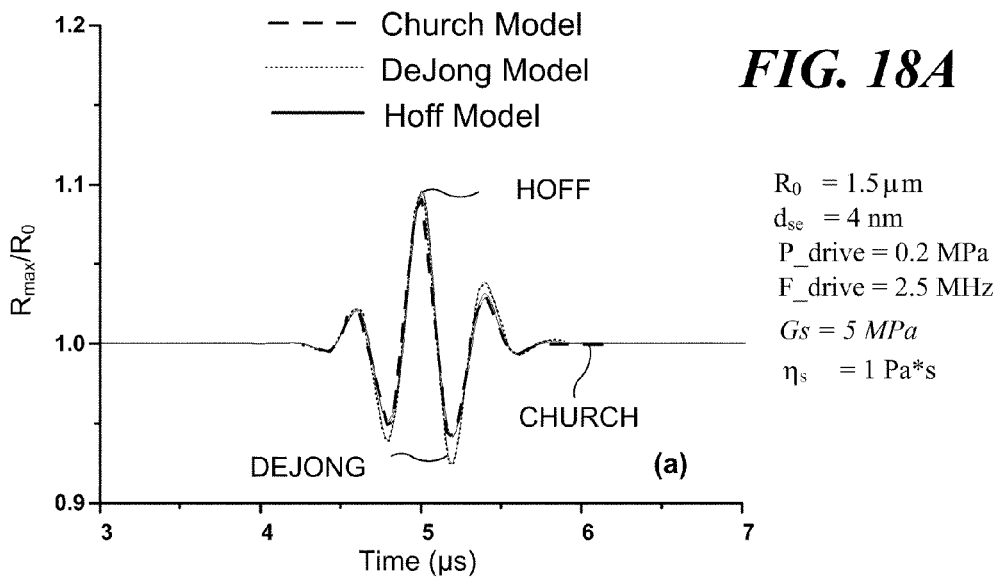
Figure 18B:
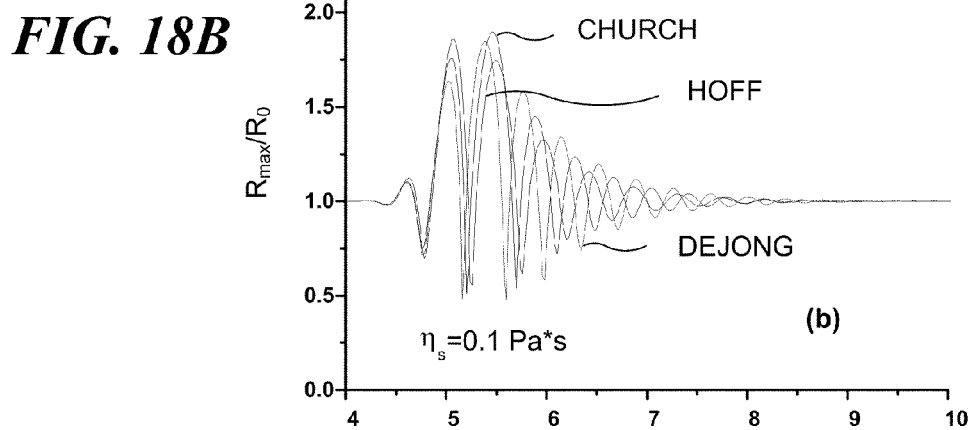
Figure 18C:
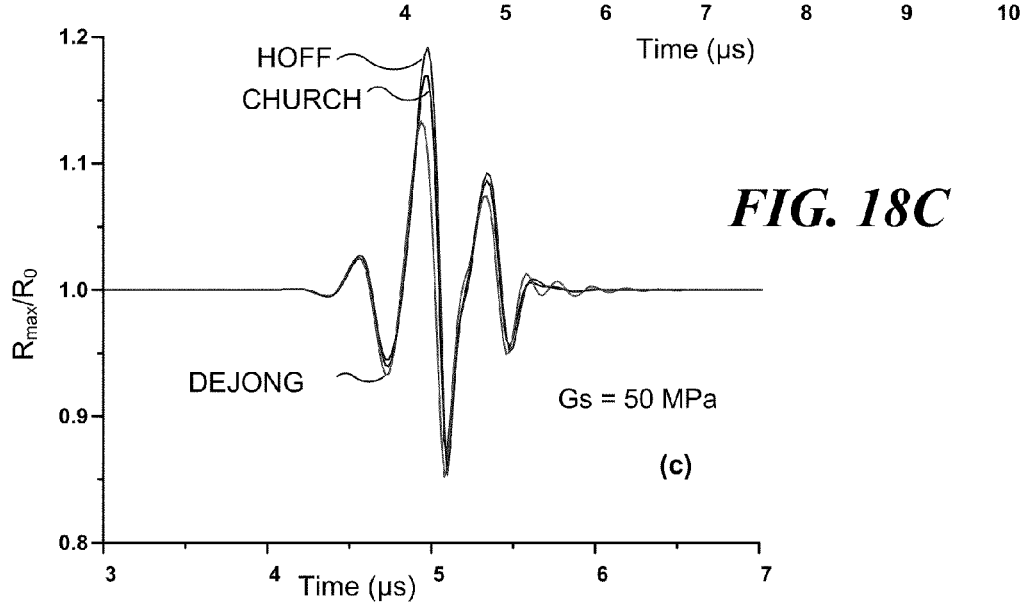
Figure 19A:
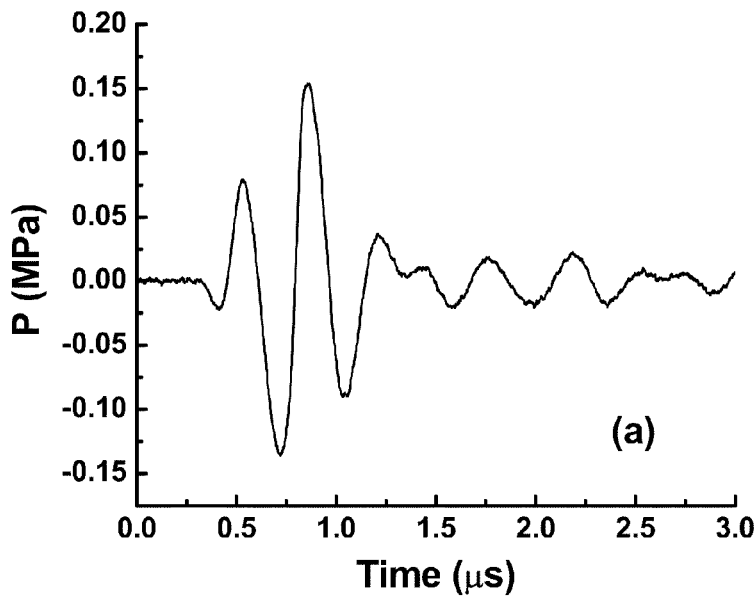
Figure 20A:
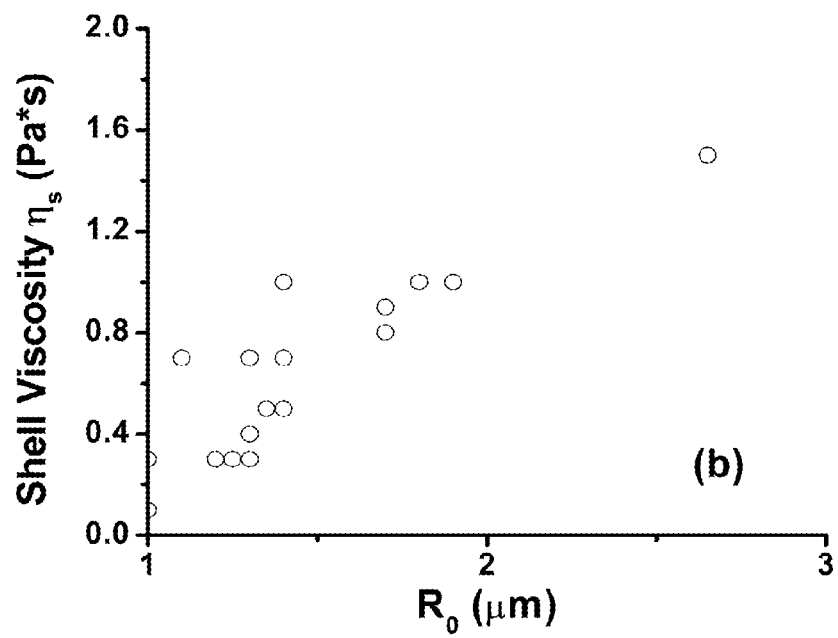
Figure 20B:
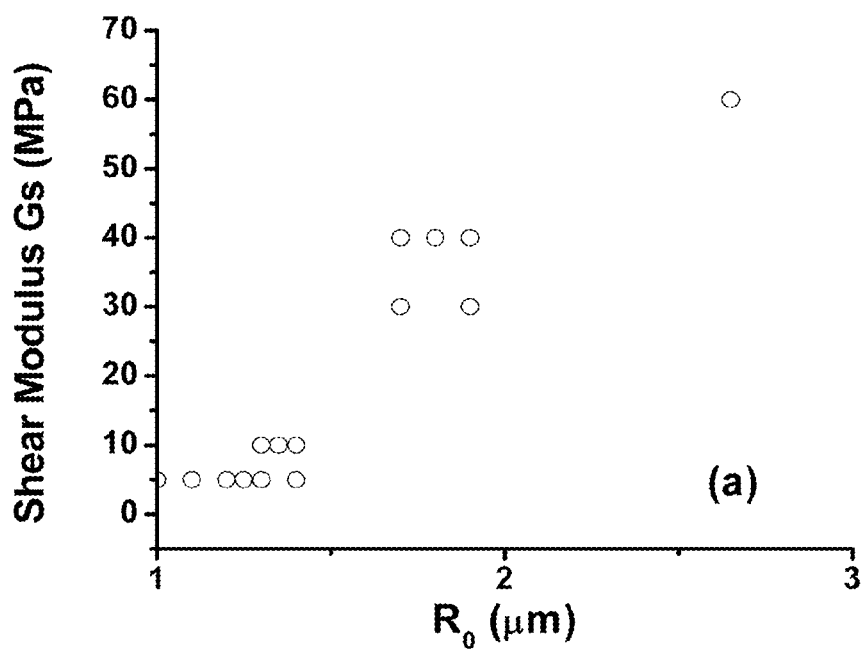
Figure 24:
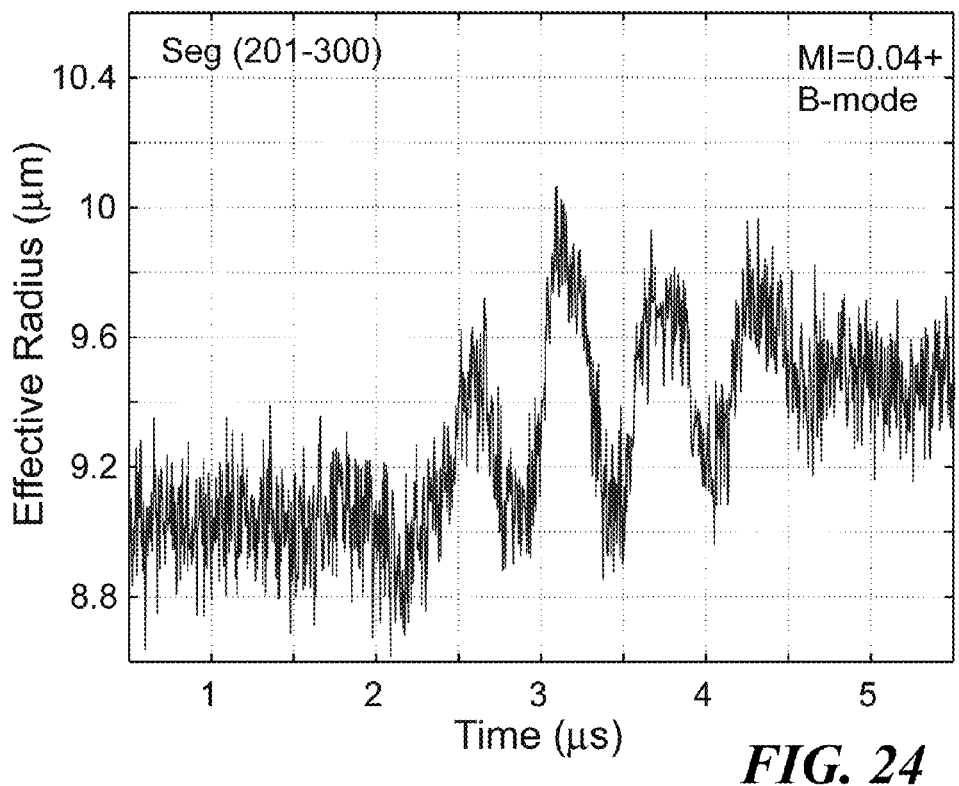
Figure 25A:
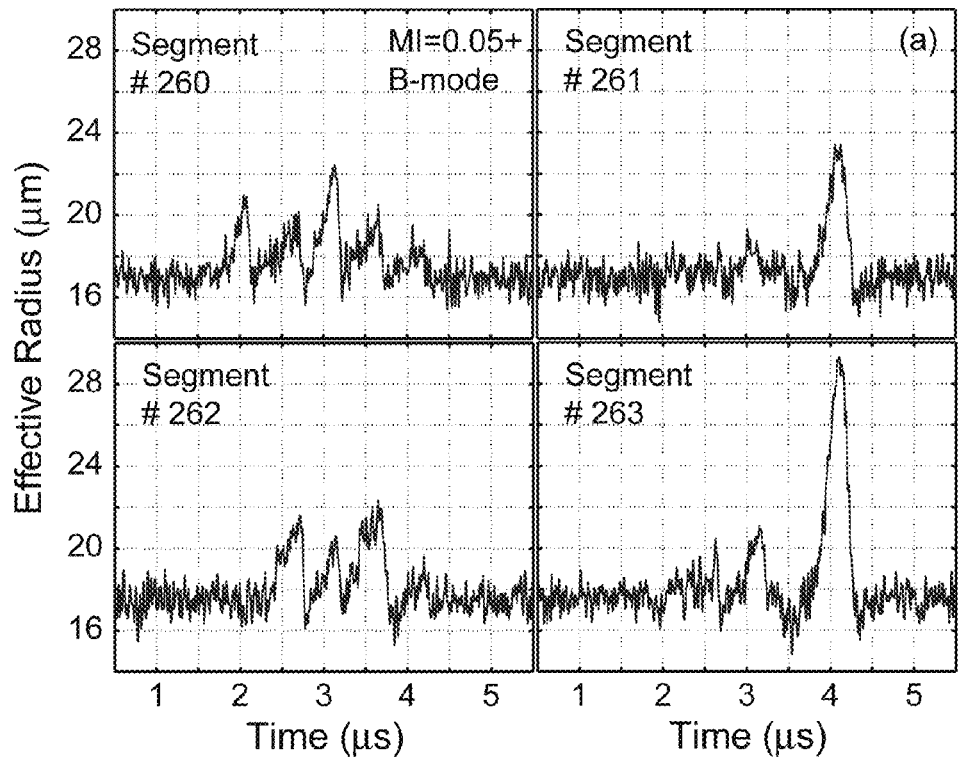
Figure 25B:
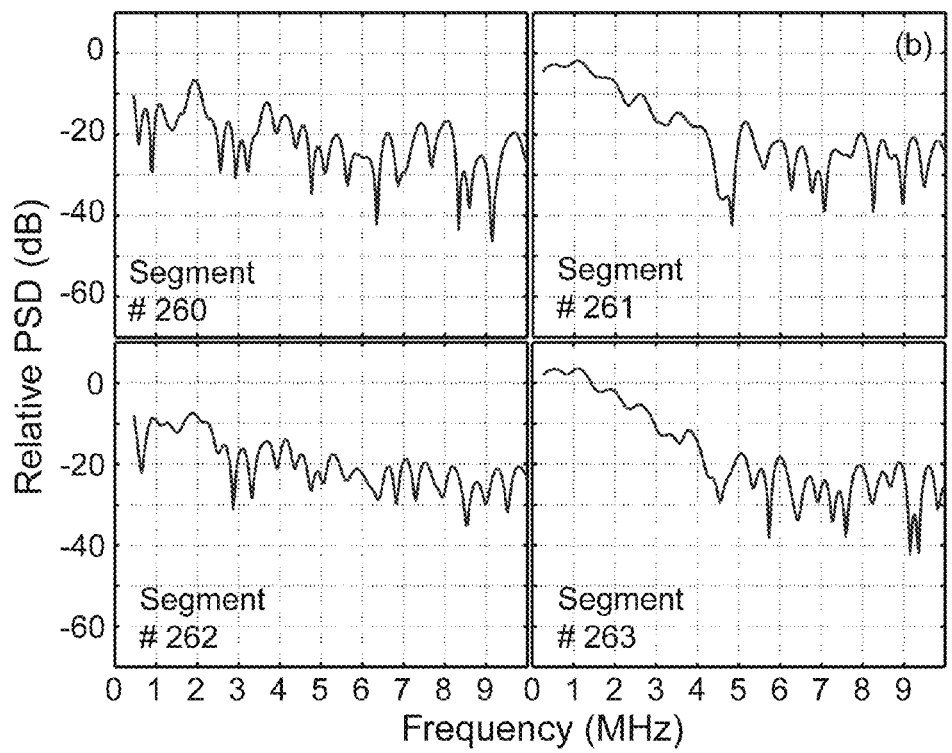
Figure 27:
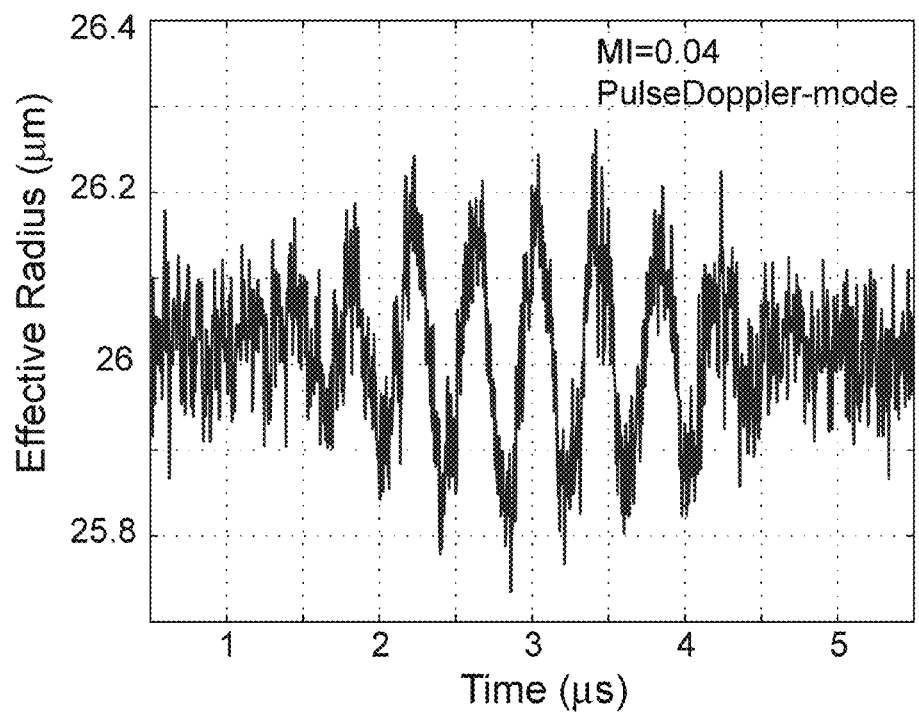
Figure 29:
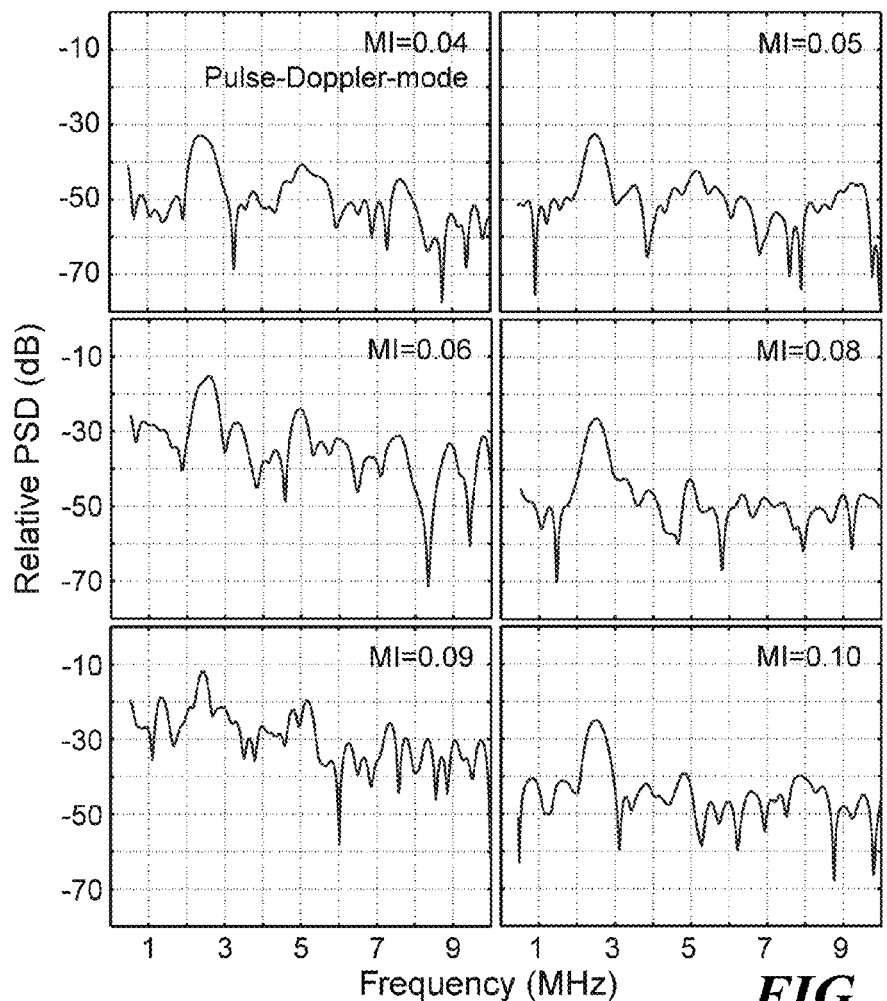
Figure 30A:
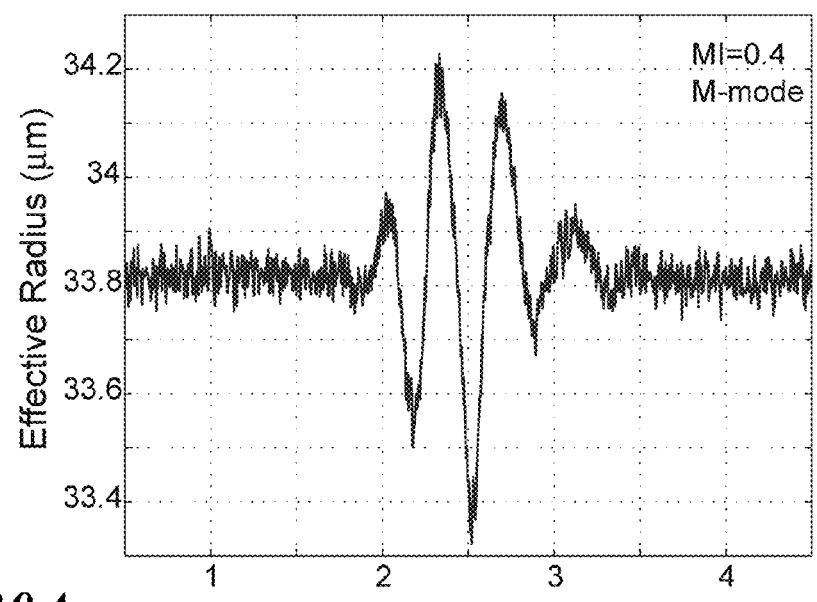
Figure 30B:
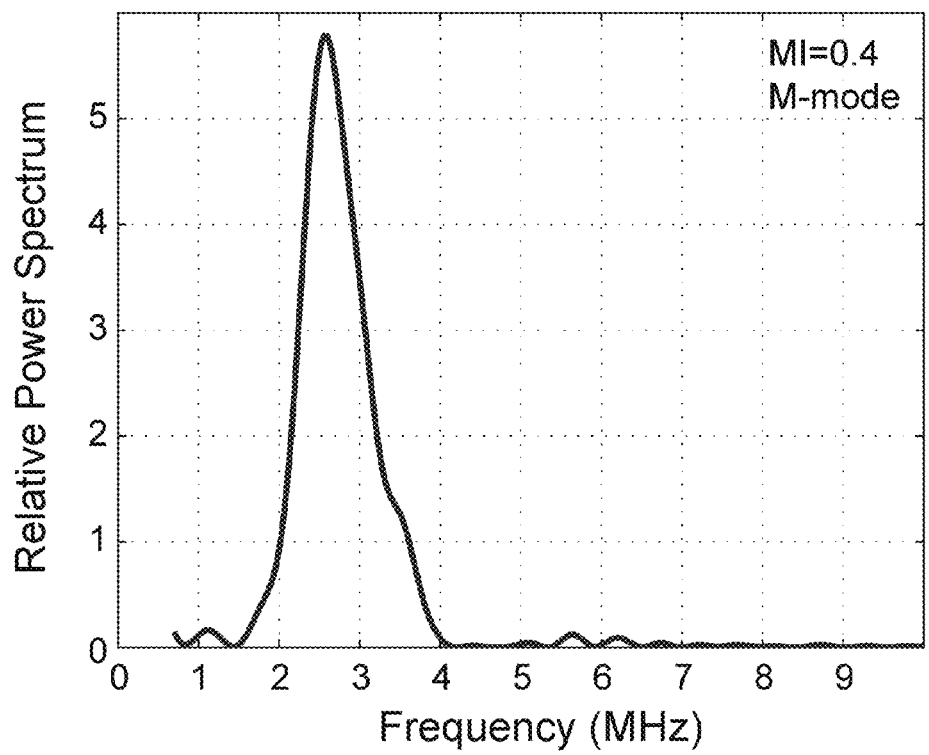
Figure 30C:
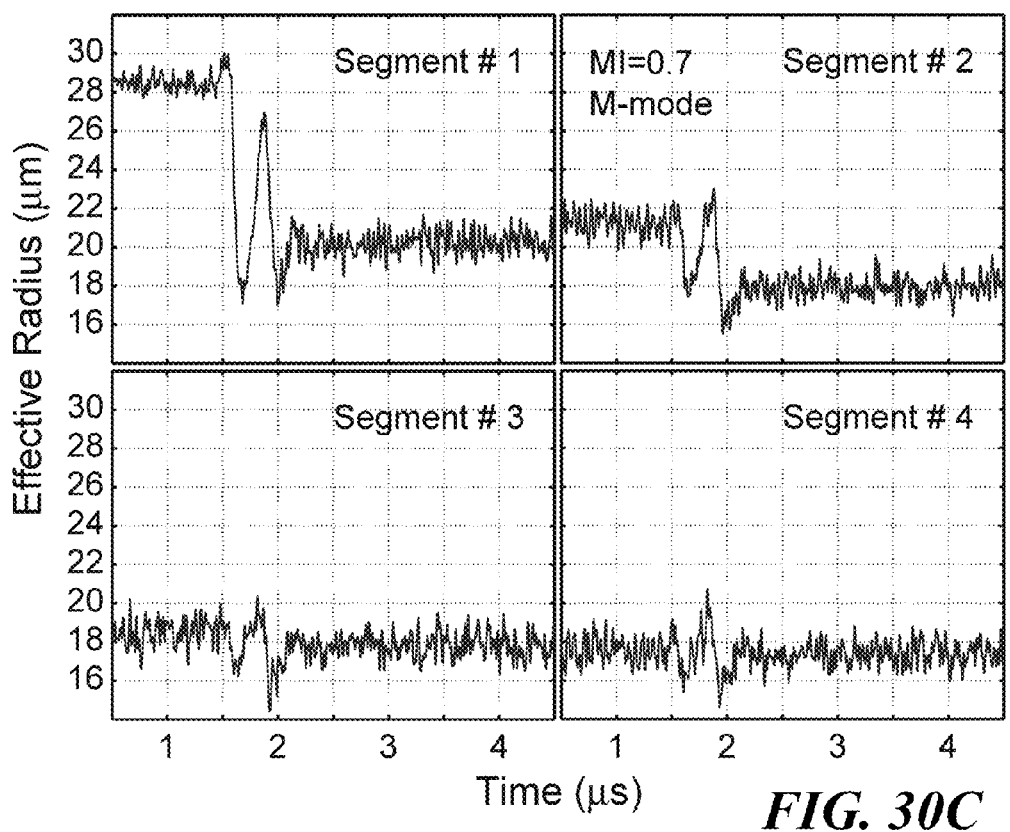
Figure 33A:
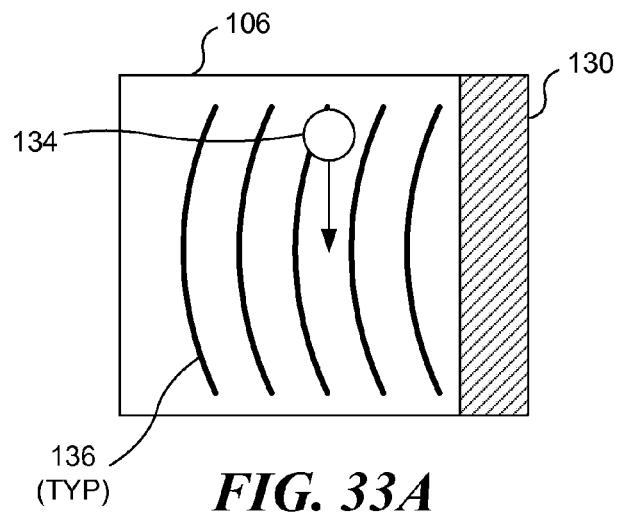
Figure 33B:
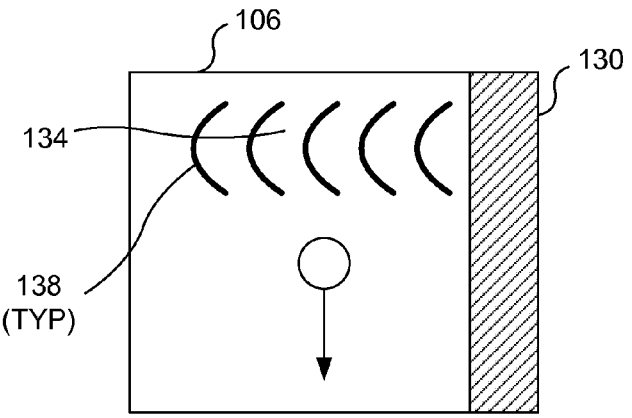
Figure 33C:
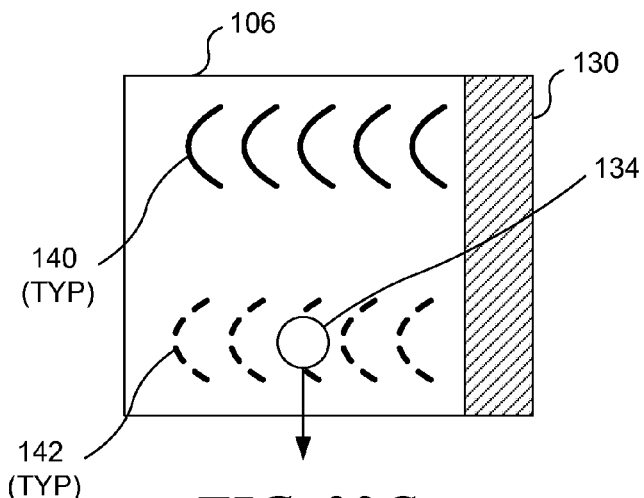
Figure 34A:
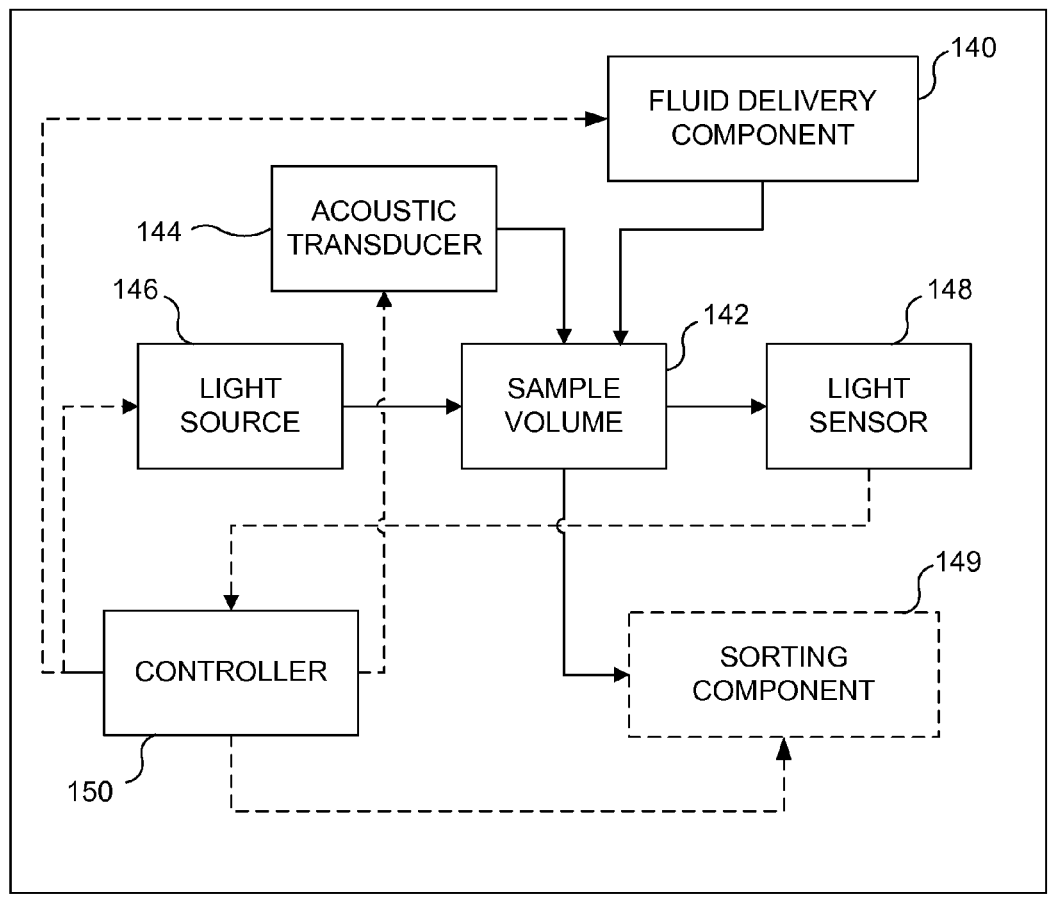
Figure 34B:
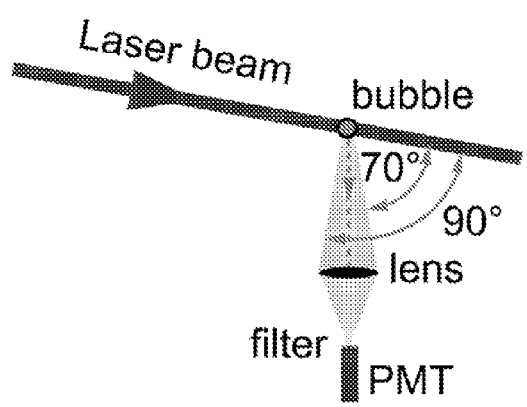
Figure 35A:
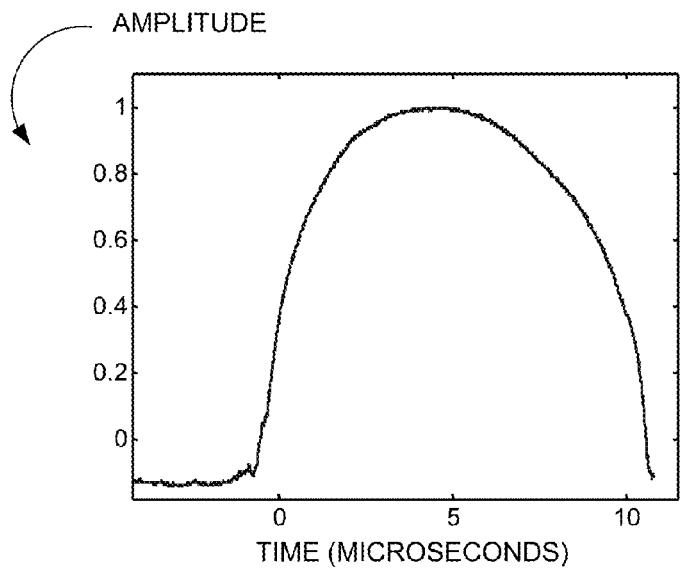
Figure 35B:
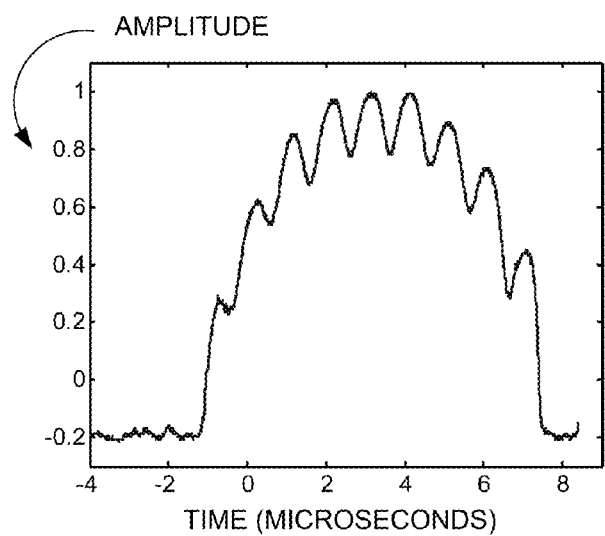
Figure 35C:
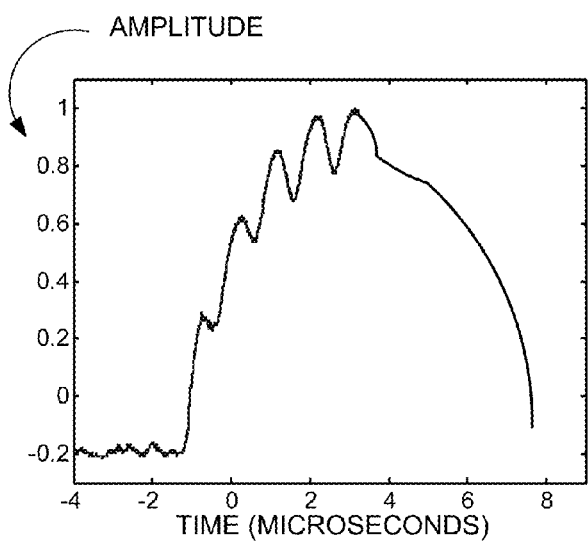
Figure 35D:
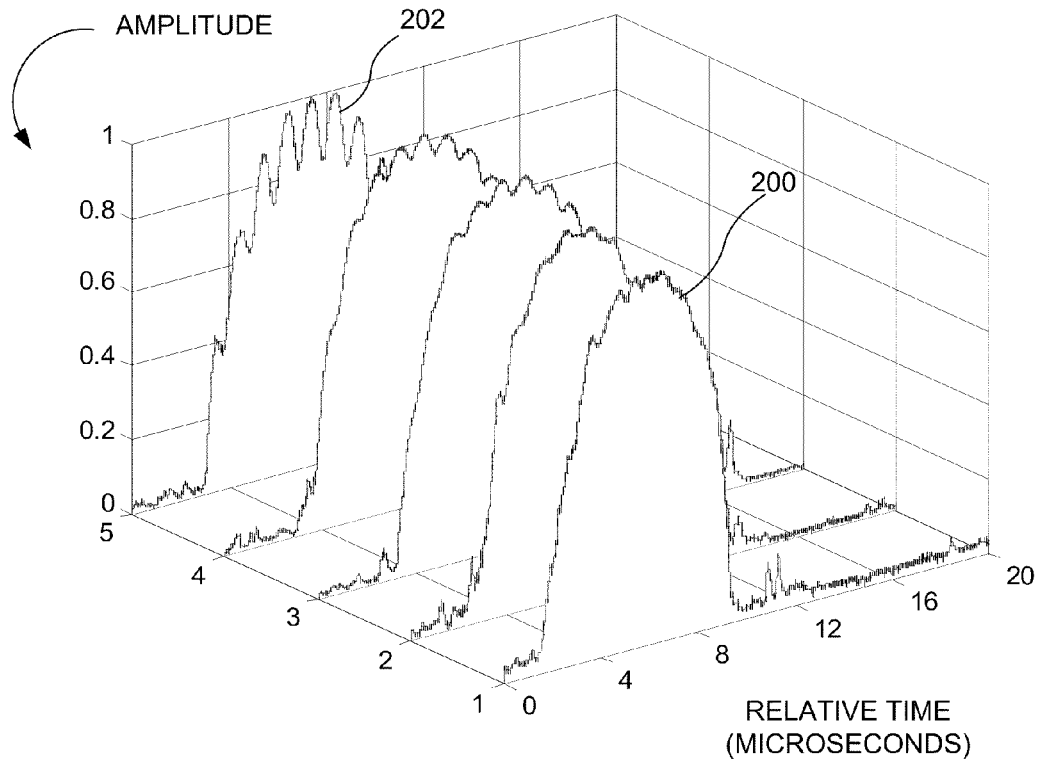
Figure 36:
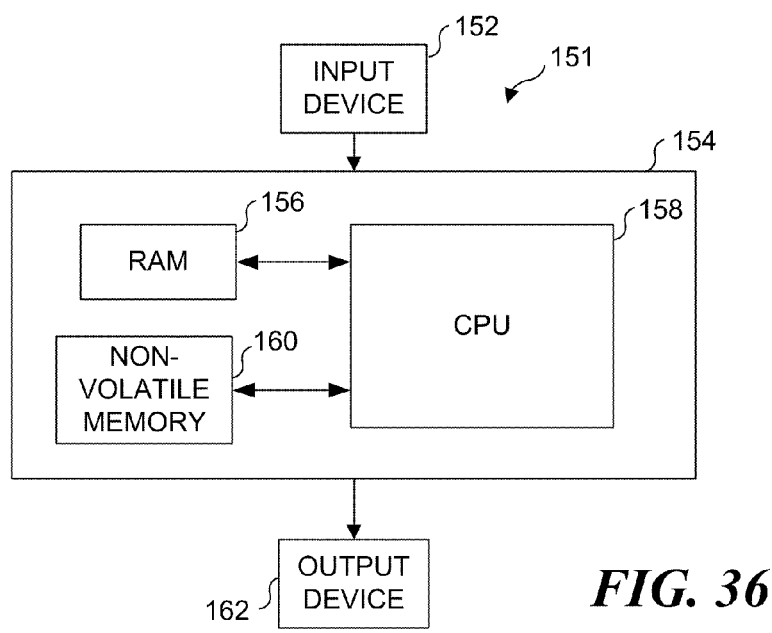

FIGS. 18A-18C graphically illustrate results provided by three different dynamic models, with varying parameters;

FIGS. 19A (showing measured driving pressure pulse) and 19B (showing measured bubble response and fits) graphically illustrate a comparison between the experimental data and simulated results, with a Sonovue™ bubble oscillating with a driving pressure amplitude of about 0.15 MPa;

FIG. 20A is a graph showing a change of a shell shear modulus as a function of radius;

FIG. 20B is a graph showing a change of a shell viscosity as a function of radius;

FIG. 21A graphically illustrates a typical effective RT curve of a group of UCA bubbles stimulated using B-Mode ultrasound;

FIG. 21B graphically illustrates the power spectrum corresponding to the data of FIG. 21A;

FIG. 21C graphically illustrates power spectrums collected from UCA bubbles collected at different times, using the same acoustic power settings;

FIG. 22 is a composite image graphically illustrating the power spectrum of UCA bubbles driven by different acoustic power settings using B-Mode ultrasound;

FIGS. 23A and 23B are composites images, with FIG. 23A including RT curves, and FIG. 23B including power spectrums, showing how bubbles dynamically evolve over several acoustic pulses;

FIG. 24 graphically illustrates data averaged over 100 consecutive pulses, showing dynamic changes to bubble size;

FIG. 25A includes RT curves of the same group of UCA bubbles during the consecutive insonification, showing their dynamic response to the acoustic pulse;

FIG. 25B shows power spectrums corresponding to the data of FIG. 25A;

FIG. 26A graphically illustrates an RT curve;

FIG. 26B graphically illustrates a power spectrum corresponding to the data of FIG. 26A;

FIG. 27 graphically illustrates a typical RT curve for a mass of UCA bubbles stimulated with Pulse-Doppler Mode ultrasound;

FIG. 28 graphically illustrates a power spectrum corresponding to the data of FIG. 27;

FIG. 29 is a composite image graphically illustrating the power spectrum of multiple UCA bubbles being driven by different acoustic powers (MI) in a Pulse-Doppler Mode;

FIG. 30A graphically illustrates a typical response from a mass of UCA bubbles stimulated by M-Mode ultrasound;

FIG. 30B graphically illustrates a power spectrum corresponding to the data of FIG. 30A;

FIG. 30C is a composite image that graphically illustrates consecutive effective RT curves of a mass of UCA bubbles responding to M-Mode stimulation;

FIG. 31 schematically illustrates an exemplary flow cytometer, modified by the addition of an acoustic transducer to direct an acoustic pulse toward a particle from which scattered light will be collected, to implement the concepts disclosed herein;

FIGS. 32A-C are plan views of exemplary flow cytometer sample volumes, showing the relative locations of the sample volume, an acoustic transducer to direct an acoustic pulse toward a particle from which scattered light will be collected, and a light source for illuminating the particle;

FIGS. 33A-33C are side views of an exemplary flow cytometer sample volume, schematically illustrating a particle moving through the sample volume while interacting with an acoustic pressure pulse in a variety of ways;

FIG. 34A is a functional block diagram of another exemplary flow cytometer system including an acoustic transducer to direct acoustic energy toward a particle, before or while light scattered by the particle is detected;

FIG. 34B schematically illustrates an exemplary relationship between a light source used to illuminate a particle in a sample volume, and a light collection system used to collect light scattered by the particle and direct that light to a sensor;

FIG. 35A graphically illustrates a static scattering intensity profile collected from a particle in a flow cytometer under constant pressure conditions;

FIGS. 35B and 35C graphically illustrate dynamic scattering intensity profiles collected from a particle in a flow cytometer under varying pressure conditions; and FIG. 35D graphically illustrates a plurality of dynamic scattering intensity spectrums, where each particle from which light is being collected is reacting to an applied pressure pulse or acoustic pulse;

FIG. 36 is a functional block diagram of a suitable computing environment for practicing the concepts disclosed herein.

DESCRIPTION

Figures and Disclosed Embodiments are Not Limiting

Exemplary embodiments are illustrated in referenced Figures of the drawings. It is intended that the embodiments and Figures disclosed herein are to be considered illustrative rather than restrictive. No limitation on the scope of the technology and of the claims that follow is to be imputed to the examples shown in the drawings and discussed herein.

As used herein and the claims that follow, it should be understood that the terms "UCA," "microbubble," and "encapsulated microbubble" have been used interchangeably. These terms refer to relatively small (on the order of microns in size) bubbles including a shell and a core. Shells are generally implemented using lipids, polymers, and/or albumin (although such materials are intended to be exemplary, rather than limiting), while cores are generally implemented using gases such as air, perfluoropropane (PFP), perfluorobutane (PFB), and octafluoropropane (OFP) (although such materials are intended to be exemplary, rather than limiting).

Figure 1:
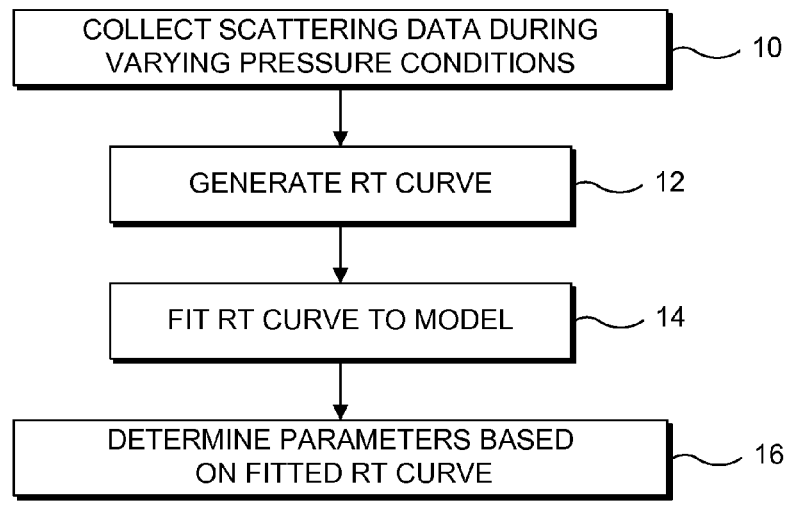

FIG. 1 schematically illustrates exemplary method steps for using scattered light to calculate one or more UCA parameters. The exemplary method steps include collecting light scattered from a UCA while the UCA is exposed to varying pressure conditions, as indicated by a block 10. An RT curve is generated based on the collected data, as indicated by a block 12, and the RT curve is fitted to one or more predefined models, as indicated by a block 14. The fitted curve is used to calculate one or more UCA parameters, as indicated in a block 16.

Figure 2:
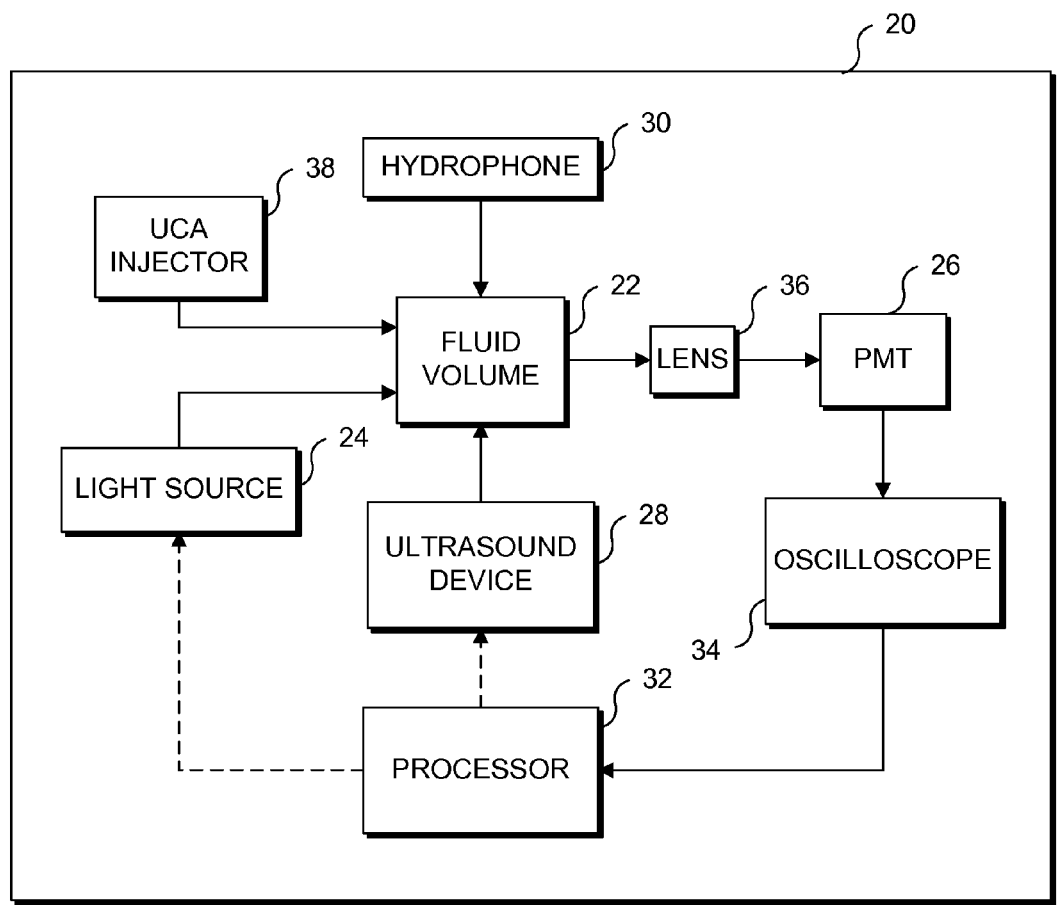

FIG. 2 schematically illustrates an exemplary system 20 for implementing the method steps of FIG. 1. System 20 includes a fluid volume 22 (for example, implemented using an optically transparent container, such as glass or plastic) into which the UCA can be introduced, a light source 24 for illuminating the UCA, a light sensitive detector 26 for collecting light scattered by the UCA, a pressure source for varying the pressure in the fluid volume (preferably implemented using an ultrasound probe/system 28), a sensor 30 for measuring actual pressure conditions, and a processor 32 for manipulating the collected data. In this exemplary embodiment, light source 24 is a laser, light sensitive detector 26 is a photomultiplier tube (PMT), sensor 30 is a hydrophone, and processor 32 is a computing device (an oscilloscope 34 can be used to manipulate the signal from the PMT before the data are processed by the computing device). Processor 32 is configured to generate an RT curve based on the collected data, to fit the curve to one or more pre-defined models, and to calculate one or more parameters based on the fitted RT curve. A lens 36 may (or may not) be used to direct light scattered by a UCA in the fluid volume toward the PMT. A UCA injector 38 (such as a syringe pump or pipette) is used to inject a UCA agent into the fluid volume. While not specifically shown in the Figure, a scattering angle from about 70 degrees to about 90 degrees is desirable, and the relative orientations of one or more of the injector, light source, and lens can be manipulated to achieve such a scattering angle. The laser light source employed in an empirical system was a red helium/neon (HeNe) laser, having a wavelength of 633 nm.

Various Figures provided herein graphically depict RT curves generated using light scattered by microbubbles. Such Figures often include both solid lines and dashed lines. Except where otherwise indicated, the solid line refers to empirically collected data, while the dashed line refers to fitted data. Those of ordinary skill in the art will readily recognize that many fitting algorithms and commercial fitting software programs are available. It should also be recognized that many different dynamic models describing microbubble are available, or may become available. Many variables in the model can be measured or estimated, to minimize the number of variables that are fitted. The unknown variables can be limited to shell parameters. Examples of variables that can be measured include pressure (e.g., as measured by the hydrophone) and bubble radius (which can be measured optically using a microscope or microscope and camera, or with light scattering while the bubble is static). Radius measurements for many UCAs are readily available in the published literature.

Having briefly discussed the exemplary method and apparatus, it will be useful to provide general information about light scattering and dynamic models describing the motion of microbubbles, so that the above noted concepts are understood in context.

Figure 3A:
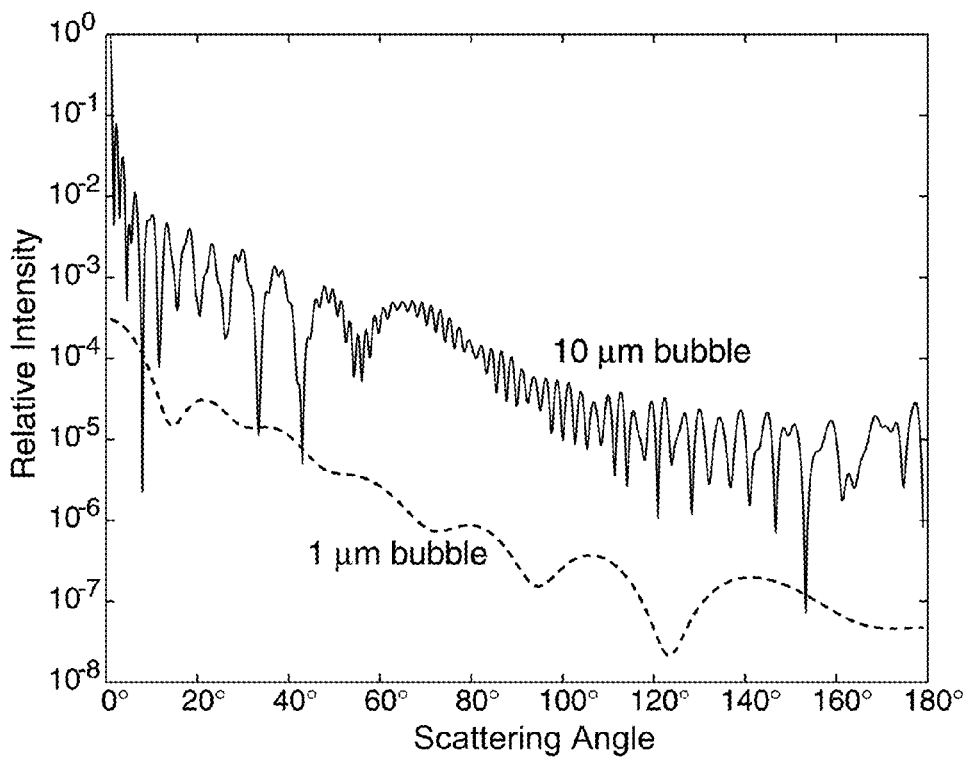
Figure 3B:
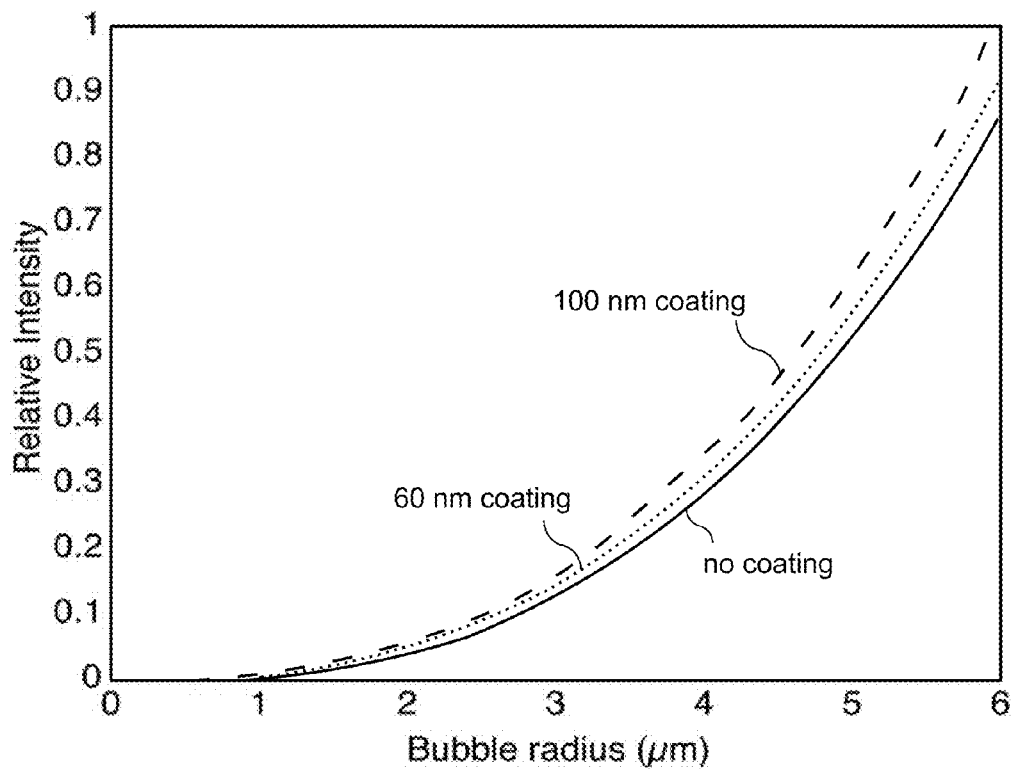

The Mie theory describes light scattering from homogeneous spheres (or bubbles, in the context of the current disclosure) in a homogeneous environment. In general, this theory indicates that the intensity of scattered light depends strongly on the observation angle. For an air bubble in water, and for a single light detector, the observation angle should be near the critical angle (about 83 degrees) from forward scattering. This preference is based on a physical-optics approximation, which suggests that the scattered light intensity is a monotonic function of bubble size. Calculations and empirical data have indicated the presence of relatively thin shells (i.e., on the order of 10-15 nm), which does not substantially change the relationship between scattering intensity and scattering angle (graphically illustrated in FIG. 3A, where the dashed lines represented thin shell bubbles and the solid lines representing bubbles without shells are nearly indistinguishable), indicating the Mie theory can be usefully applied to UCA (which are not homogenous spheres), as well as to homogeneous spheres. Significantly, the Mie theory also establishes a monotonic relationship between sphere/bubble size and scattered light intensity (larger bubbles result in an increase in the intensity of the scattered light), as indicated in FIG. 3B. Because of the relationship indicated in FIG. 3B, it is straightforward to convert scattered light intensity into a radius. Significantly, even if the calculated radius varies from the actual radius, the relative differences between radii calculated based on different measured scattered light intensities can still be quite useful in generating the RT curve discussed above, which once fitted to a selected dynamic bubble model, enables calculation of UCA parameters to be carried out, generally as discussed above.

With respect to the system of FIG. 2, it is important to recognize that the detector collects light from a finite angular distribution, not just at a single angle (the lens being employed to increase the light intensity onto the detector). Preferably, the angular span ranges from approximately 70° to 90°. The curve in FIG. 3B shows the relative integrated intensity over this span as a function of bubble size.

As noted above, the use of dynamic models of UCA bubbles is an important aspect to the concepts disclosed herein. Fortunately, there are many models from which to choose, and empirical evidence suggests that the concepts disclosed herein can be used with many of these models. There are several approaches for modeling a coated bubble, many of which are based on the RPNNP equation, which describes the response of a spherical bubble to a time-varying pressure field (including acoustic pressure) in an incompressible liquid:

$$\rho_L R \ddot{R} + \frac{3}{2}\rho_L \dot{R}^2 = P_g\left(\frac{R_0}{R}\right)^{3\gamma} + P_v - P_0 - \frac{2\sigma}{R} - \delta\omega\rho_L R\dot{R} - P_a\cos(\omega t) \quad (1)$$

where $R_0$ is the initial bubble radius, $\rho_L$ is the density of a Newtonian liquid, $P_0$ is the ambient pressure, $P_v$ is the vapor pressure, $\sigma$ is the surface tension, $\gamma$ is the polytropic exponent of the gas, $\delta$ is the damping coefficient, $P_a$ is the amplitude of the incident acoustic pressure, $\omega$ is the angular frequency of driving signal, and $P_g$ is the gas pressure inside the bubble ($P_g = P_0 - P_v + 2\sigma/R_0$).

The assumptions for Eq. (1) include following: (1) the motion of the bubble is symmetric; (2) the wavelength of ultrasound is much larger than the bubble radius; (3) no rectified diffusion occurs; and, (4) the bubble contains gas or vapor, which is compressed and behaves according to the gas law, with the polytropic parameter held constant.

De Jong's model, Church's model, Hoff's model, and Sarkar's model, discussed in greater detail below, are each modified from the general PRNNP equation. The choice of which bubble dynamics model is employed is not based on the relative accuracy of any particular model. It should be recognized that these models should not be considered restrictive; as new models that may be developed can also be employed.

Initial work in developing the concepts disclosed herein employed a simplified model that has previously been used in comparisons with high-speed camera images of encapsulated microbubble dynamics, the Morgan et al model. A major advantage in the Morgan model is that it has a reduced set of fitting parameters. The Morgan model is:

$$\rho R\ddot{R} + \frac{3}{2}\rho \dot{R}^2 = \quad (2)$$

$$\left(P_0 + \frac{2\sigma}{R_0} + \frac{2\chi}{R_0}\right)\left(\frac{R_0}{R}\right)^{3\gamma}\left(1 - 3\frac{\dot{R}}{c}\right) - \frac{4\mu\dot{R}}{R} - \frac{2\sigma}{R}\left(1 - \frac{\dot{R}}{c}\right) -$$

$$\frac{2\chi}{R}\left(\frac{R_0}{R}\right)^2\left(1 - 3\frac{\dot{R}}{c}\right) - 12\varepsilon\mu_{sh}\frac{\dot{R}}{R(R-\varepsilon)} - (P_0 + P_{drive}(t))$$

where R is radius of the bubble, $R_0$ is initial radius of the bubble, $P_0 = 1.01 \times 10^5$ Pa is the ambient pressure, $P_{drive}(t)$ is the acoustic driving pressure, $p=1000$ kg/m$^3$ is the liquid density, $\gamma \approx 1$ is the ratio of specific heats, $c=1500$ m/s is the sound speed in the liquid, $\sigma=0.05$ 1 N/m$^2$ is the surface tension coefficient, $\chi=0$ is the shell elasticity, $\mu=0.001$ Pa s is fluid shear viscosity, $\mu_{sh}$ is the UCA shell shear viscosity, and $\varepsilon$ is the UCA shell thickness.

Using Eq. (2), the relevant parameter space was examined to determine the relationship between the various parameters, which was done in order to determine if a fit to the data would be unique. For UCAs, this parameter space covers $0.1 \leq R_0 \leq 6$ mm, $0 \leq \varepsilon\mu_{sh} \leq 8$ nm Pa s, and $0.0235 \leq P_{drive}(t) \leq 1.2$ MPa (peak negative), relevant for thin shelled agents. Because isothermal behavior is assumed, the elasticity terms cancel. Assuming $R \gg \varepsilon$ (also assumed by Morgan in developing the model), the only term with shell parameters is given by $12\varepsilon\mu_{sh}\dot{R}/R^2$. Hence, the shell parameter can be referred to as the product $\varepsilon\mu_{sh}$. Note that there are initially three unknowns: $R_0$, $P_{drive}(t)$, and the product $\varepsilon\mu_{sh}$.

Referring to the driving pressure $P_{drive}(t)$, a calibrated needle hydrophone (the sensor in FIG. 2) can be used to measure acoustic driving pressure, as an input to the Morgan bubble dynamics model, thereby decreasing the unknowns by one. Most of the initially collected empirical data was obtained from the M-Mode of a diagnostic ultrasound system (the ATL Ultramark 4Plus™). Empirical data indicate the acoustic driving pressure of the selected ultrasound system falls well within the above-noted parameter space for the driving pressure.

Figure 4A:
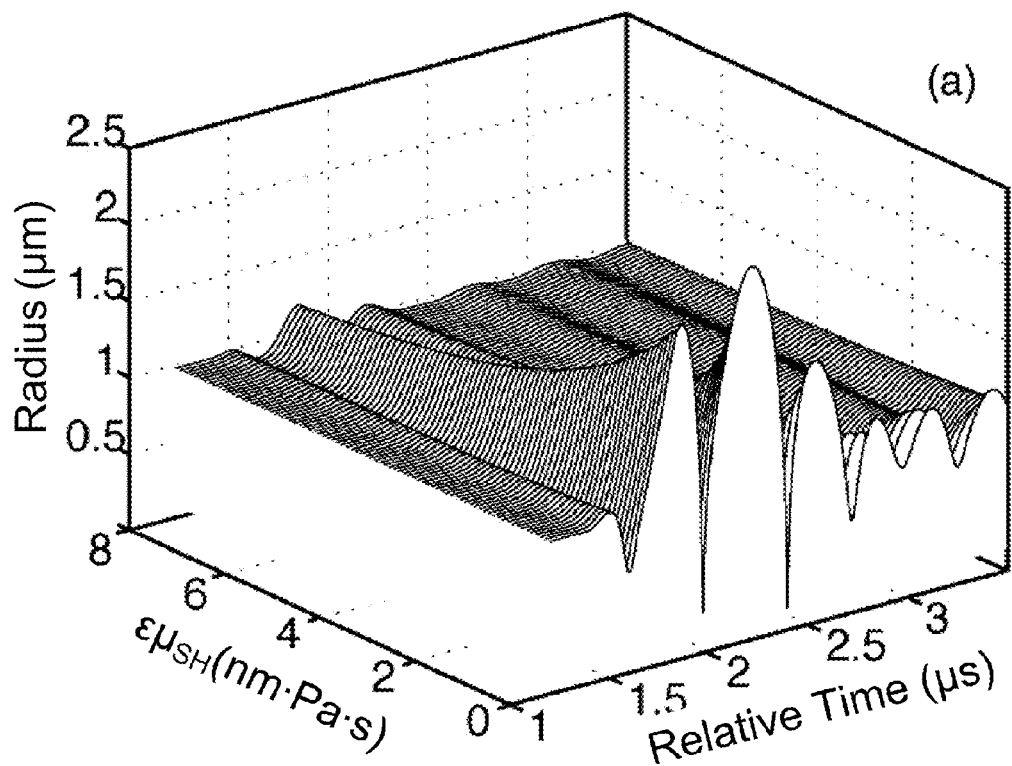
Figure 4B:
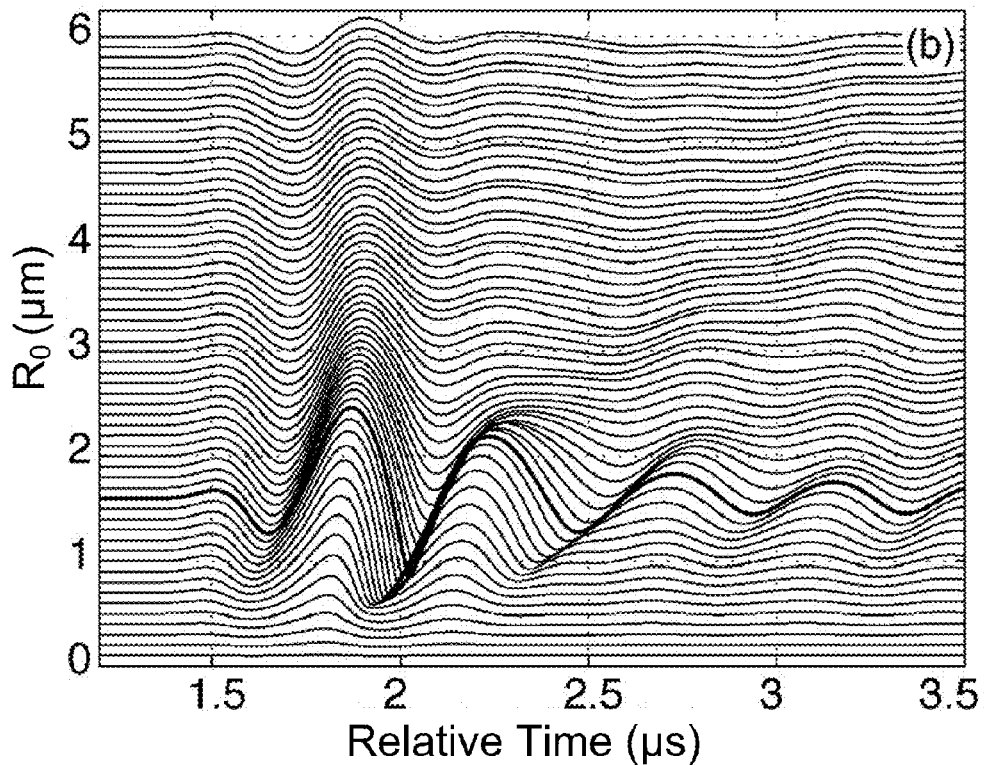
Figure 4C:
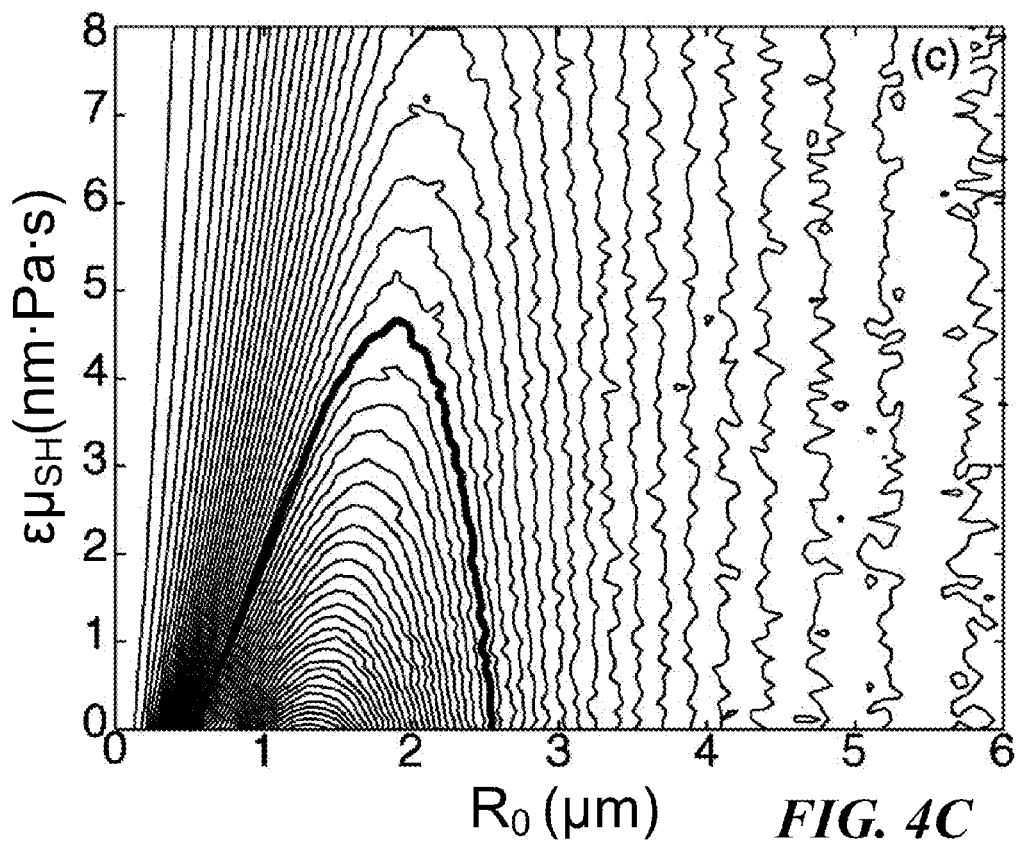

The remaining parameters are $R_0$ and the product $\varepsilon\mu_{sh}$. Significantly, examining the parameter space is necessary in order to ensure that the empirically fitted data will be unique. FIG. 4A graphically illustrates a simulation for microbubbles with a varying shell parameter, for an initial bubble radius size of $R_0=1$ μm, and $P_{drive}(t)=235$ kPa peak negative pressure. FIG. 4B graphically illustrates a waterfall plot of the simulated response curve R(t) for various initial bubble sizes and a fixed shell parameter (same drive amplitude). The resonant bubble size is darkened. FIG. 4C graphically illustrates a simulation contour map of $(R_{max}-R_0)$ vs. $R_0$ and $\varepsilon\mu_{sh}$ (with the same drive amplitude). Finally, FIG. 4D graphically illustrates the peak in the power spectral density (the main frequency component) of the simulation in FIG. 4A. Significantly, the resonant bubble size can be seen in FIG. 4B, where the curves appear to bunch together. As expected, the response curve R(t) has significant fluctuations near resonance. In FIG. 4C, the resonant bubble size increases with increasing shell parameter, from about 1.3 μm to about 2.1 μm, which is an expected behavior, consistent with the thin shell behaving as a damping mechanism. That is, an increase in damping results in a decrease in resonant frequency, or, equivalently, an increase in resonant size. FIG. 4C also shows that near resonance, there is a strong dependence on the shell parameter (when moving from contour to contour). However, for bubbles larger than about 3 µm, the dependence is weak at best (note the vertical contour lines). Thus, for larger UCAs, this model would not be useful for fitting shell parameters to the data.

Furthermore, the maximum amplitudes of the two main peaks in FIG. 4A change relative to each other as the shell parameter increases. The first peak, initially smaller than the second peak, becomes the larger peak for $\epsilon\mu_{sh}$>0.0.4 nm Pa s, which is most probably a consequence of the specific pressure pulse used. That is, the pressure pulse has two resonant peaks, near 2.3 MHz and 3.2 MHz. Because the resonance size depends on the shell parameter, as the shell parameter increases, it is possible that first one, and then the other of these resonances are manifest, resulting in a change in the bubble response.

Figure 4D:
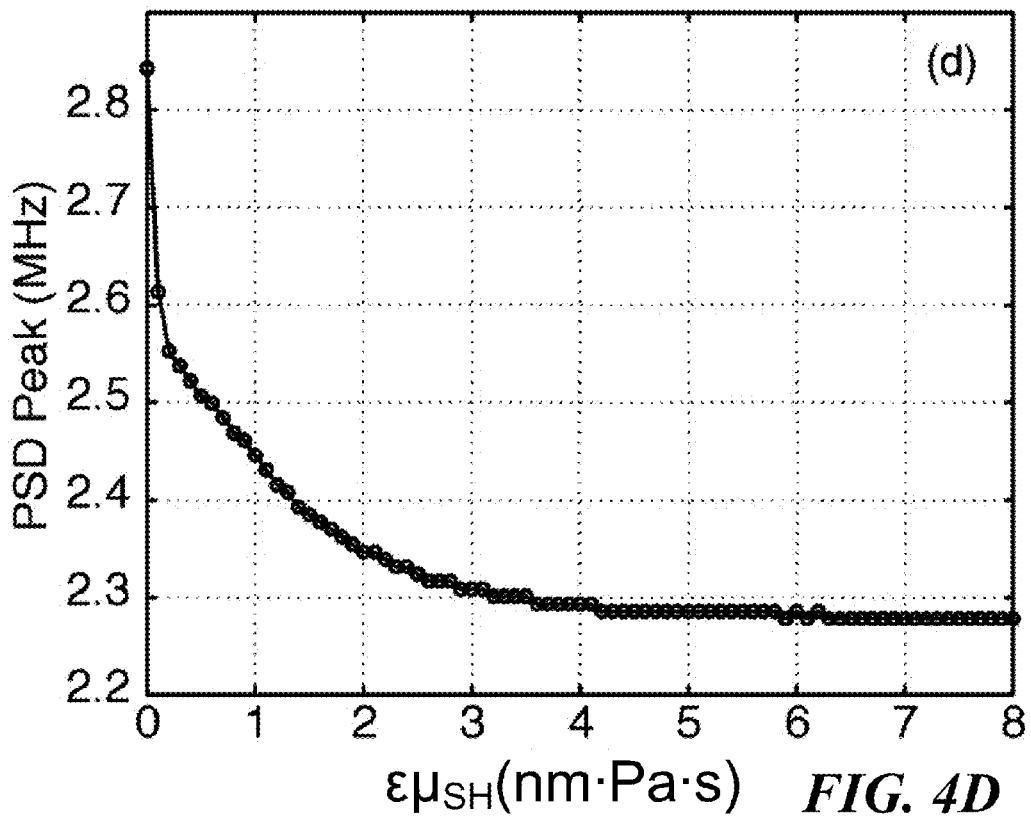

The power spectral density (PSD) for the example of FIG. 4A is shown in FIG. 4D. The peak in the PSD decreases with increasing shell parameter, but levels off quickly. It would be difficult to distinguish between two bubbles with different shell parameters, for $\epsilon\mu_{sh}$>3 nm Pa s, using only the PSD; however, the PSD might be used to determine when the shell breaks. The PSD is the frequency response of the system driven by the measured pressure pulse, and thus, includes the spectral characteristics of the driving pulse. It is nevertheless instructive to compare it to the bubble's resonance frequency, obtained from linearizing the equation of motion, setting $R \rightarrow R_0(1+\epsilon)$, expanding relevant terms in a binomial expansion, and neglecting second-order and higher terms. This leads to the frequency of oscillation, $f_r$, as follows:

$$f_r = \frac{1}{2\pi}\sqrt{\frac{3\gamma}{\rho R_0^2}\left(P_0 + \frac{2\sigma}{R_0} + \frac{2\chi}{R_0}\right) - \frac{2\sigma + 6\chi}{\rho R_0^3} - \frac{(4\mu + 12\epsilon\mu_{sh}/R_0)^2}{\rho^2 R_0^4}} \quad (3)$$

Using the parameters above ($R_0$=1 µm, $\gamma$=1), and considering the undamped case ($\epsilon\mu_{sh}$=$\mu$=0), the linear resonance frequency, $f_r$, is approximately 3.5 MHz. The frequency of oscillation does not follow the PSD curve (because the PSD includes the driving pulse spectral characteristics). Instead, it drops quickly to zero near $\epsilon\mu_{sh}$=1.6 nm Pa s (for a 1 µm bubble), which appears to imply that smaller bubbles are over damped and do not resonate.

The discussion above has been limited to resonances and the relationship with a particular pressure pulse. However, the most important reason for mapping the parameter space is to determine if a solution is unique, because as mentioned above, there are two unknown parameters to be fitted, namely $R_O$ and the product $\epsilon\mu_{sh}$. To help solve this problem, it is helpful to focus on FIG. 4C (the contours of ($R_{max}$-$R_O$) vs. $R_O$ and $\epsilon\mu_{sh}$), bearing in mind that the pressure amplitude has been measured, which constrains the analysis to the amplitude of R(t).

If $R_O$>3 µm, the quantity ($R_{max}$-$R_O$) is not as sensitive to the shell parameter, making unique fits difficult. Fortunately, with UCAs, the majority of bubbles are in the size range from about $R_O$=1 µm to about 2.5 µm. In this range, the contours show sensitive dependences (note the darkened contour line in FIG. 4C). If product $\epsilon\mu_{sh}$ is initially set to 2 nm Pa s, there will be two possible solutions for $R_O$ that would result in the same ($R_{max}$-$R_O$) value, near 1 µm and 2.4 µm. However, $R_{max}$ itself is different for these two values. For example, if the condition $R_O$=1 µm is chosen, then $R_{max}$=1.6 µm, and if $R_O$=2.4 µm, then $R_{max}$=3.0 µm. The empirical data will constrain the results to only one of these values. In conclusion, although the above discussion leads to a two-parameter fit, the data constrain the solutions to a single parameter. In this model, the shell parameter is not important for larger bubbles, but for microbubbles of interest, it is a sensitive parameter; thus, the task of uniquely fitting the data to the model is feasible.

The following empirical study employed a system generally consistent with that shown in FIG. 2. The study involved injecting individual microbubbles into a region of interest, insonifying the microbubble with ultrasound, and collecting light scattered from the microbubble. The region of interest is the small volume of liquid where the ultrasound and laser illumination intersect a microbubble. For most studies, the liquid was filtered (0.2 µm porosity) and de-ionized (having >18 MΩ resistance) water.

Two methods were used to inject UCAs into the region of interest. Most often, a highly-diluted UCA solution (calculated to be on the order of $10^5$/ml) was injected into a rectangular water tank (3.5 cm² cross section, filled to a height of about 4 cm) with a syringe pump (at a rate of 10 ml/h) with a 0.5 mm inner-diameter tube. The ejection of the microbubble was approximately one-half cm from the laser beam path. Based on the numbers given above, it might be expected that subsequent bubbles would generate a scattering "event" about every 3 ms. However, the actual frequency of events was much less (approximately one event over several seconds). The most likely reason for this phenomenon is due to UCA congregation within the syringe, and at curves in the tubing, especially where the tubing goes up and over a lip. Also, bubbles ejected from the tip may move away from the laser beam, and not into it.

To verify that the measured response curves were for single microbubbles, UCAs were injected manually into the water-filled vessel that contained a small amount of a water soluble gum (e.g., xanthan gum). The xanthan gum increased the viscosity of the liquid slightly, so that after injection, the microbubble came to rest and remained relatively stationary. The microbubble was then imaged with a back-lit LED, microscope, and CCD camera to verify that there was indeed a single bubble in the region of interest. The fluid vessel was then repositioned so that the bubble was at the center of the laser beam/ultrasound probe focus. Empirical data indicate that there was no major difference in measurements between experiments conducted in water and the xanthan gum mixtures, except that the added xanthan gum yielded higher noise levels.

The xanthan gum gel preparation was performed as follows: 2.6 grams BT food grade xanthan gum powder, 12 g glycol, and 600 g water (slightly degassed) were combined. First, the powder and glycol were mixed and poured into a beaker, and the water was then poured into the beaker very slowly over a stick to minimize the trapping of bubbles. The mixture was stirred slowly for up to an hour using a magnetic stir bar to make it homogeneous. The gel was finally poured slowly into the experimentation vessel. Because of the possibilities of contamination and bacterial growth, a new gel was made prior to the start of each experiment. If more viscous gels are used, removing trapped bubbles becomes much more difficult and requires centrifuging the solution for up to 3 hours.

In the empirical study, a 30 mW HeNe laser was employed as the light source to illuminate the microbubbles. With a lens, the beam waist at the region of interest (i.e., where the microbubble, the laser beam, and the ultrasound intersect)

was focused to less than 100 μm (although, because some scattering occurs through the plastic water tank and through the water, it is difficult to accurately measure the beam waist). The light scattered from the bubble was then focused with a 5 cm lens onto a PMT detector (Hamamatsu, Model 2027™). The main function of the collecting lens was to increase the signal/noise (covering the angles 70°-90°). The PMT was biased at 21000 V. A HeNe line filter was placed against the PMT cathode window to block other sources of light. The output of the PMT was conveyed directly to a high-speed digital oscilloscope (LeCroy), and then to a personal computer for post-processing. As noted above, the varying pressure conditions were supplied using an imaging ultrasound probe (placed directly in the fluid vessel, although an externally disposed transducer can also be employed, so long as the fluid vessel wall is acoustically transparent).

Data collection was performed in a sequence mode, where high-resolution data files are collected during each ultrasound pulse. The total data collected are limited by the available memory of the oscilloscope. For the empirical study, data sequence records of 40 consecutive acoustic pulses were collected before transferring the file to the computing device. Each segment included a 5 ms long window, with a resolution of 4 ns. The segments were separated by about 1 ms (triggered by the source transducer). Appropriate delays in triggering were used to ensure that the bubble response was centered in the segment window.

The imaging ultrasound probe (the Ultramark 4Plus™) was operated in the M-Mode at about 1 kHz pulse repetition frequency (PRF). A calibrated needle hydrophone monitored the acoustic pressure. In actual experiments, the hydrophone was placed at an angle relative to the pulse. Thus, the relative angle between the transducer and hydrophone had to be measured, and then a separate water tank was used to determine the hydrophone response as a function of the angle of the ultrasound probe. This hydrophone response as a function of the angle, expressed as a multiplicative factor, was then used in all subsequent data analyses.

Other empirical studies employed a single element high intensity transducer, which was inserted through the bottom of the vessel, with the hydrophone being positioned directly above it, so that the angle problem described above was not an issue. For this configuration, relevant transducer parameters are center frequency f=1.8 MHz, focal length=63 mm, −6 dB for a bandwidth=500 kHz, 2.5 cm active area, 10 cycle bursts, and 10 kHz PRF.

FIGS. 5A-5B, 6A-6B, and 7A-7B graphically illustrate data and model fits for Optison™ and Sonazoid™ UCAs, in water and diluted aqueous xanthan gum gel. There are two important points to note. First, the light scattering model and data both produce an intensity versus time I(t) that must be converted to a radius versus time R(t). For the experimental data, the scattered intensity is found by subtracting the background intensity from the total intensity. The model generates a relative value, so a multiplicative scaling factor must be found to match the model to the data. Once the scaling factor is found, it is unchanged for all subsequent experiments. The relationship described above for FIG. 3B can be used to convert the relative intensity to a radius. A second point to note is that best fit studies were required in order to constrain the two unknowns ($R_0$ and the product $\epsilon\mu_{sh}$). As described above, the expected ranges for the parameters were defined. Within these ranges, it was determined that a deviation of about 65% in $R_0$ would generate a good fit. In addition, it was determined that shell parameter values published in the literature would enable good fits to be achieved. Therefore, for these studies the initial shell parameter for Optison™ was defined as $\epsilon\mu_{sh}$=6.0 nm Pa s, and for Sonazoid™, the initial shell parameter was defined as $\epsilon\mu_{sh}$=2.0 nm Pa s. Deviations of up to about +/31 1 nm Pa s also generated good fits. It was determined that UCA oscillations from pulse to pulse were relatively regular, so several pulses were grouped together to improve the SNR.

FIG. 5A graphically illustrates an RT curve generated using an Optison™ UCA pulsed with the Ultramark 4Plus™ in water, while FIG. 5B graphically illustrates an RT curve generated using an Optison™ UCA pulsed with the Ultramark 4Plus™ in the water/xanthan gum solution. For each RT, ten consecutive pulses (segments) were averaged together to increase the SNR. The measured peak negative pressure and fitted initial bubble radius are 210 kPa and 1.47 μm, respectively. For these parameters, the data and simulations exhibit quasi-linear motion. For these and other data, very good agreement with the major oscillations is obtained. The smaller ring-down oscillations are more difficult to fit because of the lower signal strength. Although the Morgan model discussed above is arguably not the most accurate model to use for encapsulated microbubbles, the overall good fit to the data suggests that the empirical data is indeed based on measuring the pulsations of individual encapsulated microbubbles. To provide verification that the light scattering was being performed on single bubbles, and/or that the bubbles were shelled, the experiments were repeated in the diluted aqueous/xanthan gum gel mixture. As noted above, the diluted gel mixture was sufficiently viscous to enable a UCA to be manually injected into the region of interest. The UCA could then be examined under a microscope to ensure that the agent in the region of interest was an individual microbubble (as opposed to a mass of microbubbles). Due to the viscosity of the solution, each UCA would remain in the region of interest for several minutes, indicating that the bubbles were shelled and stable. As can be seen in FIGS. 5A and 5B, diluted xanthan gum gel did not affect the dynamics adversely, and the fit is remarkably good. The measured peak negative pressure and fitted initial bubble radius, $R_0$, are 340 kPa and 1.5 μm, respectively. As with the previous data, these bubbles also exhibit nearly linear oscillations.

Figure 7A:
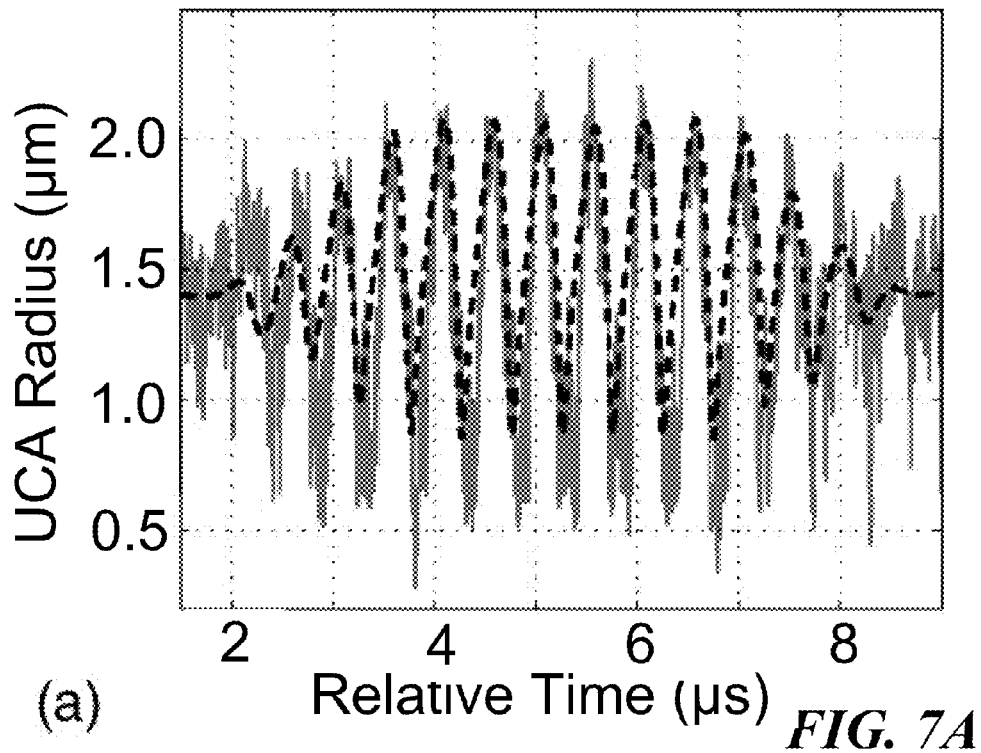
Figure 7B:
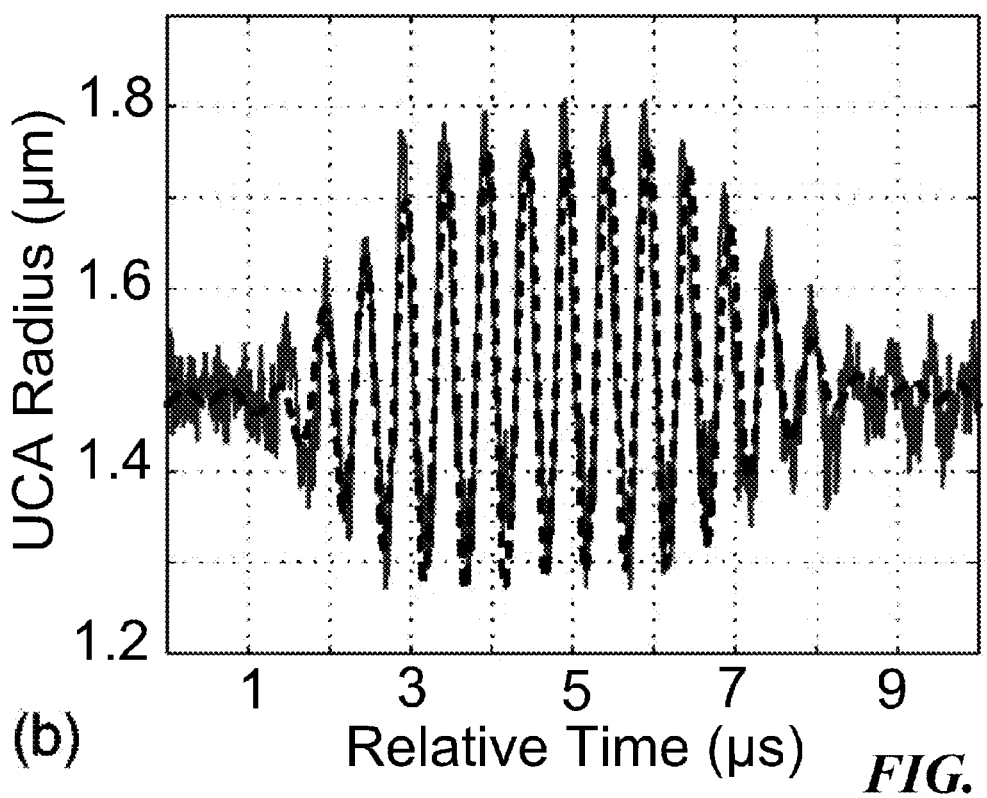

Sample response curves from a single element transducer (i.e., a transducer configured for therapeutic ultrasound rather than for imaging ultrasound) are shown in FIGS. 6A, 6B, 7A, and 7B. These experiments were performed both in water and aqueous xanthan gum gel mixtures. In FIG. 6A, (Optison™), data from a ten-cycle tone burst were averaged over 37 pulses. In FIG. 6B, (Optison™), data from a ten-cycle tone burst were averaged over 40 pulses. In FIG. 7A, (Sonazoid™), data from a ten-cycle tone burst were averaged over 5 pulses. In FIG. 7B, (Sonazoid™), data from a ten-cycle tone burst were averaged over 40 pulses. The measured peak negative pressures and fitted ambient bubble sizes are summarized in Table I (FIG. 8). The relatively poor SNR in FIG. 6A is likely due to the bubble not being in the center of the laser beam. Non-linear bubble oscillations were especially evident in FIGS. 6B and 7B, presumably due to the increased pressure amplitudes. Although these longer tone bursts are not very relevant to imaging applications (which utilize short diagnostic pulses), variable pulse lengths can be used to explore issues such as shell fatigue and microbubble stability.

The fitted ambient sizes (from Table I in FIG. 8) are consistent with known UCA bubble sizes. Based on FIGS. 5A-7B, it can be concluded that the good fit of the Morgan model to the experimental data, both in water and diluted gel, is evidence that light scattering can be beneficially employed in measuring individual UCA dynamics. Further experiments indicated that these techniques can also be applied to UCA clusters (i.e., masses of microbubbles), not just individual bubbles.

One of the advantages of the light scattering technique discussed above is its ability to make high temporal resolution measurements over long time scales. The following results are based on observations of UCA microbubbles subjected to consecutive pulses from the Ultramark 4Plus™. For slowly evolving microbubbles, the data were combined data for groups of ten pulses, while for quickly evolving microbubbles, the data were examined for each individual pulse.

When fitting the evolution data to the Morgan dynamic model, there is always the question of which of the two unknown parameters ($R_0$ and the product $\epsilon\mu_{sh}$) to change in order to obtain a good fit. Because the shell data that are collected might be compromised (e.g., from dislodging, or crumpling, or due to changes in permeability), varying the shell parameter (product $\epsilon\mu_{sh}$) was preferred.

Slowly Evolving Agents:

To follow the slow evolution of UCAs, the pressure amplitude employed was approximately 130 kPa. This pressure amplitude is lower than the fragmentation thresholds found in the literature for the UCAs utilized. The studies providing the thresholds were looking at relatively fast destruction mechanisms, not slow decay mechanisms. A more relevant comparison is likely to be the slow decay of backscattered signals for UCAs subjected to clinical ultrasound.

Figures 9A, 9B, 9C:
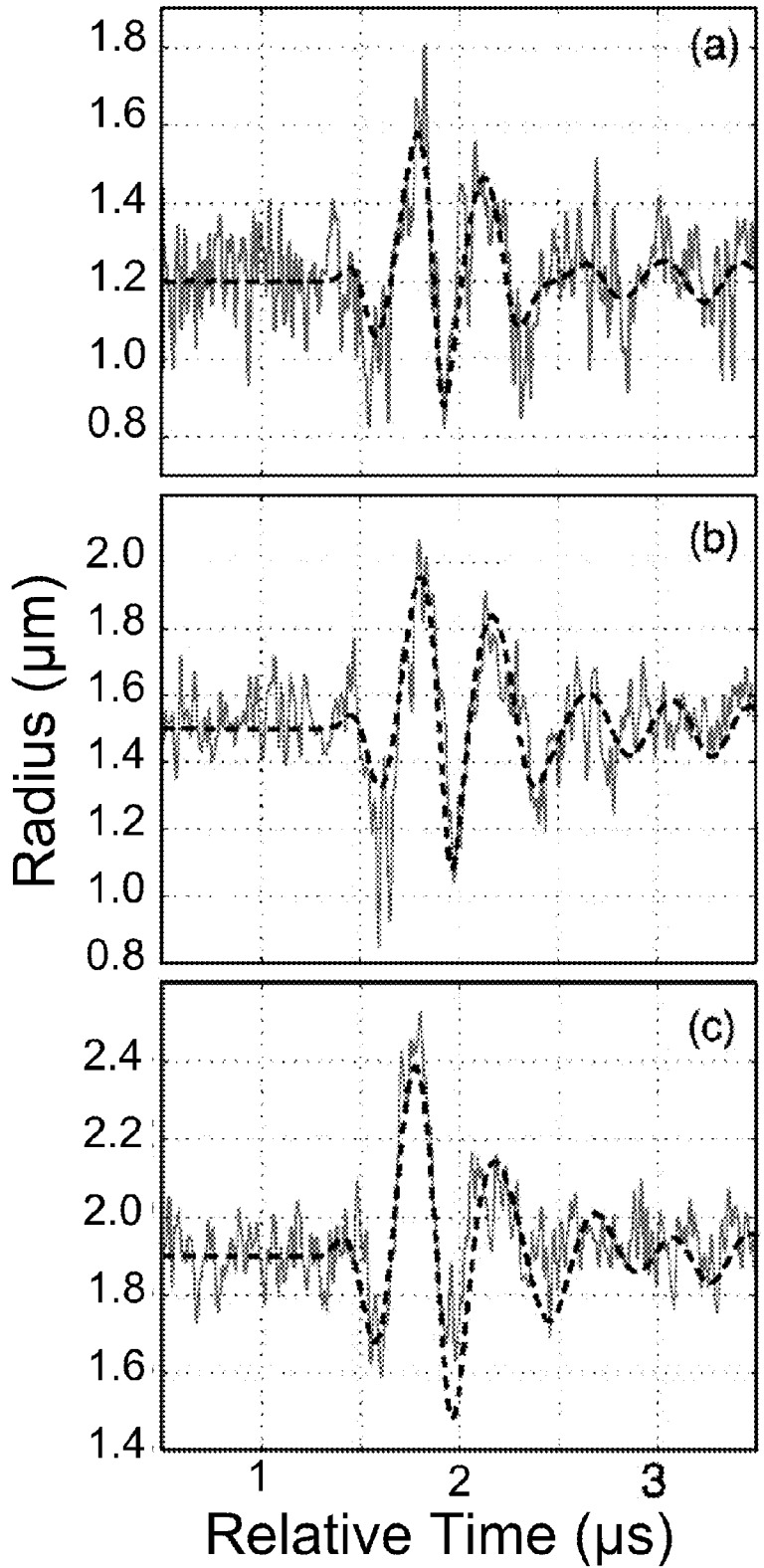

FIGS. 9A-9C graphically illustrate the slow evolution of a Sonazoid™ microbubble in water, collected in three successive groups of ten pulses. Significantly, a good fit was obtained without having to change the shell parameter; it was kept constant at 2.0 nm Pa s. However, $R_0$ was increased between groups (from 1.2 to 1.9 μm; see Table II in FIG. 10). That is, the Sonazoid™ microbubble appears to be growing with successive pulses. This slow growth phenomenon was not observed with Optison™ bubbles. Two physical interpretations can be made. First, the lipid shell may have been partially compromised before the experiment began. Although possible, this trend has been observed from many different datasets. Second, during expansion or compression, the lipid shell may alternatively become semi-permeable. If it is assumed that the bubble is filled initially with perfluorobutane (PFB) and the water contains air; then because of the higher diffusivity of air, diffusion of air into the bubble will occur at a faster rate than diffusion of PFB out of the bubble. Thus, at least initially, the bubble can grow. Again, it is emphasized that FIGS. 9A-9C show successive segments in one sequence of data. At about 1 ms between segments (equal to the burst PRF), the total elapsed time is about 30 ms.

A summary of the parameters for FIGS. 9A-9C is provided in Table II (FIG. 10). Previously reported data indicates that Sonazoid™ microbubbles dissolve after each pulse; however, such data were generated using about twice the pressure amplitude. It is likely that at those higher pressures, gas may be forced through the shell during compression.

Quickly Evolving Agents:

For this study, the pressure amplitude was increased to 340 kPa for Optison™ and 390 kPa for Sonazoid™. Previous studies report that the decay rate of the backscattered signal for Optison™ increased at these higher pressures, and that Sonazoid™ also showed a decay, although at a slower rate. Other studies indicate that these pressures are above the fragmentation threshold.

FIGS. 11A-11D graphically illustrate Optison™ response curves (i.e., RT curves) for individual (i.e., non-averaged) pressure pulses from the Ultramark 4Plus™ in the diluted aqueous/xanthan gum solution/gel. In FIGS. 11A-11C, the microbubble response comes from consecutive pulses. A single pulse is skipped, and then the data illustrated in FIG. 11D were collected. In terms of pulses, the Figures illustrate the dynamical response from pulses 1, 2, 3, and 5.

There appears to be a second series of oscillations developing in FIGS. 11B-11D. These signals may be due to the arrival of a second microbubble. Referring to the first major peak, in FIG. 11A the Morgan model corresponds to the data rather well. The fit is for a 1.5 μm radius bubble, with a shell parameter of 6.0 nm Pa s. In FIG. 11B, the fit is still acceptable; however, there are large amplitude "spikes" in the dataset. Such spikes were often observed immediately before, or during microbubble destruction, and may be related to a crumpling of the shell (shell crumpling has been previously observed). In FIGS. 11C and 11D, the model must be adjusted by decreasing the shell parameter (keeping the radius fixed). That is, the shell of the microbubble from which the scattered light was collected appears to be compromised. The parameters for this dataset are summarized in Table III (FIG. 12).

FIGS. 13A-13F graphically illustrate RT curves for optical scattering data collected from a Sonazoid™ bubble in water, while the bubble was undergoing an evolution during consecutive pulses (one pulse is not shown between the last two pulses, i.e., a pulse was skipped between the RT curves of FIGS. 13E and 13F). Referring to FIGS. 13A-13D, the shell parameter is fixed, but the ambient bubble radius was increased from 0.8 μm to 1.2 μm to maintain a good fit (i.e., to achieve the fit indicated by the dashed line). The Sonazoid™ bubble appears to absorb air from its surroundings before the shell is broken. By pulse number 5 (i.e., FIG. 13E), the shell is compromised. Also note the apparent non-linearity of the bubble motion. The parameters for this data set are summarized in Table IV (FIG. 14). To summarize the data discussed above, at these modest pressures, Sonazoid™ microbubbles appear to have a semi-permeable shell when insonified, allowing air to be absorbed, and causing the bubble to grow. Both Optison™ and Sonazoid™ UCAs appear to show damage to the shell after two or more pulses. It should be noted that these results are examples involving individual microbubbles. It would be necessary to examine many such cases before a conclusion could be drawn as to the "average" response of a particular microbubble.

Figure 15:
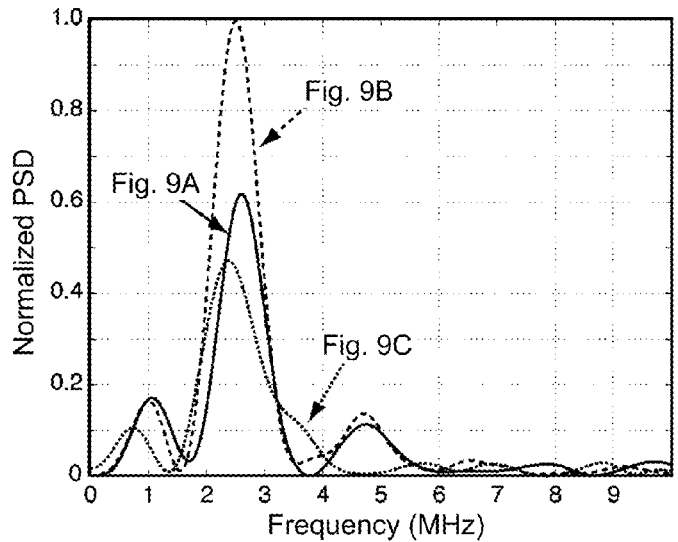

Spectral Analysis:

Light scattering data may also be suited to fast analysis by examining the spectrum of the signals. Toward this eventual goal, the power spectral densities (PSD) of the R(t) curves discussed above were examined. FIG. 15 graphically illustrates normalized PSDs. There are significant fundamental peaks in the PSDs of FIG. 15, related to the (real) resonance frequency of the system. Furthermore, apparent sub-harmonic and harmonic components were often observed. A more thorough analysis of these signals may eventually lead to better information about the response curves, or R(t) that could be used to optimize the agents for imaging and therapy.

The above empirical studies evaluated the feasibility of using light scattering to measure the radial pulsations of individual ultrasound contrast microbubbles (Optison™ or Sonazoid™) subjected to pulsed ultrasound. Experiments performed in a highly diluted xanthan gum mixture were used to verify that individual encapsulated microbubbles could be investigated. The evolution of individual contrast microbubbles was observed over several consecutive acoustic pulses, suggesting that shell permeability and/or shell fatigue are important consequences in the evolution of microbubbles. It appears that light scattering can be used to better understand the physical interaction between ultrasound pulses and contrast agents, and eventually be used to evaluate shell parameters and explore shell fatigue, leading to better agent design.
Summary of Initial Study of Optison™ and Sonazoid™ Bubbles:

Scattered light was collected from single UCA bubbles while the individual bubbles were oscillated with a diagnostic ultrasound machine. The empirical data were fitted with the Morgan model with good success. It was assumed that the thickness of the shell was relatively constant for a range of bubble sizes. Based on the trial fitting of the empirical data, it was determined that the shell parameters $\epsilon\mu sh=6$ nm Pa s for Optison™ and $\epsilon\mu sh=2$ nm Pa s for Sonazoid™ are acceptable. Those parameters were then input in the Morgan model so that the model was fitted to the empirical data with the initial value being the only variable. The empirical data were filtered using a 10 MHz low-pass filter. It was observed that the Morgan model correctly described the UCA bubble's response to longer acoustic tone bursts (i.e., therapeutic ultrasound) as well the bubble's response to short pulses from a diagnostic ultrasound instrument. The empirical data collected while oscillating UCAs to destruction indicate that it usually takes some time or several cycles for ultrasound pulses to disrupt the UCA bubbles. The destruction process appears to include distortion of bubble shape, the generation of partial defects or ruptures of the UCA shell, and an increase in the magnitude of this distortion, with the expansion of the UCA shell followed by the complete rupture of the UCA shell, yielding a free gas bubble. It is likely that shell fragments may still affect the nearby acoustic field and scattering field. It was observed that the damping characteristic of a UCA shell contributes to the resonance frequency shift to a lower frequency. When a UCA bubble is broken, the resonance frequency of the bubble is observed to increase (based on spectral analysis of the data).

Different Shelled UCA Models:

As noted above, many different dynamic models have been developed to describe the motion of microbubbles or spheres. A significant aspect of the light scattering technique disclosed herein is that the collected data (i.e., the RT curves) can be fitted to many different models. The number of variables being fitted can be minimized by acquiring data corresponding to as many of the model variables as possible. As discussed above, ambient pressure can be measured using a hydrophone while the scattered light is collected, eliminating pressure as a variable. The initial radius of a microbubble can be measured optically (i.e., using a microscope and a camera), or literature-based values can be used for the initial radius, eliminating yet another variable. Preferably, the only unknown variables involved in the fitting process relate to shell parameters, which to date, have been difficult to empirically measure. The following discussion is related to additional models.

The de Jong's model, Church's model, Hoff's model, and Sarkar's model are each based on the general RPNNP equation (i.e., Eq. (1)), which as noted above, describes the response of a spherical bubble to a time-varying pressure field in an incompressible liquid.

The assumptions for the RPNNP equation are: (1) the motion of the bubble is symmetric; (2) the wavelength of ultrasound is much larger than the bubble radius; (3) no rectified diffusion occurs; and, (4) the bubble contains gas or vapor, which is compressed and behaves according to the gas law, with the polytropic parameter held constant.

de Jong's Model:

De Jong modified the RPNNP equation to account for shell friction ($\delta_f$, included in $\delta_{tot}$) and elasticity ($S_p$) parameters as follows:

$$\rho_L R \ddot{R} + \frac{3}{2} \rho_L \dot{R}^2 = \quad (4)$$

$$P_g \left(\frac{R_0}{R}\right)^{3\kappa_1} + P_v - P_0 - \frac{2\sigma}{R} - 2S_p\left(\frac{1}{R_0} - \frac{1}{R}\right) - \delta_{tot}\omega\rho_L R\dot{R} - P_a\cos(\omega t)$$

where $S_p = 6G_s d_{se}(R/R_0)^3$, and $G_s$ is the shell shear modulus, and $d_{se}$ is the shell thickness. The total damping parameter is given by:

$$\delta_{tot} = \delta_{th} + \delta_R + \delta_\eta + \delta_f \quad (5)$$

and thermal damping constant is given by:

$$\delta_{th} = \frac{1}{\omega_0 \omega} \frac{p_0}{\rho_L a^2} \mathrm{Im}\left(\frac{1}{\Phi}\right) \quad (6)$$

The formula of $\Phi$ is adapted from Devin. The radiation resistance damping constant is given by:

$$\delta_R = \frac{\omega^2 a}{\omega_0 c} \quad (7)$$

and the viscosity damping constant is given by:

$$\delta_\eta = \frac{4\eta_L}{\omega_0 \rho_L R^2} \quad (8)$$

where $\eta_L$ is the liquid shear viscosity. The shell friction parameter is:

$$\delta_f = \frac{12\eta_s d_{se}}{\omega_0 \rho_L R^3} \quad (9)$$

where $\eta_s$ is the shell shear viscosity. The polytrophic exponent is:

$$\kappa_1 = \mathrm{Re}\left[\frac{1}{\Phi(R,\omega)}\right] \quad (10)$$

Church's Model:

In Church's work, a Rayleigh-Plesset-like equation describing the dynamics of shelled gas bubbles was derived. It was assumed that a continuous layer of incompressible, solid elastic shell with damping separates the gas bubble from the bulk Newtonian liquid. The elastic surface layer stabilizes the bubble against dissolution by supporting a strain that counters the Laplace pressure. Viscous damping is considered in this model, which is as follows:

$$\rho_s R_1 \ddot{R}_1 \left[1 + \left(\frac{\rho_L - \rho_s}{\rho_s}\right)\frac{R_1}{R_2}\right] + \rho_s \dot{R}_1^2 \left\{\frac{3}{2} + \left(\frac{\rho_L - \rho_s}{\rho_s}\right)\left[\frac{4R_2^3 - R_1^3}{2R_2^3}\right]\frac{R_1}{R_2}\right\} = \quad (11)$$

$$P_{G,eq}\left(\frac{R_{01}}{R_1}\right)^{3\gamma} - P_\infty(t) - \frac{2\sigma_1}{R_1} - \frac{2\sigma_2}{R_2} -$$

-continued $$4\frac{\dot{R}_1}{R_1}\left[\frac{V_s\eta_s + R_1^3\eta_L}{R_2^3}\right] - 4\frac{V_sG_s}{R_2^3}\left(1 - \frac{R_{e1}}{R_1}\right)$$

where $\rho_s$ is the shell density, $\sigma_1$ is the surface tension of the gas-shell interface, $\sigma_2$ is the surface tension of the shell-liquid interface, $P_{G,\,eq}=P_0$ for the surface layer permeable to gas, and:

$$P_\infty(t) = P_0 - P_a\sin(\omega t) \tag{12}$$

$$V_s = R_{02}^3 - R_{01}^3 \tag{13}$$

$$R_{e1} = R_{01}\left[1 + \frac{\left(\frac{2\sigma_1}{R_{01}} - \frac{2\sigma_2}{R_{02}}\right)\frac{R_{02}^3}{V_2}}{4G_s}\right] \tag{14}$$

Hoff's Model:

A simplified equation was derived from Church's equation by Hoff, for the case of thin shell, $d_{se}(t) \ll R_2$:

$$\rho_L R\ddot{R} + \frac{3}{2}\rho_L \dot{R}^2 = P_0\left[\left(\frac{R_0}{R}\right)^{3\gamma} - 1\right] - \tag{15}$$

$$4\eta_L\frac{\dot{R}}{R} - 12\eta_s\frac{d_{se}R_0^2}{R^3}\frac{\dot{R}}{R} - 12G_s\frac{d_{se}R_0^2}{R^3}\left(1 - \frac{R_0}{R}\right) - P_i(t)$$

Sarkar's Model:

Chatterjee and Sarkar developed a new model for encapsulated contrast agent microbubbles, as follows:

$$\rho_L\left(R\ddot{R} + \frac{3}{2}\dot{R}^2\right) = \tag{16}$$

$$\left(P_0 + 2\frac{\sigma_i}{R_0}\right)\left(\frac{R_0}{R}\right)^{3\gamma} - 4\eta_L\frac{\dot{R}}{R} - 2\frac{\sigma_i}{R} - 4\frac{\kappa^s\dot{R}}{R^2} - [P_0 + P_{drive}(t)]$$

This model assumes the encapsulation of a contrast agent to be an interface of infinitesimal thickness with complex interface rheological properties. The interfacial tension, $\sigma_i$, and dilatational viscosity $\kappa^s$ are unknown interface and shell parameters.

Marmottant's Model:

Most shelled UCA models assume constant surface tension coefficients and small deformations of the microbubble surface. However, for phospholipid monolayer coatings, the surface area available per phospholipid molecule apparently varies as the microbubble oscillates. Thus, Marmottant derived an improved model (Eq. 6) specifically for microbubbles with lipid monolayer coatings. The model considers the microbubble shell as a two-dimensional viscoelastic medium and suggests that the shell elasticity can be modeled with a radius-dependent surface tension. There are two parameters introduced to model the shell properties: the shell elastic compression modulus $\chi$, and a shell dilatational viscosity $k_s$.

$$\rho_L\left(R\ddot{R} + \frac{3}{2}\dot{R}^2\right) = \left(P_0 + 2\frac{\sigma_i}{R_0}\right)\left(\frac{R_0}{R}\right)^{3\gamma}-\left(1 - \frac{3\gamma}{c}\dot{R}\right)- \tag{17}$$

$$2\frac{\sigma_w}{R} - 4\chi\left(\frac{1}{R_0} - \frac{1}{R}\right) - 4\eta_L\frac{\dot{R}}{R} - 4\frac{\kappa_s\dot{R}}{R^2} - P_0 - P_{drive}(t)$$

Marmottant's model (i.e., Eq. (17)) has been applied very successfully to the following UCAs: Sonovue® and BR14™ (Bracco Diagnostics).

Figure 16:
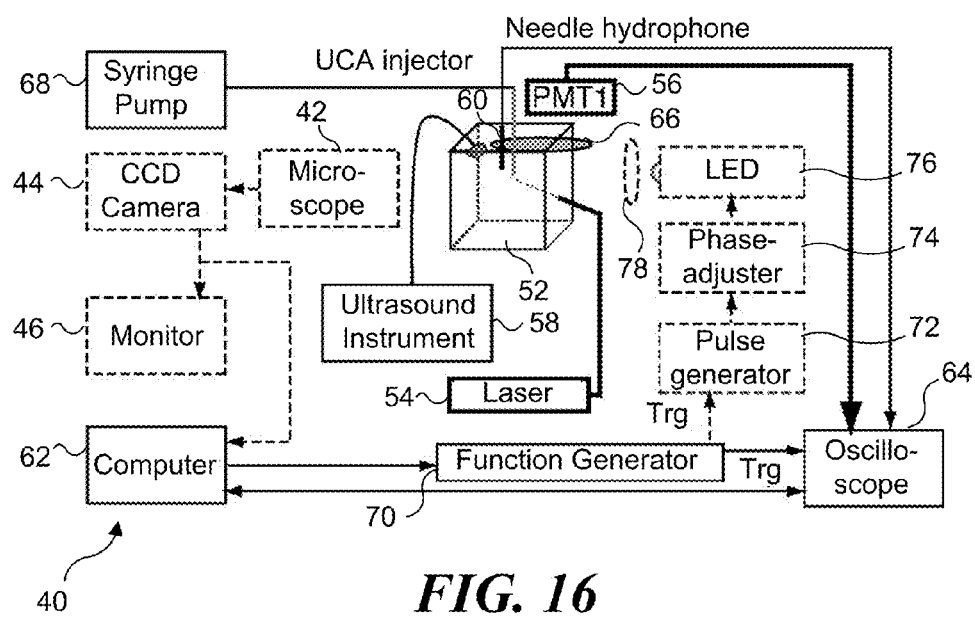

Additional light scattering empirical studies were performed measure the dynamic response of individual Sonovue™ bubbles to the driving acoustic pulse using a system 40 schematically illustrated in FIG. 16. Note that the system of FIG. 16 is based on the system of FIG. 2, and includes an optional microscope 42, an optional CCD camera 44, and an optional monitor 46 to enable the radius of the microbubble to be empirically measured, generally as discussed above. In brief, the highly diluted Sonovue™ suspensions were injected into the region of interest (ROI defined herein as being a small volume 52 where the ultrasound and laser beams intersected with Sonovue™ bubbles) using a syringe pump 68 (e.g., a 74900™ series, Cole-Parmer Instrument Co., Vernon Hills, Ill., USA) at a rate of 10 ml/h with a tube (0.5 mm inner-diameter). The driving acoustic pulses were sent from a probe of a diagnostic ultrasound instrument 58 (e.g., an Ultramark 4Plus™, ATL-Philips, USA) operated in M-Mode at 1-kHz pulse-repetition-frequency (PRF) and monitored using a calibrated needle hydrophone 60 (e.g., from NTR Systems Inc., Seattle, Wash., USA). An HeNe laser 54 (Melles Griot, Carlsbad, Calif., USA) was used as a light source. The waist of the laser beam was focused to less than 100 µm at the ROI by a lens (not shown). The scattered light signals from the microbubbles in the ROI were collected and focused by another lens 66 onto a photo-multiplier tube (PMT) detector 56 (e.g., a Hamamatsu, Model 2027™). The output signals from the PMT and the hydrophone were recorded using a high-speed digital oscilloscope 64 (e.g., from LeCroy, Chestnut Ridge, N.Y., USA) in sequence mode provided by a function generator 70, and then transferred to a computer 62 waiting from post-processing using a MatLab program (Mathworks Inc., Natick, Wash., USA). Optionally, a pulse generator 72 can be triggered by the function generator to produce a pulse signal applied to a phase adjuster 74, to produce light pulses with an LED 76 that are focused by a lens 78 into volume 52.

Figure 17A:
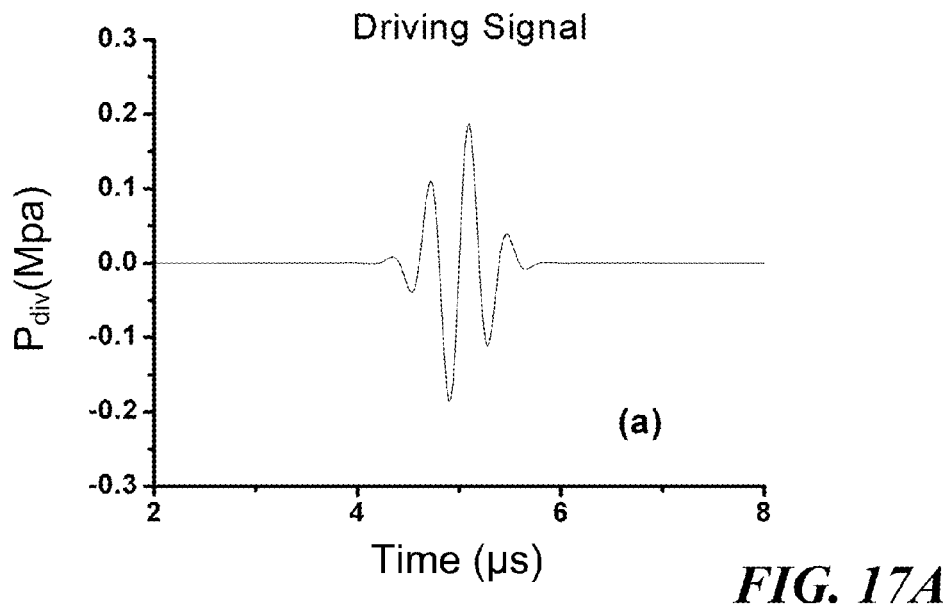
FIG. 17A illustrates a modified Gaussian pulse used to simulate a driving signal for different dynamic models.
Figure 17B:
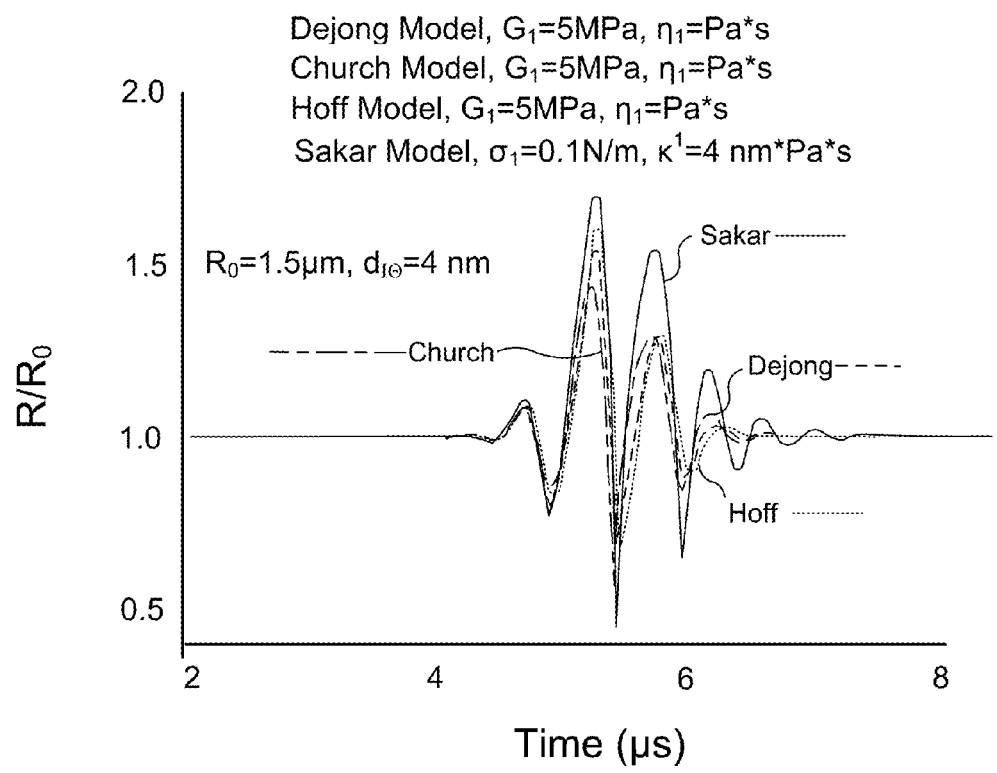
FIG. 17B illustrates typical bubble responses using four different dynamic bubble models.

Results and Discussion:

Four of the models discussed above (de Jong's model, Church's model, Hoff's model and Sarkar's model) were "run" with the same modified Gaussian pulse, $$P_{div}=P_0\sin[2\pi f(t-t_c)]\exp[-\pi^2 h^2 f^2(t-t_c)^2] \tag{18}$$

with $t_c$=5 µs and h=⅓. The results indicate that each model appears to provide substantially similar results in a certain parameter range. FIGS. 17A and 17B graphically illustrate the response of a 1.5 µm radius bubble subject to a 2.5 MHz modified Gaussian pulse with a peak negative pressure of 0.2 MPa. FIG. 17A illustrates the modified Gaussian pulse is used to simulate the driving signal, while FIG. 17B illustrates typical bubble responses using the four above noted dynamic bubble models. The parameters used for the simulation are given below.

$\rho_L$=103 kg/m, density of a Newtonian liquid
$P_0$=101300 Pa, ambient pressure
$P_v$=2330 Pa, vapor pressure (Chang et al, 1999)
$\sigma$=0.07275 N/m, surface tension
$\rho_g$=1.161 kg/m³, gas density
$C_p$=240.67, heat capacity at constant $K_g$=0.00626, thermal conductivity (for air at 300K and 1 atm)

c=1500 m/s, acoustic velocity

γ=1, gas adiabatic constant $\eta_L$=0.001 Pa×s, liquid shear viscosity (Church et al, 1994)

$\rho_s$=1100 Kg/m$^3$, shell density (Church et al, 1994)

$\sigma_1$=0.04 N/m, surface tension of the gas-shell interface (Church et al, 1994)

$\sigma_2$=0.005 N/m, surface tension of the shell-liquid interface (Ibid.)

As noted above, and as illustrated in FIG. 17B, each model appears to provide substantially similar results within a certain parameter range. However, if the selected shell parameters (e.g., shell viscosity $\eta_s$ and shell shear modulus Gs), are out of a certain range, these models will likely produce different responses. Since the same shell parameters are used in the de Jong, Church, and Hoff models, the studies here are focused on these three models. FIGS. 18A-18C graphically illustrate results provided by these three models with varying parameters. Each of the three models provides substantially the same result with appropriately selected parameters (FIG. 18A), whereas the simulation results become different from each other with increasing Gs (e.g., Gs>50 Mpa; FIG. 18C) or decreasing $\eta_s$ (e.g., $\eta_s$<0.1 Pa*s; FIG. 18B). Additional non-linear behaviors can be observed with the changed shell parameters, which suggests that each of the three models might have similar linear responses, while their non-linear responses differ. Therefore, although the acoustic driving parameters are controllable, it is still difficult to tell which model is 'better' without knowing the shell parameters a priori. Further studies on UCA shell parameters are important and necessary to make it possible to rank the various models.

Figure 19B:
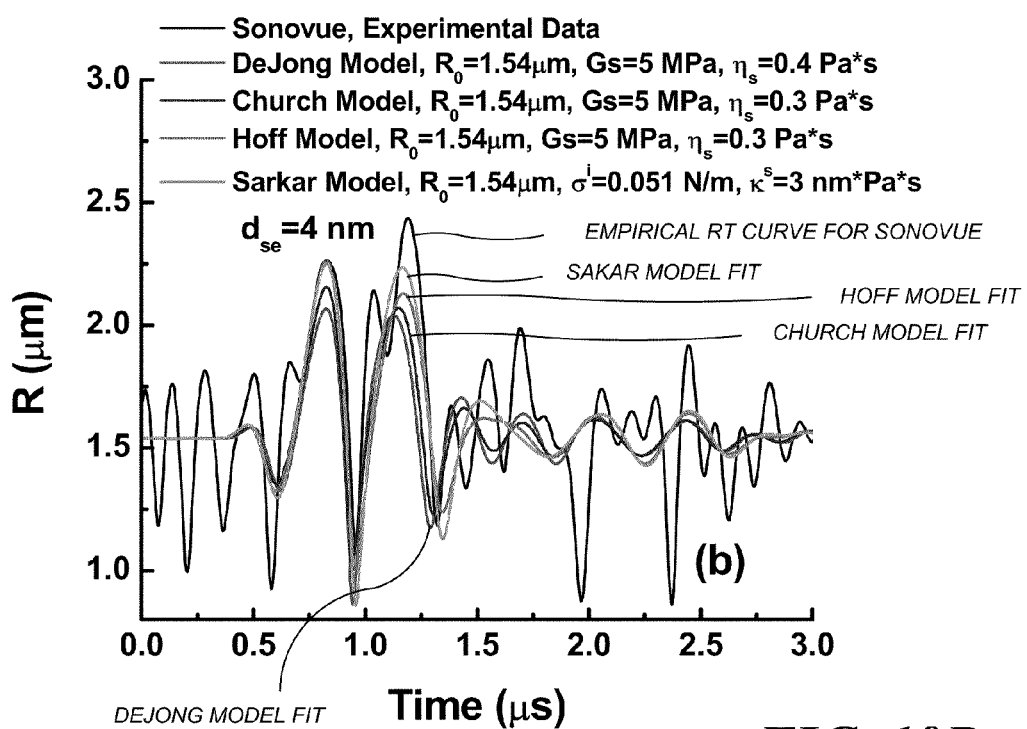

Although as noted above different models can give similar simulations results with appropriately selected parameters, to verify the accuracy of the these models (i.e., de Jong's model, Church's model, Hoff's model, and Sarkar's model) the experimentally measured Sonovue™ bubble RT curve can be fitted to each of the four models with selected fitting parameters. Literature reports that Sonovue™ bubbles have a very thin lipid shell whose thickness is assumed to be 4 nm. Three unknown fitting parameters were chosen for present work: $R_0$, Gs, and $\eta_s$ in de Jong, Church, and Hoff's models, and $R_0$, $\sigma_i$, and $\kappa^s$ in Sarkar's model. Minimum standard deviation evaluation is applied to determine the best fitting. FIGS. 19A and 19B graphically illustrate a comparison between the experimental data and simulated results, with the Sonovue™ bubble oscillating with a driving pressure amplitude of about 0.15 MPa. The results indicate that Sonovue™ bubbles behave in a strongly non-linear motion. The likely explanation for this observation is that the lipid shells of Sonovue™ bubbles are very thin and relatively permeable. Therefore, the properties of the Sonovue™ bubble shell likely change when the bubble is driven by acoustic pulses, which induces the observed non-linear behavior.

FIG. 19B graphically illustrates that the empirically measured scatter light RT curve for a Sonovue™ bubble can be fitted reasonably well to each of the four models. The fitted initial radius for each model converts to 1.54 μm, which agrees with the manufacturer's data. However, at the later stages of the driving pulse, the fitting results can not follow the measured non-linear response, which suggests that a better model is needed in order to satisfactorily account for the non-linear response of a Sonovue™ bubble. The Sonovue™ bubble's non-linear behavior might result from the change of bubble shell parameters during its oscillation. If it is assumed that the fitting results for experimental data are acceptable, the relationship between Sonovue™ shell parameters, e.g., shear modulus Gs and shear viscosity $\eta_s$, and bubble initial radius ($R_0$), can be obtained by fitting the pooled experimental data with the selected numerical model. Since all four of these models yield similar simulation results for the experimental data (as shown in FIG. 18B), it is reasonable to select any one of the four models to quantify the bubble shell parameters. In this study, Hoff's model was ultimately selected, since it is based on a thin-shell assumption. In order to simplify the computational process, the lipid shell thickness for the Sonovue™ bubble was assumed to be a constant value of 4 nm, as reported in the literature.

FIGS. 20A and 20B graphically illustrate that both shell shear modulus and shear viscosity increase with increasing initial radius, which implies the shell properties of UCA bubbles are not homogeneous, and may be related the bubble size. FIG. 20A graphically illustrates the change of the shell shear modulus as a function of radius, while FIG. 20B graphically illustrates the change of the shell viscosity as a function of radius. These results suggest that UCA shell properties will significantly affect bubble dynamic behaviors. However, considering the lack of effective methods to measure the shell properties directly, further efforts on the study of UCA shell parameters using the light scattering techniques disclosed herein are imperative for improving UCA development and applications.

The results of further studies involving three of the models (Mannottant, Sarkar, and Hoff) are summarized in Table IV (below). The results suggest that all three models perform equally well in describing the experimental data in the central region, while all models show deviations from the experimental data at the beginning and end stages. The minimum STD values are similar for all three sets of shell parameters. The relative equality between the models suggests that it would be difficult to rank the models without a priori knowledge of the shell parameters.

TABLE IV

Best fit shell parameters and minimum STD

| UCA Model | Shell Elasticity | Shell Viscosity | Minimum STD |
|---|---|---|---|
| Marmottant | shell elasticity $\chi$ = 0.25 N/m | dilatational viscosity $k_s$ = 4 nm · Pa · s | 0.054 |
| Sarkar | interfacial tension $\sigma_i$ = 0.32 N/m | dilatational viscosity $k_s$ = 4 nm · Pa · s | 0.054 |
| Hoff | Shear Modulus $G_s$ = 23 MPa | Shear viscosity $\eta_s$ = 0.5 Pa · s | 0.059 |

Measuring Multiple UCA Bubble Dynamics Using Light Scattering:

The single Optison™ and Sonazoid™ studies discussed above prove the value of light scattering in studying the dynamics of single bubbles. Additional empirical studies were performed to study a group of UCA bubbles using scattered light. Such group dynamics are important, as in clinical conditions, masses of UCAs (as opposed to individual bubbles) are employed. Such research has indicated that at a relatively low driving power, UCA bubbles are observed responding to the acoustic driving wave and oscillate. At relatively higher driving powers, the destruction of UCA bubbles is observed (as expected). Significantly, the harmonic response of UCA bubbles can be observed at varied driving powers.

When studying multiple UCA bubbles, the analysis is more complex, concerning both optics and acoustics. Statistically speaking, the properties of UCA bubbles can be estimated by its distribution profile, provided by the manufacturers. The profiles can be described with a known statistics algorithm, such as Gaussian distribution, to make it simpler to model distribution of UCA bubbles, and therefore analyze the statistical characteristics of UCA bubbles. Once the statistics package is determined, the properties, such as mean and variation, can be applied to the model to perform simulation. UCA bubbles are so small that there are about half a billion of them in a single milliliter. For Optison™, there are $5\times10^8$-$8\times10^8$ individual bubbles per milliliter. Since so many bubbles are involved, it is difficult to know the number of bubbles in the region of interest.

From an acoustical standpoint, the measured acoustic pressure may not correctly describe the actual acoustic field that activates the UCA bubbles, since the UCA cloud alters the acoustic driving field. Further, the driving pressure is attenuated inside the UCA cloud. This obvious impact is indeed observed in the measurement of acoustic pressure in the field. However, the acoustic measurement is necessary to monitor the pressure level outside the targeted UCA cloud. The pressure signals also trigger data collecting events, which means that the pressure measurement cannot be used to describe the pressure on each individual UCA bubble for modeling and data fitting, as it was in the single UCA studies described above.

From an optical standpoint, the laser beam is affected similarly, in that a mass of bubbles scatters light differently than an individual bubble. As a whole, the UCA bubbles in the path of the laser beam are not homogeneously distributed. The laser beam itself is not homogeneous either, having a transverse intensity distribution. This does not impact individual UCA bubbles; however, the inhomogeneous cross-distribution of the laser beam means that a UCA bubble at the center of the laser beam encounters more light than a UCA bubble near the edge of the laser beam.

To address these issues, the RT curves discussed above are modified, to achieve an effective RT curve. The effective RT curves are computed from the light scattering data, based on the assumption that each UCA bubble is separated far enough from its neighboring bubbles such that there is no attenuation to the incident light intensity on each UCA bubble. It is also assumed that the laser beam is homogeneous, which means each UCA bubble scatters laser light as if there is only one UCA bubble in the region. The effective scattered light intensity of the collected data combines the contributions from every bubble.

The multiple bubble study employed an HDI 5000™ ultrasound system, which is able to operate in many modalities, including B-Mode, M-Mode and Pulse-Doppler Mode, each of which was used in the multiple bubble study. The HDI 5000™ system (probe) functions as an acoustic source; and, each modality features a different pulse length and central frequency. Every modality can provide either low or high power. The intact UCA bubbles' response to acoustic driving pulses, and the destruction of the UCA bubbles, are of great interest in revealing the UCA bubbles' properties. Since today's diagnostic ultrasound systems perform harmonic imaging with UCA bubbles mainly in a B-Mode at extremely low power, much of the data collected in the multiple bubble study were obtained using the B-Mode at a low driving power (MI).

FIG. 21A graphically illustrates a typical effective RT curve of a mass of UCA bubbles (i.e., the effective RT curve of UCA bubbles in B-Mode at MI=0.04), and FIG. 21B graphically illustrates the power spectrum of the UCA bubbles' response. These Figures provide an understanding of how the light scattering data were processed. The data utilized in these Figures were collected in the B-Mode with MI=0.04, where the fundamental frequency in B-Mode is about 2 MHz. The effective RT curve was generated from a light scattering signal that monitors the dynamic oscillation of the UCA bubbles. In FIG. 21B, the power spectrum of the UCA bubbles' dynamics is lower than 2 MHz. This shift of fundamental frequency between the bubbles' response and that of the driving pressure is discussed below. The main focus of the multiple bubble study was on the spectrum properties of UCA bubbles' response. However, the destruction properties of UCA bubbles are of interest as well. In the following discussion, where the focus is on spectral analysis, the RT curves may not be provided.

It is recognized that the UCA cloud will scatter some of the incident acoustic beam, which will result in the attenuation of the acoustic pressure on the UCA bubbles in the path of acoustic beam. Thus, the UCA bubbles are not homogeneously driven, which further complicates the analysis of the collected data. Because the region of interest upon which the PMT is focused is very small, it is assumed that all the UCA bubbles are homogeneously activated. Note that as indicated in FIG. 21A, the effective expansion of the UCA bubbles is relatively small (i.e., the expansion is only about 5% of their ambient sizes).

The B-Mode:

In the B-Mode, the driving power (MI) starts as low as 0.03 (the lowest HDI 5000™ power setting). FIG. 21C graphically illustrates two examples (i.e., one a solid line, and one a dashed line) of the power spectrum at MI=0.03. The harmonic response of each example is slightly different, possibly due to the difference of the specific local UCA bubbles. Significantly, as indicated by each example, the UCA bubbles respond to the acoustic source, even though the driving pulses are very weak. Further, the power spectrum reveals strong fundamental components, while a harmonic component is observed as well. The harmonic component can be particularly significant, as the solid line indicates. When compared with the driving pulse central frequency (2 MHz—not shown), it is evident that the fundamental frequency of the UCA bubbles' response is shifted relative to the frequency of the driving pressure, as will be noted in FIG. 21B. It is also noted that the response of the second group of UCA bubbles (i.e., the second example, whose data are shown in the graph with a dash line) indicates different spectral characteristics in the power spectrum. That is, the feature of the fundamental component in the power spectrum of the UCA bubbles' response is different.

FIG. 22 is a composite graph illustrating the power spectrum of UCA bubbles driven by different acoustic power (MI) settings, using the B-Mode. As indicated in the Figure, the fundamental frequency shifts to a lower frequency when the driving power is lower than MI=0.05, clearly, responding differently to different acoustical driving powers. Because higher acoustic power settings can destroy UCA bubbles, lower power settings are generally preferred (unless UCA destruction is desirable, as in the case of using microbubbles to deliver therapeutic agents encapsulated in the bubbles). It should be noted that the data graphically illustrated in FIG. 22 were generated from intact UCA bubbles oscillating due to acoustic pulses. FIG. 22 shows the power spectrum of UCA bubbles' response with a driving power at MI=0.03, 0.03+, 0.04, 0.04+, 0.05, 0.05+, 0.06 0.07, and 0.11, respectively. The + sign refers to the middle level of MI for the HDI 5000™ system, between two consecutive defined MI settings. The selection of MI is based on the smallest step of power increase starting from the lowest available value, but the step is greater between the last two highest powers.

Referring to FIG. 22, it should be noted that the fundamental frequency of the bubbles' response varies. When the driving power is lower than MI=0.05, the fundamental component (at about 2 MHz) of the bubbles' response shifts to a lower frequency. When the driving power is 109 (equal to or greater than MI=0.05), the fundamental frequency seems to match satisfactorily (though not perfectly) the acoustic driving frequency. Further, the harmonic frequency components vary based on driving power, which can be observed in both low and high power drive settings. There seems no great advantage to use higher driving power settings to generate harmonic components. A second harmonic frequency shift (at about 4 MHz) basically follows the trend of the fundamental frequency. When the fundamental frequency shifts toward a lower frequency, the corresponding second harmonic frequency also shifts toward a lower frequency. Finally, the sub-harmonic component (at about 1 MHz) can be identified in most of the examples, but the power of sub-harmonic component is very weak. In most of the examples, the harmonic components at 3 MHz, 5 MHz and 7 MHz can be identified, especially for examples employing a higher driving power. Overall, the various examples illustrated in FIG. 22 do not suggest that the generation of harmonic components in the response of the bubbles to an acoustic driving is highly dependent on the power of operation employed during the insonification, while the bubbles are intact.

Further statistical analysis of the data to determine why the fundamental frequency, as well as harmonic frequencies, of the response of the bubbles shifts when a low driving power is employed did not indicate any dependence of fundamental frequency of the bubbles' response to the driving powers. A higher driving power increases the chance of generating more (and stronger) harmonic components, as well as sub-harmonic components, even though the power of sub-harmonic components are usually much smaller than that of harmonic components. The statistical analysis confirmed that both the shift of harmonic frequencies (second harmonic and third harmonic frequencies) and the shift in the fundamental frequency are in the same direction (i.e., a shift to lower frequencies), although the shifts in the harmonic frequencies are greater in magnitude.

It appears that there is a pressure threshold (MI=0.05 in the examples of FIG. 22) in the B-Mode, which impacts the UCA bubbles' response. Because the frequency shift of UCA bubbles' response does not relate to the driving power, when the driving power is low, the cause of the frequency shift must come from the UCA bubbles themselves. The frequency shift (to a lower frequency at a low driving power) is likely due to a size distribution of the UCA bubbles, since the majority of the UCA bubbles are in the range between 1 μm and 2 μm in radius. When the driving pressure is small, the UCA bubbles may oscillate with the driving wave, as well as experience self-resonance. The coupling of the oscillations could result in the change of spectral features. When the driving pressure is sufficient, the forced oscillation overcomes the self-oscillation, to emerge as a main contributor to the spectra, resulting in the fundamental frequency resembling that of the driving power.

Regardless of the spectral features, it is noteworthy that at an MI as low as 0.03, the harmonic components in the responses of UCA bubbles can still be generated. This finding indicates that the harmonic component in the response of UCA bubbles can be generated as long as the bubbles are forced to oscillate. However, it is recognized that UCA bubbles will not oscillate strongly when the driving power is low, and the signal level indeed could be extremely low. Thus, when the driving power is low, the harmonic components may not be distinguishable from noise.

FIGS. 23A and 23B are composites. The development of UCA bubbles during consecutive insonification in one data sequence (collection) is graphically illustrated as RT curves in FIG. 23A, and as power spectrums in FIG. 23B. Each sub-figure in the composite represents an averaged result over the duration of a consecutive activation.

When multiple UCA bubbles are involved, if they are in close proximity, they are likely interact with one another to some degree. The data collected to generate FIGS. 23A and 23B were collected with an MI of 0.05+. In the RT curves of FIG. 23A, the effective radius of the UCA bubbles continues to increase during insonification. The magnitude of the forced oscillation builds up initially and then slows. It appears that none of the UCA bubbles were burst during the activation, because there is no significant sudden increase of effective radius that would indicate breaching of the shell. In the corresponding power spectrums of FIG. 23B, the fundamental frequency of responses of the UCA bubbles does not change, which suggests that there is no significant physical change to the bubbles in this area. Under this condition, the gain of ambient effective radius of the UCA bubbles in the area suggests that the increase in light scattering is primarily due to an adjustment of the spatial distribution of bubbles in the area. If the bubbles are closely packed, their expansion is limited by the proximity of neighboring bubbles. As the UCA bubbles oscillate with the acoustic wave, they also interact with one another as well, and thereby alter the spatial distribution characteristics.

It can be noted from FIG. 23A that the effective radius of the bubbles, after an acoustic pulse, is larger than before the acoustic pulse, although the difference is not particularly significant in these examples. FIG. 24 graphically illustrates data averaged over 100 consecutive pulses. The ambient effective radius before the acoustic pulses is about 9 μm, and the ambient effective radius after the acoustic pulses is about 9.5 μm. The data provide no indication that any bubbles are being ruptured, which suggests that the acoustic driving power contributes to the increase of the UCA bubbles' scattering capability. That there is no bubble destruction, or physical change in the bubbles, suggests that the change of the spatial distribution of the bubbles is the key factor in the observed increase in the light scattering capability of the UCA bubbles in the area.

It was also observed that the magnitude of the response of the UCA bubbles falls gradually after segment 220 in FIG. 23A, while these bubbles' ambient scattering capability is still increasing. It is believed that the bubbles' scattering capability is increasing with respect to both light and sound. When the UCA bubbles spread out, they can oscillate more freely, with less interaction, so that both ambient scattering capability and the magnitude of oscillation increase. Meanwhile, the bubbles that encounter the acoustic wave first are able to scatter more energy, and bubbles that encounter the acoustic wave later are driven by weaker acoustic pulses, which results in the decreasing magnitude of oscillation. However, the ambient scattering capability is not affected. This combined effect results in the phenomenon in the RT curves of FIG. 23A that ambient scattering capability keeps increasing, while the amplitude of oscillation first increases and then falls.

The data set graphically illustrated in FIGS. 23A and 23B shows the development of UCA bubbles during insonification at extremely low driving power. It should be noted that UCA bubbles can break even at very low acoustic power levels. As is known, when gas bubbles are released (by the breaking of a shell) and are driven by acoustic pulse, such gas bubbles can suddenly grow in size tremendously. The data set graphically illustrated in FIGS. 25A and 25B relates to such a condition, where UCA bubbles start to break and dissolve during insonification at low MI (=0.05). FIG. 25A includes RT curves of the same group of UCA bubbles during the consecutive insonification, while FIG. 25B shows the corresponding power spectrums. Four consecutive segments (UCA bubbles' response to acoustic pulses) are shown in the Figures. In segments 260 and 262, the RT curves actually reveal a change in the dynamics of the UCA bubbles, when compared with the RT curve of FIG. 20A. The breaking of the UCA bubbles is clearly illustrated with the sudden increase of effective radius in segments 261 and 263. The breakage can also be visualized in the power spectrums of FIG. 25B. The fundamental, harmonic, and sub-harmonic frequencies are clearly seen in segments 260 and 262. The broad increases of the power spectrum in segments 261 and 263 are symbolic of the sudden increases of the effective radius and the breakups of UCA bubbles. Even though the whole sequence is not shown here, the sequence data indicates that additional bubbles are breaking during the insonification. This data set also shows that UCA bubbles may break in groups or individually at a low driving power, depending on the actual input power. The fact that UCA bubbles break gradually at a low MI is also proven in this example. Note that the ambient effective radius does not change from segments 260 to segment 263, which suggests that the number of UCA bubbles broken in segments 261 and 263 is not significant.

It has been shown that the harmonic frequency is generated by UCA bubbles responding to acoustical pressure. If the second harmonic component is sufficiently strong, the RT curve should reflect this phenomenon, which is shown in FIGS. 26A and 26B, with FIG. 26A corresponding to the RT curves, and FIG. 26B corresponding to the power spectrum. The driving power for this data set was MI=0.06. In the RT curve, the waveform of the second harmonic component can clearly be observed, coupled with the fundamental frequency waveform. In the power spectrum, the second harmonic component is apparent. The power level of the second harmonic component is comparable with that of the fundamental component.

Pulse-Doppler Mode:

A typical response of masses of UCA bubbles to the Pulse-Doppler Mode is graphically illustrated as an effective RT curve in FIG. 27. Pulse-Doppler Mode is different than the B-Mode, in both its higher central frequency (about 2.4 MHz) and longer pulse length. In the Pulse-Doppler Mode, the lowest available acoustic driving power (MI) in the instrument employed in the multiple bubbles testing is 0.04. The change of modality applies acoustic pulses of different fundamental frequency and pulse length to the UCA bubbles. FIG. 28 graphically illustrates the corresponding power spectrum, enabling the harmonic responses of UCA bubbles to be observed when stimulated in the Pulse-Doppler Mode. The second harmonic power and even higher harmonic power sometimes could be very strong. The detailed profile varies and may reflect the specialty of the local UCA bubbles.

FIG. 28 includes three data sets, collected using a driving power of MI=0.04 in the Pulse-Doppler Mode. The fundamental frequency component profiles resemble one another in these examples, while their details differ between data sets, as discussed above with respect to FIG. 21 (B-Mode). The second harmonic component (at about 5 MHz) can be strongly visualized at MI=0.04; and even the third harmonic component (at about 6.5 MHz) can be very significant. At a very low driving pressure, the fundamental frequency of the response of the UCA bubbles does not shift, as was observed in the B-Mode.

As noted above, UCA bubbles start to break or dissolve even at particularly low driving powers. While the extremely strong harmonic components FIG. 28 could possibly arise due to breaking bubbles, because the effective radius (not shown) in the data sets of FIG. 28 does not change before and after the acoustic pulses, and because there is no sudden increase of effective radius during the entire sequence, it appears that none of the UCA bubbles were broken during the insonification of the data sets. Thus, it is believed that the stronger harmonic components are due to intact UCA bubbles. Some vulnerable UCA bubbles that could be destroyed near a power at MI=0.04 might be driven extremely non-linearly to generate strong a harmonic power, even though there is no bubble that is destroyed.

FIG. 29 is a composite graphically illustrating the power spectrum of multiple UCA bubbles being driven by different acoustic power (MI) in the Pulse-Doppler Mode. In order to visualize the impact of the variation in the power levels, FIG. 29 illustrates the power spectrums of multiple UCA bubbles at the following different MI: 0.04, 0.05, 0.06, 0.08, 0.09, and 0.10. The UCA bubbles are intact in these examples. The following conclusions can be made. First, it is obvious that the fundamental frequency and second harmonic frequency components can be very strong. Again, there is no frequency shift as was observed in B-Mode at a low driving power. Second, sub-harmonic components can be identified easily in some examples. Third, as in the B-Mode, the generation of harmonic components in the responses of masses of UCA bubbles does not depend on the driving power when the targeted bubbles are intact.

M-Mode:

FIG. 30A graphically illustrates a typical response from a mass of UCA bubbles to M-Mode stimulation (i.e., an effective RT curve of UCA bubbles in M-Mode at MI=0.04), while FIG. 30B graphically illustrates a corresponding power spectrum. The M-Mode features a central frequency of 2.4 MHz, with a shorter pulse length. In the M-Mode, only extremely high power (MI) is applied, to focus on the destruction of UCA bubbles. FIG. 30C is a composite image that graphically illustrates consecutive effective RT curves of a mass of UCA bubbles responding to M-Mode stimulation. The driving power employed to collect the data for FIG. 31 was MI=0.7. In FIG. 30C, the first acoustic pulse (segment 1) destroys a significant amount of UCA bubbles, and brings down the effective RT from about 28 μm, before the acoustic pulse, to about 20 μm just after. It was enlightening to note that a single pulse can indeed destroy UCA bubbles. It is also observed that the UCA bubbles oscillate with the driving pulse while they are breaking. The second acoustic pulse (segment 2) causes more breakage, and brings down the effective RT from about 21 μm to about 18 μm. Even though the degree of destruction decreases, the third acoustic pulse (segment 3) and the fourth acoustic pulse (segment 4) continue breaking bubbles.

The data suggest that some UCA bubbles remain unbroken, even at very high driving powers. This phenomenon can be observed in the data for the fourth pulse (segment 4, FIG. 30C), and in subsequent data (after segment 4) in the same data sequence, which is not shown. Compared with the data corresponding to FIGS. 25A and 25B, it is clear that higher acoustic pressure destroys UCA bubbles faster.

The multiple UCA bubble testing discussed above indicates that masses of UCA bubbles respond to acoustic waves, oscillate at even very low acoustic pressures, and generate a harmonic signal. The fundamental frequency of the response of masses of UCA bubbles can shift from that of a driving wave when the driving power is particularly low, which may reflect the characteristics of the local UCA bubbles. It was shown that the higher driving power does not provide an advantage with respect to generating harmonic responses of masses of UCA bubbles, when the driven UCA bubbles are intact. UCA bubbles can start to break at an extremely low driving power, as is known based on clinical practice. Higher acoustic driving levels will destroy UCA bubbles faster as expected, and such levels can destroy most UCA bubbles in a single pulse.

Summary and Conclusions:

To date, UCA bubbles have been studied mainly using acoustical methods. Significantly, in acoustical methods, the acoustic driving source will increase the background noise in the signal corresponding to the response of the UCA bubbles. An intrinsic property of acoustic transducers is the band-pass filtering of detected signals (the response of the UCA bubbles), which causes the spectral characteristics outside the pass band to be lost. To overcome these problems, the light scattering technique discussed above has been developed. The light scattering technique disclosed herein can be used to study the properties of individual UCA bubbles, or masses of UCA bubbles, when such bubbles are driven by acoustic pulses. Because UCA bubbles are so small, it is difficult to use light scattering techniques in UCA research, because the light scattering data collected are so noisy. Several techniques can be used to reduce noise. One technique involves focusing a laser beam to increase the incident light intensity, changing the beam width from about 3 mm to about 0.2 mm in diameter, which results in a 225-times increase in the incident light power density. Another technique is to use a collecting lens to cover a wide angle, and to collect more scattered light. The SNR can also be increased using signal processing techniques in data processing, including both averaging and filtering techniques.

The foundation of the light scattering technique is the Mie scattering theory. Empirical data indicates that the Mie theory is valid not only for homogeneous spheres, but also for coated spheres, such as UCA bubbles. Empirical data have confirmed that the thin-shelled UCA bubbles resemble homogeneous spheres in regard to scattering light. This result facilitates the processing and modeling of the light scattering data.

The empirical data discussed above with respect to single bubble studies show that the light scattering technique is a powerful tool for studying UCA bubbles, even though the SNR is challenging. Overcoming the SNR issue using the techniques noted above enables a response of UCA bubbles to different levels of acoustic driving signals to be observed successfully. One or more of the dynamic models discussed above can be used to fit the empirical data to the model, enabling UCA parameters to be calculated using the model. The empirical data demonstrated that UCA bubbles respond to acoustic driving pulses, and that UCA bubbles may undergo physical property changes. For example, Sonazoid™ bubbles increase in size during insonification, while other parameters, such as shell properties, remain unchanged. This phenomenon was confirmed in the corresponding power spectra of the response of the UCA bubble responses, where the fundamental frequency of the response of the bubbles decreases during the insonification. The increase in the UCA bubble's ambient radius suggests that the thin-shelled UCA bubbles can exchange gas through the shell membrane. They intake more gas from the surrounding medium, resulting in bigger bubbles.

The single bubble study also illustrates that UCA bubbles oscillate with driving pulses stably, even when the driving strength is weak. When the pulse length of the acoustic driving is longer, such as the examples with a single element transducer (HIFU transducer), the UCA bubble's oscillation tends to be stable when the acoustic driving pressure is stable. However, when the driving strength is strong, UCA bubbles will eventually be destroyed. By interpreting experimental data with the dynamic model, the destruction of UCA bubbles is well illustrated. The data indicate that the shells of UCA bubbles are distorted before the bubbles are destroyed. The ratio of the maximum radius to the ambient radius of UCA bubbles remains relatively constant when the UCA bubbles are intact. A sudden increase in this ratio occurs when UCA bubbles start to break up, and the ratio increases further afterwards. From the power spectra of the response of the UCA bubbles, it can be concluded that both harmonic and subharmonic components are generated when acoustic pulses drive UCA bubbles. Sometimes, the higher harmonic power is strong enough to be comparable with that of fundamental and second harmonic components.

Additional studies directed to using scattered light from masses of UCA bubbles employs an effective radius to account for interaction among the mass of bubbles. The empirical data indicate multiple UCA bubbles behave similarly to individual UCA bubbles, while due to the spatial distribution of the bubbles, interaction among the UCA bubbles and scattering of incident light and ultrasound, variations between individual UCA bubbles are also observed. Thus, the techniques disclosed herein can also be applied to study masses of UCA bubbles.

The results from the multiple bubble study indicate that the harmonic components of UCA bubbles' response can be generated at an extremely low driving pressure. This finding indicates that harmonic components can be generated whenever bubbles are forced to oscillate. Indeed, the oscillation will be slight when the driving pressure is weak. Therefore, the SNR becomes a critical factor at relatively lower driving pressure levels. In some cases, higher harmonic components, such as second, third, and even fourth harmonic components, can be very significant, compared to the fundamental components. The multiple bubble study also revealed that the response of a group of UCA bubbles can be different at a low driving pressure as compared with a higher driving pressure. In the B-Mode, the fundamental frequency of the response of the mass of UCA bubbles shifts to a lower frequency, when the driving power is lower than MI=0.05, which indicates that the self-resonant oscillation of UCA bubbles plays a role in this phenomenon. When the oscillation due to the acoustic wave is not strong, the self-resonant oscillation is comparable to the forced oscillation, so that the power spectrum of the combined oscillation of UCA bubbles is different than that of the acoustic driving pressure. However, when the forced oscillation is strong, it dominates, and the power spectrum of the response of the mass of UCA bubbles resembles that of the driving pressure.

In practice, UCA bubbles are vulnerable, and are easy to break, even at an extremely low pressure. Some of the UCA bubbles in a mass of bubbles start to break at MI=0.04. This phenomenon can be successfully observed using the light scattering technique disclosed above. A sudden increase of effective radius indicates the destruction of one or more UCA bubbles, and the release of their inner gas core. The corresponding power spectrum confirms this finding. When the driving power is strong, more UCA bubbles are expected to break during a given time interval. A particularly strong acoustic driving pressure can destroy many UCA bubbles with a single pulse. The surviving bubbles are further destroyed in a second pulse. Significantly, the UCA bubbles respond to the driving pulse even while they are being destroyed.

In conclusion, the light scattering technique disclosed herein can be used as a powerful tool to study and determine UCA shell parameters. The empirical data discussed above demonstrate the following:

- The light scattering technique disclosed herein is an excellent tool to study UCA bubbles.
- UCA bubble dynamics are correctly modeled with various dynamic models.
- Individual UCA bubbles respond to acoustic driving pressure and undergo development during insonification.
- Both the harmonic and sub-harmonic components of the response of an individual UCA bubble can be generated when it is forced to oscillate.
- Imaging an individual UCA bubble with diagnostic ultrasound is feasible.
- The harmonic component of the response of masses of UCA bubbles can be generated when bubbles in the mass are forced to oscillate.
- Light scattering can be used to observe UCA bubbles breaking at an MI=0.04.
- Very strong acoustic pressure can destroy most UCA bubbles in a mass of bubbles in a single acoustic pulse.

It should be recognized that existing particle sizing instruments can be modified to implement the concepts disclosed herein. Conventional particle sizing instruments use light scattering to determine the radius of one or more particles. Significantly, these instruments are designed to collect light scattering data from particles while the particles are static (i.e., while the particles are not experiencing changing pressure conditions). These instruments will be referred to herein and the claims that follow as static light scattering particle sizing instruments.

Such static light scattering particle sizing instruments can be modified by incorporating a pressure generator configured to induce pressure changes in a sampling volume in which the particles from which the scattered light is being collected are disposed. For example, an ultrasound imaging probe can be inserted into the sampling volume, such that when the ultrasound imaging probe is energized, the particles in the sampling volume will experience changing pressure conditions. Ultrasound instruments or ultrasound transducers can be also positioned externally of, but acoustically coupled to, the sampling volume. Preferably, a sensor configured to measure the pressure changes in the sampling volume (such as the hydrophone described above) will also be added to the existing static light scattering particle sizing instruments.

The processing required to generate the RT curves, to fit the curves to dynamic models, and to derive shell parameters can be implemented by an additional processor, or the processor for the static light scattering particle sizing instrument can be modified (i.e., reprogrammed) to implement the additional functions.

Yet another aspect of collecting scattered light from one or more microbubbles during changing pressure conditions, is that the resulting data can be used to differentiate different types of microbubbles based on their different compressibility (as microbubbles of different compressibility will exhibit different changes in their respective diameters), because as discussed above, light scattering can be used to detect changes in diameters. Bubbles having a larger radius will scatter more light than bubbles having a smaller radius, and bubbles that are less compressible will exhibit larger radii than bubbles which are more compressible, during increased pressure conditions, enabling light scattering data to be used to differentiate microbubbles based on their compressibility.

Determining Particle Parameters Using a Modified Flow Cytometer:

FIG. 31 schematically illustrates an exemplary flow cytometer 100, modified to implement the concepts disclosed herein. The modification involves adding an acoustic transducer 130 to direct ultrasound energy toward a particle (such as a microbubble, a UCA, a microsphere, or a cell) immediately before or while light scattered by the particle is being collected. FIG. 35A graphically illustrates data collected from an unmodified flow cytometer, while FIGS. 35B-D graphically illustrate data collected from a flow cytometer modified to include the acoustic transducer noted above.

Referring to FIG. 31, flow cytometer 100 further includes a sample fluid delivery component 102, a fluid channel 104, a sample volume 110, a region of interest 106 in the sample volume, a laser light source 108, a scattered light collection component 112, a beam splitter 120, a first filter 122, a second filter 126, a first detector 124, and a second detector 128. Not specifically shown are fluid recovery components downstream of the sample volume for collecting fluid exiting the sample volume, and a system controller.

With the exception of the use of acoustic transducer 130 and additional data processing steps to analyze the data shown in FIGS. 35B-35D, flow cytometer 100 operates much as do conventional flow cytometers. Fluid delivery component 102 is used to direct a particle (or a population of particles) into fluid channel 104 at an appropriate flow rate and encompasses the elements required to provide that function. Those elements can include fluid lines, fluid reservoirs, one or more fluid pumps, and one or more valves. Those of ordinary skill in the art of flow cytometry will readily recognize how to implement fluid delivery component 102. Fluid channel 104 represents a fluid line coupling fluid delivery component 102 with sample volume 110. A quartz flow cell or cuvette represents an exemplary sample volume.

Defined within the sample volume is a region of interest. The region of interest is generally a cylindrical or cubical volume. Light from laser 108 is directed into the region of interest, and light scattered by an object or particle entrained in the flow of fluid passing through the region of interest is collected by scattered light collection component 112. While light sources other than a laser can be used, narrow waveband light sources are convenient, in that a corresponding filter can be placed in front of the sensor to remove light in wavebands outside that of the light source, efficiently reducing noise from other light sources.

The artisan of ordinary skill will recognize that many different combinations of optical elements can be used to implement scattered light collection component 112. The function of scattered light collection component 112 is simply to collect light scattered by the object in the region of interest and direct that light to one or more light sensors. Significantly, the scattered light will be used to provide intensity or amplitude information, as opposed to being used for imaging, so relatively simple optical components can be employed. An exemplary, rather than limiting scattered light collection component 112, includes a microscope objective 114, a lens 116, and a field stop 118. The artisan of ordinarily skill in optics will recognize that many modifications can be made to scattered light collection component 112 to successfully direct light scattered from an object in the region of interest to an appropriate light detector.

Exemplary modified flow cytometer 100 includes a first detector 124 and a second detector 128, and further includes a beam splitter 120 to direct light to each detector. The use of two detectors, and filters 122 and 126, enables flow cytometer 100 to collect both scattered light and fluorescent light from the same particle at the same time. The artisan of ordinarily skill in flow cytometry will readily recognize the utility of collecting fluorescence data. In this exemplary embodiment, detector 124 is used to collected scattered light, and filter 122 is used to remove light that has a wavelength different than the light emitted by laser 108 (the scattering of light by the object will not appreciably change the wavelength provided by the laser). Detector 128 is used to collect fluorescent light (if any) emitted from the particle, and filter 126 is used to remove light having a wavelength different than that emitted from a fluorescent dye used to tag the particles. (Note that fluorescent tagging is not required to implement the concepts disclosed herein, but such tagging is often found useful in flow cytometry. Accordingly, flow cytometer 100 represents a tool that can be used to simultaneously collect dynamic data from scattered light as well as fluorescence data). However, it should be understood that only a single light detector (for collecting scattered light) is required to implement the novel approach disclosed herein.

While not shown in FIG. 31, data from sensor 124 can be manipulated by a processor to determine one or more characteristics of the particle, generally as discussed above. It should also be recognized that flow cytometer 100 is intended to be exemplary, and that many different flow cytometer designs can be modified by the inclusion of an acoustic transducer to direct energy at a particle being interrogated by the flow cytometer.

Note that flow cytometer 100 does not specifically include an element to measure the ambient pressure conditions in the sample volume, as is employed in system 20 of FIG. 2 (see hydrophone 30). However, it should be recognized that such a pressure sensor can be incorporated into flow cytometer 100, if desired.

Some existing flow cytometer designs include a plurality of light sources (generally lasers) and a plurality of detectors, with different laser/detector combinations configured to collect light scattered by a particle from different portions of a sample volume. It should be recognized that the concepts disclosed herein can also be used to modify such flow cytometer designs.

The position of transducer 130 relative to the sample volume can be varied. The most significant requirement is that the transducer be disposed close enough to the region of interest that the particle will be vibrating (or oscillating, or otherwise responding to the pressure pulse) in response to the acoustic energy while in the region of interest (if the particle were no longer vibrating because the acoustic energy was directed at the particle too early, then the scattered light data would correspond to the data shown in FIG. 35A, as opposed to the data shown in FIGS. 35B-35D). It should be understood that the power source and control elements for transducer 130 have not been separately shown. The artisan of ordinary skill in the acoustic arts will readily recognize how to energize and control transducer 130.

Exemplary, but not limiting operating parameters for flow cytometer 100 are as follows: a flow channel having a diameter of about 150 microns; a flow rate of about 2 meters/second; a 200 mW 488 nm laser light source with a beam diameter of about 20 microns; and an acoustic transducer operating in the range of about 100 kHz to about 50 MHz. Where the particles are UCAs, the acoustic transducer can be operated in the range of from about 1 MHz to about 5 MHz. Where the particles are biological cells, the acoustic transducer can be operated in the range of from about 10 MHz to about 40 MHz.

FIGS. 32A and 32B are plan views of sample volume 110, showing the relative locations of the sample volume, the transducer, and laser 108. In these exemplary embodiments, the transducer is attached to one of four faces of the sample volume. The laser is disposed proximate a first face, and the face opposite and parallel to the first face is un-obstructed, to allow light scattered by the particle to exit that sample volume. The third and fourth faces are orthogonal to the first and second faces. In FIG. 32A, a transducer 130*a* is attached to the third face, while in FIG. 32B, a transducer 130*b* is attached to the fourth face. In a related embodiment, transducer 130*a* is attached to the third face and transducer 130*b* is attached to the fourth face. Using multiple transducers has the benefit of enabling different acoustic frequencies and intensities to be easily directed toward the particle in the sample volume. Of course, transducers whose output can be varied are available, and use of two transducers is thus not the only way to achieve such variability.

FIG. 32C is also a plan view of sample volume 110, showing the relative locations of the sample volume, the transducer, and laser 108. In this Figure, a transducer 130*c* having an annular opening 131 is attached to the first face of the sample volume, between laser 108 and the sample volume. The annular opening allows light from the laser to be directed into the region of interest of the sample volume.

FIGS. 33A-33C are side views of region of interest 106, where acoustic transducer 130 is disposed generally as shown in FIGS. 32A and 32B. Note that while the region of interest represents a portion of sample volume 110, for simplicity sake, the transducers in FIGS. 33A-33C are shown as attached to the region of interest (i.e., an inner portion of a flow cell or cuvette), as opposed to the sample volume (i.e., the flow cell or cuvette). The particle moving through the region of interest is illuminated by light from the light source (such as laser 108) while in region of interest 106, and light scattered by the particle while in the region of interest is collected by the detector (such as detector 124 of FIG. 31). As noted above, FIG. 35A graphically illustrates scatter intensity data collected from a conventional flow cytometer (i.e., a flow cytometer that does not include an acoustic transducer to direct acoustic energy toward the particle while (or immediately before) the light scattered by the particle is collected.

Referring to FIG. 33A, acoustic transducer 130 is providing a constant acoustic field 136 directed toward a particle 134 as it moves through the region of interest. FIG. 35B graphically illustrates data collected under such conditions. Note the differences between the smooth curve of FIG. 35A, and the fluctuating curve of FIG. 35B. The fluctuations can be analyzed (generally as discussed above) to determine one or more properties of the particle scattering the light.

Referring to FIG. 33B, acoustic transducer 130 is only energized while the particle initially enters the region of interest, such that particle 134 encounters an acoustic field 138 only as it initially enters the region of interest. After a period of time, the vibrations induced by the acoustic pulse decay, and the scattering intensity will no longer be dynamically varied. FIG. 35C graphically illustrates data collected under such conditions. Note the differences between the curve in FIG. 35C, the smooth curve of FIG. 35A, and the fluctuating curve of FIG. 35B. The intensity curve of FIG. 35C looks like a composite of the intensity curves of FIGS. 35A and 35B, with the fluctuating portion of the curve corresponding to the particle vibrating due to the acoustic pulse, and the smooth portion of the curve corresponding to the vibrating induced by the acoustic pulse fading away. Note that the speed of the particle, the intensity of the acoustic energy, and the duration of the initial acoustic pulse will effect the shape of the composite (or decay) curve of FIG. 35C. The decay curve of FIG. 35C can also be obtained using a transducer that does not extend along the entire height of the region of interest, but rather is limited to an initial upper portion of the region of interest. Furthermore, as long as the flow rate of the fluid passing through the region of interest is sufficiently high, the transducer can be located just upstream of the region of interest, such that the particle encounters the acoustic energy before entering the region of interest.

Referring to FIG. 33C, acoustic transducer 130 is utilized to direct a first acoustic field 140 toward particle 134 as it enters the region of interest, and a second different acoustic field 142 toward the particle in a different portion of the region of interest. Either a single transducer can be operated under different conditions to provide acoustic fields 140 and 142, or two different transducers can be employed.

FIG. 34A is a functional block diagram of another exemplary flow cytometer system including an acoustic transducer to direct acoustic energy toward a particle before or while light scattered by the particle is detected. In this Figure, dash lines indicate a logical connection between elements, and a solid line indicates a fluidic or optical connection. Such an exemplary flow cytometer system includes a sample fluid delivery component 140, a sample volume 142, an acoustic transducer 144, a light source 146, a scattered light sensor 148, a controller 150, and an optional sorting component 149.

Fluid delivery component 140 is used to direct a particle (or a population of particles) into the sample volume at an appropriate flow rate. Fluid delivery component 102 is intended to encompass the elements required to provide that function. Those elements can include fluid lines, fluid reservoirs, one or more fluid pumps, and one or more valves. Those of ordinary skill in the art of flow cytometry will readily recognize how to implement fluid delivery component 140. A quartz flow cell or cuvette represents an exemplary sample volume 110.

As discussed above, acoustic transducer 144 is positioned to direct acoustic energy toward a particle (such as a microbubble, a UCA, a microsphere, or a cell) immediately before, or while, light scattered by the particle is being collected.

Light from light source 146 is directed into the sample volume, and light scattered by an object entrained in the flow of fluid passing through the sample volume is collected by light sensor 148. As noted above, many different types of light sources can be used, laser light sources being exemplary, but not a limiting example of the type of light sources.

Controller 150 performs a plurality of functions. Data from light sensor 148 can be manipulated to determine one or more characteristics of the particle, generally as discussed above. Controller 150 can also be used to control the fluid delivery component (i.e., pumps and valves), the light source, and the acoustic transducer (of course, if desired, one or more additional controllers can be dedicated to control such elements).

Optional sorting component 149 can be used as follows. Dynamic scattering intensity spectrums (i.e., intensity spectrums collected as the particle is responding to an acoustic pressure pulse) for specific particles can be obtained and saved. A population of mixed particles can be introduced into the flow cytometer. As dynamic scattering intensity data for each particle is collected, controller 150 will send a control signal to sorting component 149 for each particle whose dynamic intensity spectrum corresponds to the previously determined dynamic intensity spectrum of a target particle. Sorting component 149 then directs that particle to a reservoir dedicated to collecting the target particles. In an exemplary embodiment, sorting component 149 includes one or more valves and a plurality of particle reservoirs and fluid lines.

Sorting component 149 uses the dynamic scattering intensity profile determined by controller 150 for each particle and manipulates the one or more valves as required to direct particles to specific reservoirs. For example, assume that dynamic scattering intensity spectrums have been identified for three different particle types. A population of particles that may include one or more of those three different particles is introduced into the modified flow cytometer (i.e., a flow cytometer including an acoustic transducer to enable dynamic scattering intensity spectrums to be collected). In such an embodiment, sorting component 149 can include four reservoirs, one for each of the three particle types, and one generic reservoir for all other types of particles. As the dynamic scattering intensity spectrum for each particle is determined, sorting component 149 can direct the particle to the appropriate reservoir.

While a power supply for components such as the controller, the light source, the sensor, and the transducer are not specifically shown, the artisan of ordinary skill will readily recognize how to incorporate such elements into the system.

FIG. 34B schematically illustrates an exemplary relationship between a light source used to illuminate a particle in a sample volume, and a light collection system used to collect light scattered by the particle and direct that light to a sensor. As indicated in FIG. 34B, the exemplary light collection system is disposed at an angle ranging from about 70 degrees to about 90 degrees relative to the laser source light path. An angle of about 82 degrees is particularly useful. It will be understood that this exemplary range is not required, and the concepts disclosed herein can be used in flow cytometers having different relative angles.

FIGS. 35A-35D graphically illustrate scattering intensity spectrums collected using a flow cytometer as discussed above. FIG. 35A graphically illustrates a static scattering intensity spectrum, where the particle from which light is being collected is not reacting to an applied pressure pulse or acoustic pulse. FIG. 35B graphically illustrates a dynamic scattering intensity spectrum, where the particle from which light is being collected is reacting to an applied pressure pulse or acoustic pulse, where that pulse is being applied to the particle continuously during the collection of light scattered by the particle. FIG. 35C graphically illustrates a dynamic scattering intensity spectrum, where the particle from which light is being collected is reacting to an applied pressure pulse or acoustic pulse, and where the pulse is initially applied and then terminated, so that pressure is not being applied to the particle during a latter portion of the light collection process. FIG. 35D graphically illustrates a plurality of dynamic scattering intensity spectrums, where each particle from which light is being collected is reacting to an applied pressure pulse or acoustic pulse. A dynamic scattering intensity spectrum 200 is reacting to a relatively small pressure pulse, while dynamic scattering intensity spectrum 202 is reacting to a relatively large pressure pulse. The pressure pulse employed was gradually increased for each dynamic scattering intensity spectrum between dynamic scattering intensity spectrum 200 and dynamic scattering intensity spectrum 202.

The concepts disclosed herein can be used in many different ways. Manufactures of UCA can use the techniques disclosed herein to characterize a new UCA under development. These techniques can also be beneficially employed to sort particles based on their dynamic scattering intensity spectrums (the term "dynamic" indicating that the scattering intensity profile is being collected while the particle is reacting to the application of a pressure wave or acoustic pulse). It is believed that dynamic scattering intensity spectrums can provide better differentiation of particles than static scattering intensity spectrums (the term "static" indicating that the scattering intensity profile is being collected while the particle is exposed to a constant pressure condition).

Exemplary Computing Environment

As noted above, the concepts disclosed herein involve analysis of a plurality of dynamic scattering intensity spectrums collected from particles in a flow of fluid, using a flow cytometer configured to direct a pressure pulse or acoustic pulse toward the particle. Reference has been made to an exemplary controller for performing the analysis. FIG. 36 and the following related discussion are intended to provide a brief, general description of a suitable computing environment for practicing the concepts disclosed herein, where the analysis required is implemented using a computing device generally like that shown in FIG. 36. Those skilled in the art will appreciate that the required image processing may be implemented by many different types of computing devices, including a laptop and other types of portable computers, multiprocessor systems, networked computers, mainframe computers, hand-held computers, personal data assistants (PDAs), and on other types of computing devices that include a processor and a memory for storing machine instructions, which when implemented by the processor, result in the execution of a plurality of functions used for implementing the present novel approach.

An exemplary computing system 151 suitable for implementing the analysis required includes a processing unit 154 that is functionally coupled to an input device 152, and an output device 162, e.g., a display. Processing unit 154 includes a central processing unit (CPU) 158 that executes machine instructions comprising a dynamic scattering intensity spectrum analysis program for implementing the functions disclosed herein (analyzing dynamic scattering intensity spectrums to enable at least one characteristic of a particle to be determined, and/or to sort particles in a population of particles). Those of ordinary skill in the art will recognize that processors or CPUs suitable for this purpose are available from Intel Corporation, AMD Corporation, Motorola Corporation, and other sources.

Also included in processing unit 154 are a random access memory 156 (RAM) and non-volatile memory 160, which typically includes read only memory (ROM) and some form of memory storage, such as a hard drive, optical drive, etc. These memory devices are bi-directionally coupled to CPU 158. Such data storage devices are well known in the art. Machine instructions and data are temporarily loaded into RAM 156 from non-volatile memory 160. Also stored in memory are the operating system software and ancillary software. While not separately shown, it should be understood that a power supply is required to provide the electrical power needed to energize computing system 151.

Input device 152 can be any device or mechanism that facilitates input into the operating environment, including, but not limited to, a mouse, a keyboard, a microphone, a modem, a pointing device, or other input devices. While not specifically shown in FIG. 36, it should be understood that computing system 151 is logically coupled to a modified flow cytometer system, such as that schematically illustrated in FIG. 31, so that the dynamic scattering intensity spectrums collected are available to computing system 151 to achieve the desired processing. Of course, rather than logically coupling the computing system directly to the flow cytometer system, data collected by the imaging system can simply be transferred to the computing system by means of many different data transfer means, such as portable memory media, or via a network (wired or wireless). Output device 162 will most typically comprise a monitor or computer display designed for human visual perception of an output image.

Although the concepts disclosed herein have been described in connection with the preferred form of practicing them and modifications thereto, those of ordinary skill in the art will understand that many other modifications can be made thereto within the scope of the claims that follow. Accordingly, it is not intended that the scope of these concepts in any way be limited by the above description, but instead be determined entirely by reference to the claims that follow.

The invention in which an exclusive right is claimed is defined by the following:

1. A system for measuring properties of a particle contained in a flow of fluid, comprising:
    (a) a sampling volume into which the flow of fluid containing the particle can be directed, the sampling volume including a region of interest;
    (b) an acoustic transducer configured to direct acoustic energy toward the particle when the particle is proximate the region of interest, such that the particle experiences a vibrational effect due to the acoustic energy while in at least a portion of the region of interest;
    (c) a light source for illuminating the region of interest with light;
    (d) a sensor for capturing light scattered by the particle while the particle is in the region of interest, producing a signal; and
    (e) a processor coupled to the sensor, the processor manipulating the signal from the sensor to determine at least one property of the particle in the region of interest.

2. The system of claim 1, further comprising an acoustic controller for controlling the acoustic transducer, such that at least one parameter selected from a group of parameters can be selectively varied, the group of parameters consisting of:
    (a) a frequency of the acoustic energy directed at the particle;
    (b) an amplitude of the acoustic energy directed at the particle; and
    (c) a duration of the acoustic energy directed at the particle.

3. The system of claim 2, wherein the acoustic controller is used to ensure that the acoustic transducer directs acoustic energy at the particle for an entire time, the particle is in the region of interest.

4. The system of claim 2, wherein the acoustic controller is used to ensure that the acoustic transducer does not direct acoustic energy at the particle for an entire time the particle is in the region of interest, such that a vibrational decay of the particle can be studied after the acoustic energy is no longer directed at the particle.

5. The system of claim 2, wherein the acoustic controller and the processor are the same control element.

6. The system of claim 1, wherein the acoustic transducer is disposed such that at least a portion of the region of interest is not exposed to acoustic energy from the acoustic transducer.

7. The system of claim 1, wherein the processor correlates relative scattered light intensity changes collected by the sensor with a radius of the particle.

8. The system of claim 1, wherein the processor implements the following functions:
    (a) controlling the acoustic transducer such that a pressure increase is induced in the region of interest, and such that scattered light is collected form the particle by the sensor during changing pressure conditions in the region of interest;

(b) correlating relative scattered light intensity changes collected by the sensor during the changing pressure conditions, with a radius of the particle;

(c) generating an amplitude and time relationship for tracking changes to an amplitude of a scattering intensity of the particle in the region of interest over time;

(d) fitting the radius and the time relationship to a dynamic model for describing the motion of a particle to determine a fitted relationship; and (e) determining one or more properties of the particle using the fitted relationship.

9. The system of claim 1, wherein the sampling volume comprises a flow cell, and wherein the acoustic transducer is attached to an exterior face of the flow cell.

10. The system of claim 1, wherein the flow cell comprises four exterior faces, the light from the light source being directed into the flow cell via a first face, light scattered from the particle exiting the flow cell from a second face, the first and second face being substantially parallel to each other, and wherein the acoustic transducer is attached to a third face, the third face being substantially perpendicular to the first face and the second face.

11. The system of claim 1, wherein the flow cell comprises four exterior faces, the light from the light source being directed into the flow cell via a first face, light scattered from the particle exiting the flow cell from a second face, the first and second face being substantially parallel to each other, and wherein the acoustic transducer is attached to the first face, the acoustic transducer comprising an annular opening through which the light from the light source can be directed into the flow cell.

12. The system of claim 1, wherein the flow cell comprises four exterior faces, the light from the light source being directed into the flow cell via a first face, light scattered from the particle exiting the flow cell from a second face, the first and second face being substantially parallel to each other, and wherein the acoustic transducer is attached to a third face, and an additional acoustic transducer is attached to the fourth face, the third and fourth faces being substantially parallel to each other, and substantially perpendicular to the first face and the second face, the transducer and the additional transducer being configured to provide different acoustical outputs.

13. The system of claim 1, wherein the flow cell comprises four exterior faces, the light from the light source being directed into the flow cell via a first face, light scattered from the particle exiting the flow cell from a second face, the first and second face being substantially parallel to each other, and wherein the acoustic transducer is attached to a third face, and an additional acoustic transducer is attached to the fourth face, the third and fourth faces being substantially parallel to each other, and substantially perpendicular to the first face and the second face, the transducer and the additional transducer being configured to provide equivalent acoustical outputs.

14. The system of claim 1, further comprising a sorting component downstream of the sample volume, the sorting component being logically coupled to the controller, the sorting element enabling a particle exiting the sample volume to be selectively directed to one of a plurality of storage volumes based on a dynamic scattering intensity profile as determined by the controller as a function of the light scattered by the particle.

15. A method for measuring properties of particles using scattered light, comprising the steps of:

(a) directing acoustic energy at a particle entrained in a flow of fluid;

(b) illuminating the particle entrained in the flow of fluid;

(c) collecting light scattered from the particle, while the particle is vibrating as a result of interacting with the acoustic energy; and (d) correlating relative scattered light intensity changes collected while the particle is vibrating as a result of interacting with the acoustic, energy with at least one property of the particle.

16. The method of claim 15, wherein the step of correlating relative scattered light intensity changes collected while the particle is vibrating as a result of interacting with the acoustic energy, with at least one property of the particle, comprises the steps of:

(a) generating a scattering intensity amplitude and time relationship for tracking changes to the radius of the particle over time;

(b) fitting the scattering intensity amplitude and time relationship to a dynamic model for describing a motion of the particle, to produce a fitted relationship; and (c) determining one or more properties of the particle using the fitted relationship.

17. The method of claim 15, wherein the step of collecting the light scattered from the particle entrained in a flow of fluid, while the particle is vibrating as a result of interacting with the acoustic energy, comprises the step of collecting the light scattered from the particle while the particle is exposed to a constant acoustic field.

18. The method of claim 15, wherein the step of collecting the light scattered from the particle entrained in the flow of fluid, while the particle is vibrating as a result of interacting with the acoustic energy, comprises the step of collecting the light scattered from the particle while the particle is exposed to a varying acoustic field.

19. The method of claim 15, wherein the step of collecting the light scattered from the particle entrained in the flow of fluid, while the particle is vibrating as a result of interacting with the acoustic energy, comprises the step of collecting the light scattered from the particle after the particle is no longer exposed to the acoustic field.

20. The method of claim 15, further comprising the step of using the at least one property of the particle to determine whether the particle is a member of a predefined group of particles, and if so, diverting the particle to a volume designated to store the predefined group of particles.

21. The method of claim 15, further comprising the steps of:

(a) collecting light scattered from a plurality of different particles using the steps used to collect the light scattered from the particle; and (b) for each particle of the plurality of different particles, using the at least one property identified using the light scattered to sort the plurality of particles into at least two different groups.

22. An optical flow cytometer, comprising:

(a) a sampling volume into which a flow of fluid containing a particle can be directed, the sampling volume including a region of interest;

(b) an acoustic transducer configured to direct acoustic energy toward the particle when the particle is proximate the region of interest, such that the particle experiences a vibrational effect due to the acoustic energy while in at least a portion of the region of interest;

(c) a light source for illuminating the region of interest with light;

(d) a sensor for capturing light scattered by the particle while the particle is in the region of interest, producing a signal; and (e) a processor coupled to receive the signal from the sensor, the processor manipulating the signal from the sensor to determine at least one property of the particle in the region of interest as a function of scattering intensity.

23. A method for measuring at least one property of a particle using scattered light, comprising the steps of:
 (a) collecting light scattered from a particle during changing pressure conditions experienced by the particle;
 (b) generating a scattering intensity amplitude and time relationship for the particle using data collected during the changing pressure conditions;
 (c) fitting the scattering intensity amplitude and time relationship to a model for describing the motion of the particle, to produce a fitted relationship; and
 (d) determining at least one property of the particle using the fitted relationship.

* * * * *